United States Patent
Seyed Momen et al.

(10) Patent No.: US 8,237,558 B2
(45) Date of Patent: Aug. 7, 2012

(54) HAND HYGIENE COMPLIANCE SYSTEM

(75) Inventors: Kaveh Seyed Momen, North York (CA); Geoffrey Roy Fernie, Etobicoke (CA); Oleksandr Igorovich Levchenko, Mississauga (CA); Graham Clive Hufton, New York, NY (US)

(73) Assignee: University Health Network, Toronto (CA)

( * ) Notice: Subject to any disclaimer, the term of this patent is extended or adjusted under 35 U.S.C. 154(b) by 485 days.

(21) Appl. No.: 12/569,770

(22) Filed: Sep. 29, 2009

(65) Prior Publication Data
US 2010/0117836 A1    May 13, 2010

Related U.S. Application Data

(63) Continuation-in-part of application No. 12/078,186, filed on Mar. 27, 2008, now Pat. No. 7,898,407, and a continuation-in-part of application No. PCT/CA2008/000534, filed on Mar. 27, 2008.

(60) Provisional application No. 61/136,720, filed on Sep. 29, 2008, provisional application No. 60/920,779, filed on Mar. 30, 2007, provisional application No. 60/960,521, filed on Oct. 2, 2007.

(51) Int. Cl.
*G08B 1/08* (2006.01)
*G08B 23/00* (2006.01)
*B67D 7/06* (2010.01)

(52) U.S. Cl. .......... 340/539.11; 340/539.12; 340/573.1; 340/286.07; 222/23

(58) Field of Classification Search ............. 340/539.11, 340/573.1
See application file for complete search history.

(56) References Cited

U.S. PATENT DOCUMENTS

| 692,089 A | 1/1902 | Swisher |
|---|---|---|
| 2,059,135 A | 1/1936 | Moe |
| 2,113,022 A | 4/1938 | Hefti |
| 2,235,350 A | 3/1941 | Violet |
| 2,975,719 A | 3/1961 | Kaufman |
| 3,202,331 A | 8/1965 | Robert |
| 3,273,752 A | 9/1966 | Horeczky |
| 3,434,628 A | 3/1969 | Ceraldi |
| 3,478,344 A | 11/1969 | Schwitzgebel et al. |
| 3,480,787 A | 11/1969 | Johansen |

(Continued)

FOREIGN PATENT DOCUMENTS
WO    WO 2006/119373    11/2006
(Continued)

OTHER PUBLICATIONS

Inuzaka and Hyodo, "Research on Healthcare Worker Behavior to Increase Hand Hygiene Compliance in a Japanese Hospital", Poster Abstracts: Infection Prevention and Control Programs, Publication No. 9-122, 34th Annual Education Conference & International Meeting, Jun. 24-28, 2007, San Jose, CA, p. 85.

(Continued)

*Primary Examiner* — Donnie Crosland

(57) ABSTRACT

A system and method of encouraging compliance of hand hygiene in an environment where users move from zone to zone and are required to perform hand hygiene between the zones. Users carry a wearable zone sensor which detects zones, detects hand hygiene actions, logs time of changing zones, and hand hygiene actions. The wearable sensor can be integral with a wearable hand hygiene product dispenser and/or can operate in cooperation with a fixed dispenser configured to transmit hand hygiene actions to the wearable zone sensor. The wearable zone sensors are configured to be useable anonymously or to be associated with a user identifier, and to interface with a central computer via a docking station or communication interface to transfer data for later analysis.

24 Claims, 28 Drawing Sheets

U.S. PATENT DOCUMENTS

| | | |
|---|---|---|
| 3,516,575 A | 6/1970 | Moffitt |
| 3,547,324 A | 12/1970 | Parks |
| 3,612,353 A | 10/1971 | Haase |
| 3,630,172 A | 12/1971 | Neumann et al. |
| 3,635,189 A | 1/1972 | Whittemore |
| 3,647,115 A | 3/1972 | McCann et al. |
| 3,650,435 A | 3/1972 | Kleefeld |
| 3,696,384 A | 10/1972 | Lester |
| 3,739,329 A | 6/1973 | Lester |
| 3,843,020 A | 10/1974 | Bardeau et al. |
| 3,843,032 A | 10/1974 | Moran et al. |
| 3,881,641 A | 5/1975 | Pliml, Jr. et al. |
| 3,967,478 A | 7/1976 | Guinn |
| 3,993,251 A | 11/1976 | Des Garets |
| 4,053,233 A | 10/1977 | Bien et al. |
| 4,058,237 A | 11/1977 | Luke |
| 4,087,675 A | 5/1978 | Sansonetti |
| 4,145,769 A | 3/1979 | MacFarlane et al. |
| 4,164,306 A | 8/1979 | Perrin |
| 4,175,704 A | 11/1979 | Cohen |
| 4,271,988 A | 6/1981 | Clausen |
| 4,275,385 A | 6/1981 | White |
| 4,349,133 A | 9/1982 | Christine |
| 4,381,022 A | 4/1983 | Medynski |
| 4,420,097 A | 12/1983 | Motsenbocker |
| 4,513,885 A | 4/1985 | Hogan |
| 4,515,294 A | 5/1985 | Udall |
| 4,550,676 A | 11/1985 | Francis |
| 4,564,127 A | 1/1986 | Garabedian et al. |
| 4,570,827 A | 2/1986 | Roggenburg, Jr. et al. |
| 4,573,612 A | 3/1986 | Maddison et al. |
| 4,582,227 A | 4/1986 | Kanfer |
| 4,603,794 A | 8/1986 | Deford et al. |
| 4,606,085 A | 8/1986 | Davies |
| 4,615,476 A | 10/1986 | Hobbs et al. |
| 4,620,646 A | 11/1986 | Crapser |
| 4,634,022 A | 1/1987 | O'Halloran et al. |
| 4,635,689 A | 1/1987 | Graffin |
| 4,637,934 A | 1/1987 | White |
| 4,645,094 A | 2/1987 | Acklin et al. |
| 4,662,873 A | 5/1987 | Lash et al. |
| 4,667,854 A | 5/1987 | McDermott et al. |
| 4,673,109 A | 6/1987 | Cassia |
| 4,689,935 A | 9/1987 | Harding |
| 4,703,871 A | 11/1987 | Broker |
| 4,709,330 A | 11/1987 | Yokoi et al. |
| 4,711,373 A | 12/1987 | Christine |
| 4,722,372 A | 2/1988 | Hoffman et al. |
| 4,736,876 A | 4/1988 | Kriss |
| 4,741,461 A | 5/1988 | Williamson et al. |
| 4,768,688 A | 9/1988 | Harrigan |
| 4,793,517 A | 12/1988 | Washut |
| 4,886,192 A | 12/1989 | Cassia |
| 4,896,144 A | 1/1990 | Bogstad |
| 4,938,384 A | 7/1990 | Pilolla et al. |
| 4,944,429 A | 7/1990 | Bishop et al. |
| 4,946,070 A | 8/1990 | Albert et al. |
| 4,946,072 A | 8/1990 | Albert et al. |
| 4,952,928 A | 8/1990 | Carroll et al. |
| 4,967,935 A | 11/1990 | Celest |
| 4,990,892 A | 2/1991 | Guest et al. |
| 5,016,172 A | 5/1991 | Dessertine |
| 5,016,781 A | 5/1991 | Ten Wolde |
| 5,018,646 A | 5/1991 | Billman et al. |
| D317,984 S | 7/1991 | Reynoso et al. |
| 5,031,258 A | 7/1991 | Shaw |
| 5,037,389 A | 8/1991 | Dooley |
| 5,046,648 A | 9/1991 | Herbstzuber |
| 5,072,935 A | 12/1991 | Mcwain |
| 5,088,624 A | 2/1992 | Hackett |
| 5,117,766 A | 6/1992 | Nechushtan et al. |
| 5,129,999 A | 7/1992 | Holland et al. |
| 5,148,949 A | 9/1992 | Luca |
| 5,154,318 A | 10/1992 | Lampard |
| 5,199,609 A | 4/1993 | Ash, Jr. |
| 5,202,666 A | 4/1993 | Knippscheer |
| 5,204,670 A | 4/1993 | Stinton |
| 5,215,227 A | 6/1993 | Farner |
| 5,248,066 A | 9/1993 | Olson et al. |
| 5,261,570 A | 11/1993 | Hippely et al. |
| 5,265,628 A | 11/1993 | Sage et al. |
| 5,265,772 A | 11/1993 | Bartasevich et al. |
| 5,284,133 A | 2/1994 | Burns et al. |
| 5,289,948 A | 3/1994 | Moss et al. |
| 5,307,953 A | 5/1994 | Regan |
| 5,341,993 A | 8/1994 | Haber et al. |
| 5,348,193 A | 9/1994 | Bruckner et al. |
| 5,363,842 A | 11/1994 | Mishelevich et al. |
| 5,370,267 A | 12/1994 | Schroeder |
| 5,387,993 A | 2/1995 | Heller et al. |
| 5,411,173 A | 5/1995 | Weinstein |
| 5,414,405 A | 5/1995 | Hogg et al. |
| 5,420,797 A | 5/1995 | Burns |
| 5,421,489 A | 6/1995 | Holzner, Sr. et al. |
| 5,429,301 A | 7/1995 | Franks |
| 5,443,236 A | 8/1995 | Bell et al. |
| 5,455,851 A | 10/1995 | Chaco et al. |
| 5,458,135 A | 10/1995 | Patton et al. |
| 5,464,125 A | 11/1995 | Daansen |
| 5,465,877 A | 11/1995 | Bell et al. |
| 5,484,085 A | 1/1996 | Bennett |
| RE35,187 E | 3/1996 | Gortz |
| 5,503,302 A | 4/1996 | Dejonge |
| 5,505,192 A | 4/1996 | Samiotes et al. |
| 5,509,578 A | 4/1996 | Livingstone |
| 5,537,992 A | 7/1996 | Bjoernstijerna et al. |
| 5,538,164 A | 7/1996 | Rivas |
| 5,566,869 A | 10/1996 | Katz |
| 5,582,323 A | 12/1996 | Kurtenbach |
| 5,608,643 A | 3/1997 | Wichter et al. |
| 5,610,589 A | 3/1997 | Evans et al. |
| 5,620,656 A | 4/1997 | Wensky et al. |
| 5,622,163 A | 4/1997 | Jewett et al. |
| 5,625,659 A | 4/1997 | Sears |
| 5,632,414 A | 5/1997 | Merriweather, Jr. |
| 5,669,529 A | 9/1997 | Levit |
| 5,670,945 A | 9/1997 | Applonie |
| 5,678,720 A | 10/1997 | Van Melle |
| 5,678,730 A | 10/1997 | Fabek et al. |
| 5,683,012 A | 11/1997 | Villaveces |
| 5,695,091 A | 12/1997 | Winings et al. |
| 5,774,865 A | 6/1998 | Glynn |
| 5,793,653 A | 8/1998 | Segal |
| 5,798,714 A | 8/1998 | Nyfelt |
| 5,808,553 A | 9/1998 | Cunningham |
| 5,810,201 A | 9/1998 | Besse et al. |
| 5,812,059 A | 9/1998 | Shaw et al. |
| 5,815,467 A | 9/1998 | Deering |
| 5,824,407 A | 10/1998 | Hayashi et al. |
| 5,830,490 A | 11/1998 | Weinstein et al. |
| 5,836,482 A | 11/1998 | Ophardt et al. |
| 5,850,344 A | 12/1998 | Conkright |
| 5,860,437 A | 1/1999 | Fernie |
| 5,862,956 A | 1/1999 | Brandenburg et al. |
| 5,863,497 A | 1/1999 | Dirksing |
| 5,867,829 A | 2/1999 | Hegoas et al. |
| 5,870,015 A | 2/1999 | Hinkel |
| D408,988 S | 5/1999 | Barber et al. |
| 5,900,067 A | 5/1999 | Jones |
| 5,912,818 A | 6/1999 | Mcgrady et al. |
| 5,917,425 A | 6/1999 | Crimmins et al. |
| 5,924,601 A | 7/1999 | Chen |
| 5,927,548 A | 7/1999 | Villaveces |
| 5,939,974 A | 8/1999 | Heagle et al. |
| 5,941,241 A | 8/1999 | Weinstein et al. |
| 5,944,227 A | 8/1999 | Schroeder et al. |
| 5,945,910 A | 8/1999 | Gorra |
| 5,952,924 A | 9/1999 | Evans et al. |
| 5,954,069 A | 9/1999 | Foster |
| 5,960,991 A | 10/1999 | Ophardt |
| 5,972,126 A | 10/1999 | Fernie |
| D416,417 S | 11/1999 | Ross et al. |
| 6,038,331 A | 3/2000 | Johnson |
| 6,065,639 A | 5/2000 | Maddox et al. |
| 6,125,482 A | 10/2000 | Foster |
| 6,131,773 A | 10/2000 | Wade et al. |
| 6,161,227 A | 12/2000 | Bargenquast |

| | | | |
|---|---|---|---|
| 6,236,317 | B1 | 5/2001 | Cohen et al. |
| 6,236,953 | B1 | 5/2001 | Segal |
| 6,278,372 | B1 | 8/2001 | Velasco, Jr. et al. |
| 6,283,334 | B1 | 9/2001 | Mahaffey et al. |
| 6,325,245 | B1 | 12/2001 | Matthews |
| 6,375,038 | B1 | 4/2002 | Daansen et al. |
| 6,386,390 | B1 | 5/2002 | Tinker |
| 6,392,546 | B1 | 5/2002 | Smith |
| 6,426,701 | B1 | 7/2002 | Levy et al. |
| 6,467,651 | B1 | 10/2002 | Muderlak et al. |
| 6,524,390 | B1 | 2/2003 | Jones |
| 6,537,244 | B2 | 3/2003 | Paukovits et al. |
| 6,564,999 | B1 | 5/2003 | Saveliev et al. |
| 6,577,240 | B2 | 6/2003 | Armstrong |
| 6,727,818 | B1 | 4/2004 | Wildman et al. |
| 6,875,539 | B2 | 4/2005 | Ophardt |
| 6,876,303 | B2 | 4/2005 | Reeder et al. |
| 6,882,278 | B2 | 4/2005 | Winings et al. |
| 6,883,563 | B2 | 4/2005 | Smith |
| 6,897,780 | B2 | 5/2005 | Ulrich et al. |
| 6,937,150 | B2 | 8/2005 | Medema et al. |
| 6,938,795 | B2 | 9/2005 | Barton et al. |
| 6,970,574 | B1 | 11/2005 | Johnson |
| D512,648 | S | 12/2005 | Smith et al. |
| 6,975,231 | B2 | 12/2005 | Lane et al. |
| 6,982,639 | B2 | 1/2006 | Brackett et al. |
| 6,983,864 | B1 | 1/2006 | Cagle |
| 6,990,391 | B1 | 1/2006 | Cunha et al. |
| 7,015,816 | B2 | 3/2006 | Wildman et al. |
| 7,070,067 | B1 | 7/2006 | Buchanan et al. |
| 7,114,510 | B2 | 10/2006 | Peters et al. |
| 7,135,011 | B2 | 11/2006 | Powers et al. |
| 7,242,307 | B1 | 7/2007 | LeBlond et al. |
| 7,271,728 | B2 | 9/2007 | Taylor et al. |
| 7,286,057 | B2 | 10/2007 | Bolling |
| 7,482,936 | B2 | 1/2009 | Bolling |
| 7,605,704 | B2 | 10/2009 | Munro et al. |
| 7,818,083 | B2 | 10/2010 | Glenn et al. |
| 7,825,812 | B2 | 11/2010 | Ogrin et al. |
| 7,855,651 | B2 | 12/2010 | LeBlond et al. |
| 2002/0000449 | A1 | 1/2002 | Armstrong |
| 2002/0135486 | A1 | 9/2002 | Brohagen et al. |
| 2003/0019536 | A1 | 1/2003 | Smith |
| 2003/0030562 | A1 | 2/2003 | Lane et al. |
| 2003/0033669 | A1 | 2/2003 | Fernie |
| 2004/0090333 | A1 | 5/2004 | Wildman et al. |
| 2004/0138631 | A1 | 7/2004 | Harper |
| 2004/0150527 | A1 | 8/2004 | Harper et al. |
| 2005/0248461 | A1 | 11/2005 | Lane et al. |
| 2006/0013739 | A1 | 1/2006 | Castillo et al. |
| 2006/0132316 | A1 | 6/2006 | Wildman et al. |
| 2006/0240397 | A1 | 10/2006 | Lynn et al. |
| 2006/0289567 | A1 | 12/2006 | Shoham et al. |
| 2007/0008146 | A1 | 1/2007 | Taylor et al. |
| 2007/0015552 | A1 | 1/2007 | Bolling |
| 2007/0213877 | A1 | 9/2007 | Hart et al. |
| 2007/0222554 | A1 | 9/2007 | Hart |
| 2008/0001763 | A1 | 1/2008 | Raja et al. |

FOREIGN PATENT DOCUMENTS

| | | | |
|---|---|---|---|
| WO | WO/2008/119158 | A1 | 10/2008 |
| WO | WO/2008/119158 | | 9/2009 |
| WO | WO/2010/034125 | A1 | 4/2010 |

OTHER PUBLICATIONS

Broughall et al., An automatic monitoring system for measuring handwashing frequency in hospital wards, Journal of Hospital Infection, 1984, p. 447, vol. 5, Elsevier, online.

Voss and Widmer, No Time for Handwashing, Infection Control and Hospital Epidemiology, 1997, p. 205, vol. 18, 3, ProQuest Nursing & Allied Health Source, online.

Xhale Innovations Inc., Hygreen: The Intelligent Hand Hygiene System, 2009, www.xhale.com/hygreen/index.asp, Xhale Innovations Inc., Florida, USA.

Harbor Medical, Inc., The Sprixx Hand Hygiene System, 2007, www.sprixx.com/shhsoverview.html, Harbor Medical, Inc., CA, USA.

Zhou et al, Activity analysis, summerization, and visualization . . . , IEEE Transactions on Circuits and Systems for Video Technology, 2008, pp. 1489-1498, v18.

Nguyen et al, Recognizing and monitoring high-level . . . IEEE Computer Society Conference on Computer Vision and Pattern Recognition, 2, 2003, 620-625.

Ohmura et al, B-pack: A bluetooth-based wearable sensing device for nursing activity recognition, 1st International Symposium, 2006, p. 6.

Naya et al, Workers' routine activity recognition using body movements and location information, Wearable Computers, 10th IEEE International Symposium, 2006 p. 105-108.

Minnen et al, Recognizing and discovering human actions from on-body sensor data, IEEE International Conference on Multimedia and Expo, 2005 p. 1545-1548.

Pirttikangas et al, Feature Selection and Activity Recognition from Wearable Sensors, Berlin: Springer-Verlag Berlin, 2006, pp. 516-527, vol. 4239.

Karantonis et al, Implementation of a real-time human movement classifier . . . , IEEE Transactions on Information Technology in Biomedicine, 2006, pp. 156-167, vol. 10.

Thies et al, Comparison of linear acceleration from three measurements systems during reach and grasp, Medical Engineering and Physics, Nov. 2007, p. 967-972, vol. 29.

Henmi et al, A biomechanical study of activities of daily living using neck and upper limbs . . . , Mod Rheumatol,Oct. 2006, pp. 289-293, vol. 16.

Bao and Intille, Activity recognition from user-annotated acceleration data, Berlion: Springer-Verlag Berlin, 2004, pp. 1-17, vol. 3001.

Ravi et al, Activity recognition from accelerometer data, Proceedings of the National Conference on Artificial Intelligence, 2005, (3) p. 1541-1546.

Lester et al, A practical approach to recognizing physical activities, Pervasive Computing, 2006, pp. 1-16, vol. 3968.

Nguyen et al, Unsupervised clustering of free-living human activities using ambulatory accelerometry, Conf Proc IEEE Eng Med Biol Soc 2007, pp. 4895-4898, vol. 1.

Lukowicz et al, Recognizing Workshop Activity using body worn microphones and accelerometers, Lecture Notes in Computer Science, 2004, pp. 18-32, vol. 3001/2004.

Duong et al, Activity recognition and abnormality detection with . . . ,Proceedings 2005 IEEE Computer Society Conference on Compute recognition, pp. 838-845, vol. 1, Jun. 2005.

Chen et al, Bathroom activity monitoring based on sound, Pervasive Computing. Third International Conference, 2005, pp. 47-61, vol. 3468.

Helmi et al, Human activity recognition using a fuzzy inference system, FUZZ-IEEE 2009. IEEE International Conference on Fuzzy Systems, Oct. 2, 2009, pp. 1897-1902.

Godfrey et al, Direct measurement of human movement by accelerometry, Medical Engineering and Physics,2008, pp. 1364-1386, vol. 30.

Moore et al, Comparing hand hygiene adherence rates for existing hand hygiene products . . . , Canadian Hospital Infection Control and Association, Annual Meeting, May 6-10, 2006.

Van De Mortel and Murgo, An examination of covert observation and solution audit tools . . . ,American journal of Infection Control, 2006, pp. 95-99, vol. 34(3).

Dubbert et al, Increasing ICU staff handwashing: effects of education and group feedback, Infect Control Hosp Epidemiol, 1990, p. 191-193, vol. 11.

Van De Mortel and Heyman, Performance feedback increases the incidence of handwashing by staff following patient contact in intensive care, Aust Crit Care, 1995, p. 8-13, vol. 8.

Pittet et al, Effectivness of a hospitasl-wide programme to improve compliance with hand hygiene, Lancet, 2005, pp. 1307-1312, vol. 356.

Tvedt and Bukholm, Alcohol-based hand disinfection: a more robust hand-hygiene method in an intensive care unit, J Hosp Infect, 2005, pp. 229-234, vol. 59.

Swoboda et al, Electronic monitoring and voice prompts improve hand hygiene and decrease nosocomial infections . . . , Crit Care Med, 2004, pp. 358-363, vol. 32.

Boyce, Hand Hygiene compliance monitoring: current perspectives from the USA, Journal of Hospital Infections, 2008, pp. 2-7, vol. 70.

Kinsella et al, Electronic surveillance of wallmounted soap and alcohol gel dispensers in an intensive care unit, Journal of Hospital Infection, 2007, pp. 34-39, vol. 66.

Rosenthal et al, Reduction of nosocomical infection with improved hand hygiene in intensive care units . . . , Am J Infect Control, 2005, pp. 392-397, vol. 33 (7).

Creedon, Health care workers' hand decontamination practices: an Irish study, Clinical Nursing Research, 2006, pp. 6-26, vol. 15(1).

BioVigil Industries, http://www.earthtimes.org/articles/show/biovigil-releases-secondgeneration-hand-hygiene-monitoring-system, 1206560.shtml.

Boscart et al, Acceptability of a wearable hand wash device with monitoring capabilities, J Hosp Infect, 2008, pp. 216-222, vol. 70.

Boscart et al, Automated hand hygiene monitoring: perspectives for healthcare staff, management, and infection control specialists, J Europ Assoc Hosp Manage, 2009, pp. 15-16.

Levchenko et al, Embedded system for hygiene compliance monitoring, IEEE Transactions on Automation Science and Engineering, 2009, (in press).

Boscart et al, Defining the configuration of a hand hygiene monitoring system. American journal of Infection Control, 2009, (in press).

Boscart et al, Advanced technologies to curb healthcare-associated infections. Invited commentary Healthcare Papers, 2009, pp. 51-55, vol. 9(3).

Fernie et al, Technology to reduce institutional cross-infection rates . . . , 6th Conference of the International Society for Gerontechnology, May 20-23, 2008 Pisa, Italy.

Levchenko et al, Distributed IR based technology to monitor hand hygiene of healthcare staff, IEEE TIC STH, 2009, p. 252-255.

Boscart and Levchenko, Advanced technology . . . clinical setting. International Conference & Workshops RNAO, 'Nurses: The Solution . . . Transformation', Oct. 2008, Beijing, China.

Boscart et al, Hand hygiene compliance . . . healthcare staffInstitute for Healthcare Improvement's National Forum on Quality Improvement in Health Care, Apr. 2009, Canada.

Boscart et al, Testing of a portable . . . in the clinical setting. Health Professions Education, Global Best Practices in Simulation, May 2009, Toronto Canada.

Meritech Cleantech, http://www.meritech.com/products/radius/index.php, Golden, Colorado.

RadarFind Corporation, http://www.baumpub.com/hc1016, Morrisville, North Carolina.

Versus Technology, http://www.versustech.com/technology.html, Traverse City, Michigan.

Resurgent Health and Medical, http://resurgenthealth.com/skinHealth/index.html. Golden Colorado.

Hui et al, Distributed community detection in delay tolerant networks, MobiArch, Aug. 27-31, 2007, vol. 07, Kyoto Japan.

Yoneki et al, Visualizing community detection in opportunistic networks, Chants, Sep. 14, 2007, Montreal Quebec.

Aiello et al, The Influence of knowledge, perceptions, and beliefs, on hand hygiene practices in nursing homes, Assoc Profession Infect Cont Epid, 2008.

Assanasen et al, Impact of 2 different levels of performance feedback on compliance with infection control process measures in 2 intensive , AJIC, 2008, pp. 407-413, vol. 36(6).

Backman et al, An integrative review of the current evidence on the relationship between hand hygiene interventions . . . , AJIC, Jun. 2008, pp. 333-348, vol. 36(5).

Cantrell et al, Hand hygiene compliance by physicians: marked heterogeneity due to local culture? AJIC, May 2009, pp. 301-305, vol. 37(4).

Cromer et al, Monitoring and feedback of hand hygiene compliance and the impact on faculty . . . , AJIC, Nov. 2008, pp. 672-677, vol. 36(9).

Pittet and Boyce, Hand hygiene and patient care: pursuing the Semmelweis legacy, The Lancet Infectious Diseases, The Lancet, Apr. 2001, p. 9-20, vol. 1 ( supp 1).

Edwards et al, National healthcare safety network (NHSN) report, data summary for 2006 through 2007, issued Nov. 2008, AJIC, pp. 609-626, vol. 36(9).

Gould et al, Measuring handwashing performance in health service audits and research studies, J Hosp Infection, 2007, pp. 109-115, vol. 66.

Larson et al, Hand Hygiene Behavior in a Pediatric Emergency Department and a Pediatric Intensive Care Unit . . . , Am J Crit Care, Jul. 2005, pp. 304-312, vol. 14(4).

Haas and Larson, Measurement of compliance with hand hygiene, Journal of Hospital Infection, 2007, pp. 6-14, vol. 66.

Forman et al, Qualitative research methods: Key features and insights gained from use in infection prevention research, AJIC, Dec. 2008, In press.

Gould et al, Interventions to improve hand hygiene compliance in patient care (review), the Cochrane Collaborations, 2007, Issue 7, John Wiley and Sons LTD.

Zoutman et al, A cross Canada survey of infection prevention and control in long-term care facilities, AM J Infect Control, 2009, pp. 358-363, vol. 37.

Zoutman and Ford, A comparison of infection control program resources, activities, and antibiotic resistant organism . . . , AJIC, Dec. 2008, In press.

Zoutman and Ford, The relationship between hospital infection surveillance and control activities, AJIC, 2005, pp. 1-5, vol. 33(1).

Zoutman et al, The state of infection surveillance and control in Canadian acute care hospitals, AJIC, 2003, pp. 266-273, vol. 31(5).

Venkatesh et al, Use of electronic alerts to enhance hand hygiene compliance and decrease transmission . . . ,AJIC, Apr. 2008, pp. 199-205, vol. 36(3).

Siegel et al, Keeping patients safe: an interventional hand hygiene study at an oncology centre, Clin J Oncology Nurs, Oct. 2007, pp. 643-646, vol. 11(5).

Smith and Rusnak, Infection Prevention and Control in the Long-Term-Care Facility, Infect Control Hospital Epidemiology, 1997, pp. 831-849, vol. 18.

Kohan et al, The importance of evaluating product dispensers when selecting alcohol-based handrubs, AJIC, Oct. 2002, pp. 373-375, vol. 30(6).

Swoboda et al, Isolation status and voice prompts improve hand hygiene, AJIC, Sep. 2007, pp. 470-476, vol. 35(7).

Whitby et al, Behavioural considerations for hand hygiene practices: the basic building blocks, Journal of Hospital Infection, 2007, pp. 1-8, vol. 65.

Whitby et al, Three successful interventions in healthcare workers that improve compliance with hand hygiene: Is sustained replication possible?, AJIC, 2008, pp. 349-355, vol. 36.

World Health Organization, WHO Guidelines on Hand Hygiene in Health Care (Advanced Draft): A Summary, WHO, 2005, France.

Medonyx, http://www.medonyx.com/newsite/index.htm, 2006, Toronto.

Trick et al, Multicenter Intervention Program to Increase Adherence to Hand Hygiene . . . , Infection Control and Hospital Epidemiology, Jan. 2007, pp. 42-49, vol. 28(1).

Steripower GM.BH & CO KG, www.steripower.de, Starnberg / Germany.

Urbantool, https://webshop.urbantool.com/us/shirts/advancedshirt-male, Arizona.

Plaggemeier, MRSA: a big bad bug, Long Term Care, Jun./Jul. 2008, pp. 21-23, vol. 18(2).

McGuckin, The effect of random voice hand hygiene messages . . . , AJIC, Dec. 2006, pp. 673-675, vol. 34 (10).

Lent et al, Evaluation of patient participation in a patient empowerment initiative to improve hand hygiene practices . . . , AJIC, Mar. 2008, In press.

Ultraclenz LLC, http://www.ultraclenz.com, ProGiene System, Weymouth MA.

Kryski, Infection control: Protection through Prevention, Long Term Care, Jun./Jul. 2008, pp. 19-20, vol. 18(2).

Jang et al, Focus group study of hand hygiene practice among healthcare workers in a teaching hospital in Toronto, Infect Control Hosp Epid, Feb. 2010, pp. 144-150, vol. 31(2).

Chagpar, A Human Factors Approach to Hand Hygiene, PowerPoint presentation for the University Health Network, 2008, Toronto.

Bleak et al, An innovative method of measuring and improving hand hygiene adherence using a personal point of care, 2007, California.

Brock, The impact of performance feedback on Handwashing behaviors, Dissertation, The University of Alabama at Birmingham, 2002.

Cagle, The personal responsibility paradigm shift, Nursing and Patient Care, Jul. 2007, pp. 42-48.

Aiello, Casual inference: the case of hygiene and health, AJIC, Dec. 2002, pp. 503-510, vol. 30(8).

MMWR, Guideline for Hand Hygiene in Health-Care Settings: . . . ,Centers for Disease Control, Oct. 25, 2002, vol. 51( No. RR-16), Atlanta, Georgia.

Rebelo, Shea 2009: New Device Monitors Hand-Hygiene Compliance by Healthcare Workers, http://www.medscape.com/viewarticle/589931, Presented Mar. 20, 2009.

CTV News, Device reminds health workers to wash hands, http://www.ctv.ca/servlet/ArticleNews/story/CTVNews/20080303/hand, 2008, Toronto.

Hui and Crowcroft, Bubble Rap: Forwarding in small world DTNs in ever decreasing circles, Technical Report from the University of Cambridge, May 2007, No. 684.

Pittet, Improving Adherence to Hand Hygiene Practice: a Multidisciplinary Approach, Emerging Infectious Diseases, Mar./Apr. 2001, p. 234-240, vol. 7(2).

Haas and Larson, Impact of Wearable Alcohol Gel Dispensers on Hand Hygiene in an Emergency Department, Academic Emergency Medicine, Apr. 2008, pp. 393-396, vol. 15 (4).

Kuttenkuler, Hand Hygiene Monitor Tested at VCU Medical, http://www.news.vcu.edu/news/Hand_Hygiene_Monitor_Tested_at_VCU_Medical_Center, Sep. 16, 2009, VCU Communications.

Priest, After the beep, please record your hand hygiene, http://www.theglobeandmail.com/servlet/story/RTGAM.20080303., Mar. 3, 2008, Toronto, Phillip Crawley, Publisher.

CBC News, Electronic handwashing tool could curb superbug spread, http://www.cbc.ca/health/story/2008/03/03/handwashing-system.html, Mar. 3, 2008, Toronto.

Hotchkiss et al, Pathogen Transmission and Clinic Scheduling, Emerging Infectious Diseases, Jan. 2006, pp. 159-162, vol. 12(1).

Huskins, Interventions to prevent transmission of antimicrobial-resistant bacteria in the intensive care unit, Curr Opin Crit Care, 2007, pp. 572-577, vol. 13.

Larson et al, An organizational climate intervention associated with increased handwashing . . . , Behavioral Medicine, Spring 2000, pp. 14-22, vol. 26(1).

Larson, A tool to assess barriers to adherence to hand hygiene guideline, Am J Infect Control, Feb. 2004, pp. 48-51, vol. 32(1).

Scott, Haggle: Tracing Pocket Switched Networks, Intel Research Cambridge, Powerpoint presentation.

Murphy et al, Building the infection prevention system of tomorrow: Proceedings of the 2007 APIC Futures Summit, AJIC, May 2008, pp. 232-240, vol. 36(4).

Mayhall, C.G., Hospital Epidemiology and Infection Control, 3rd Edition, Chapter 96, by Manfred L. Rotter "Hand washing and hand disinfection", pp. 1727 to 1746 (2004).

Snyder, Hardwiring hand hygiene among staff members, Nursing Management, Feb. 2008, p. 14, vol. 39(2), Publisher:(C) 2008 by Lippincott Williams & Wilkins, Inc.

Joint Commission, Measuring Hand Hygiene Adherence: Overcoming the Challenges, 2009, Consensus Measurement in Hand Hygiene (CMHH) project, Oakbrook Terrace, Illinois.

Inuzuka, Research on healthcare worker behavior to increase hand hygiene . . . ,Poster presentation/publication 9-122, Education and Int'l Conference, Jun. 24, 2008.

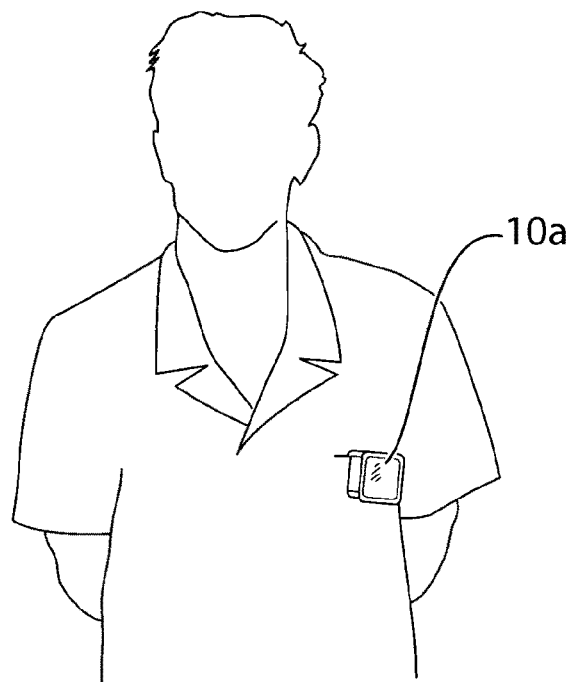
FIG. 6A
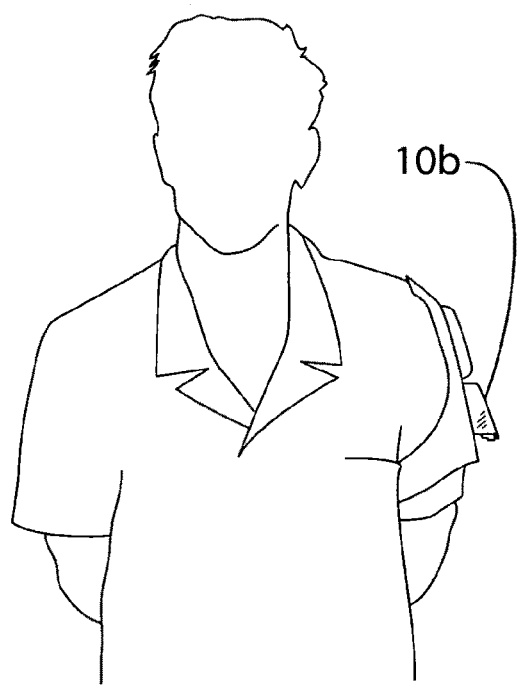 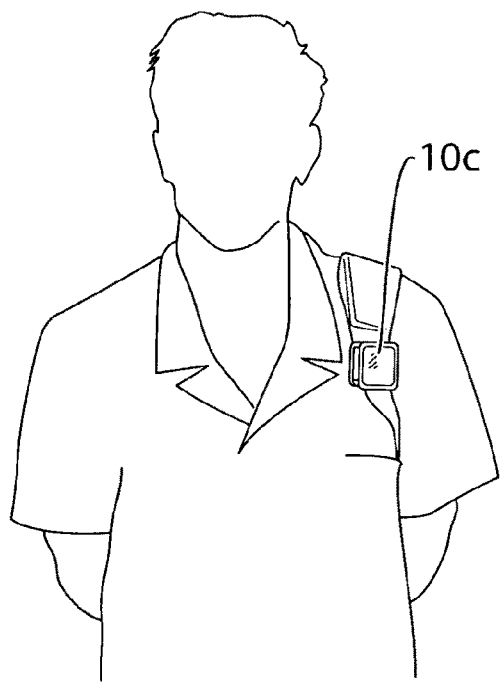
FIG. 6B  FIG. 6C

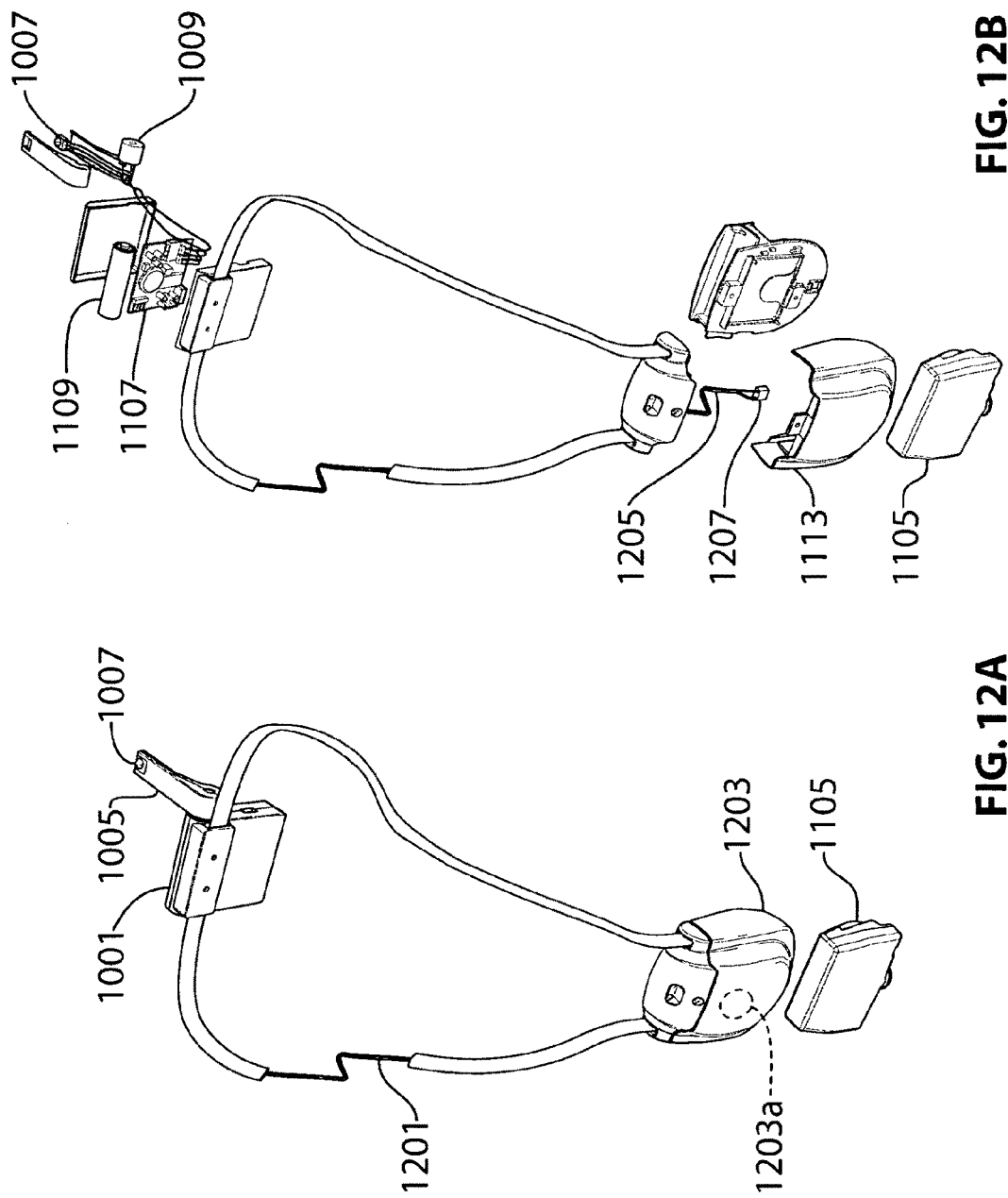

HAND HYGIENE COMPLIANCE SYSTEM

The entire subject matter of U.S. Provisional application 60/920,779 filed Mar. 30, 2007 and entitled HAND HYGIENE COMPLIANCE SYSTEM is incorporated herein by reference. The entire subject matter of U.S. Provisional application 60/960,521 filed Oct. 2, 2007 and entitled HAND HYGIENE COMPLIANCE SYSTEM is also incorporated herein by reference. The entire subject matter of U.S. application Ser. No. 12/078,186 filed Mar. 27, 2008 and entitled HAND HYGIENE COMPLIANCE SYSTEM is also incorporated herein by reference. The entire subject matter of PCT application PCT/CA2008/000534 filed Mar. 27, 2008 and entitled HAND HYGIENE COMPLIANCE SYSTEM is also incorporated herein by reference. The entire subject matter of U.S. application 61/136,720 filed Sep. 29, 2008 and entitled HAND HYGIENE COMPLIANCE SYSTEM is also incorporated herein by reference. Applicant claims priority to each of the above mentioned applications.

This application claims benefit of 61/136,720, filed Sep. 29, 2008 and is a CIP of Ser. No. 12/078,186 filed Mar. 27, 2008, now U.S. Pat. No. 7,898,407, which claims benefit of 60/920,779 filed Mar. 30, 2007 and claims benefit of 60/960,521 filed Oct. 2, 2007 and is a CIP of PCT/CA2008/000534 filed Mar. 27, 2008.

TECHNICAL FIELD

The present invention relates to hand hygiene systems and more specifically to hand hygiene monitoring systems.

BACKGROUND OF THE INVENTION

Approximately one in 10 people admitted to hospitals in the United States acquire a new infection during their stay. These nosocomial infections result in an estimated 100,000 deaths per year in the United States. Nosocomial infections increase the length of patient stays in hospital, contributing to increased healthcare staffing levels, increased costs and increased use of resources. This situation contributes significantly to the overall stress on the healthcare systems and increases wait times. It is estimated that approximately half of these nosocomial infections are the result of inadequate hand hygiene compliance by healthcare staff.

There is considerable evidence that hand hygiene compliance is a primary means to reduce nosocomial infections and the transmission of pathogens. Pathogens are normally present on the skin of healthcare workers and patients and on surfaces surrounding the patient. These organisms can be transferred to healthcare workers' hands where they can survive for periods ranging from minutes to hours. The final step in the transmission process is the transfer of organisms from the contaminated hands of the caregiver to other patients or clean environmental surfaces. Alcohol-based hand rubs seem to be significantly more effective than washing with soap and water and in the reduction of transmission of pathogens.

Wearable dispensers of alcohol-based hand rub can provide ready access hand hygiene without the need to visit a fixed hand washing station and can reduce the time required to perform hand hygiene especially for busy staff such as nurses.

Unfortunately, published studies have generally found that compliance with hand hygiene requirements by healthcare workers averages about 40%. Various traditional educational and management interventions can increase awareness and improve this in the short term but generally do not provide sustainable improvements.

Some prior art systems such as U.S. Pat. No. 5,392,546 to Smith, entitled "Hand Washing Compliance Measurement and Monitoring System" monitor compliance but have several possible disadvantages. A possible disadvantage of the system of Smith is that there is either no prompting of the user when it is necessary to perform hand washing, or the user is prompted every time they enter a zone, irrespective of whether they performed appropriate hand washing or not. Neither scenario would seem to encourage the user or caregiver to improve hand washing compliance. Other possible disadvantages of the system of Smith are interference between site ID transmitters between closely spaced sites and lack of a method to prompt users to wash their hands after extended periods of time within the same zone.

Accordingly, an improved system and method to encourage increased hand hygiene compliance in environments where the transfer of pathogens can be dangerous, remains highly desirable.

SUMMARY OF THE INVENTION

It is therefore an object of the present invention to provide an improved system and method to encourage increased hand hygiene compliance by increased convenience and appropriate prompting when needed.

Accordingly, an aspect of the present invention provides a method of encouraging compliance of hand hygiene in a system having a disinfectant dispenser, a dispensing detector, a wearable zone sensor, a controller, a timer means and an alerting means. The method comprises steps of detecting a change of zone of the wearable zone sensor; responsive to detecting a change of zone, starting a preset first timer; and responsive to expiration of the first timer, activating the alerting means.

Another aspect of the present invention provides a method of encouraging compliance of hand hygiene in a system having a disinfectant dispenser, a dispensing detector, a wearable zone sensor, a controller, a timer means and an alerting (prompting) means. The method comprises a system for precisely defining zones around different patients, entrance ways, equipment and other specific areas where hand cleansing is needed. The method also comprises steps of starting a timer when the hand hygiene system is used; prompting for hand cleansing if the timer has expired when entering a zone; detecting the entry of a wearable zone sensor moving into a defined zone; and prompting for hand cleansing when entering a new patient zone or when leaving the room through a zone marking the entrance or leaving the bathroom.

Some embodiments further comprise a step of disabling the first timer responsive to sensing dispensing of disinfectant.

In some embodiments, the step of detecting a change of zone further comprises steps of: sensing a zone identifier signal; decoding a first zone identifier from the zone identifier signal; comparing the first zone identifier with a stored zone identifier; determining a change of zone if said first zone identifier differs from said stored zone identifier; and storing said first zone identifier as the stored zone identifier.

Some embodiments further comprise a step of logging the time associated with detecting a change of zone.

Some embodiments further comprise a step of logging the time associated with activating the alerting means.

Some embodiments further comprise a step of logging said first zone identifier associated with detecting a change of zone.

Some embodiments further comprise a step of transmitting said zone identifier signal from a zone transmitter.

In some embodiments, the step of transmitting comprises transmitting an ultrasonic signal.

In some embodiments, the step of transmitting comprises transmitting a radio frequency signal.

In some embodiments, the step of transmitting comprises transmitting an infrared signal.

In some embodiments, the step of transmitting comprises transmitting an infrared signal from an array of one or more infrared emitters.

In some embodiments, the step of transmitting comprises transmitting said infrared signal within a zone defined by a radiation pattern of each of said infrared emitters.

In some embodiments, the disinfectant dispenser is integrated with said wearable zone detector, the method further comprising sensing dispensing of disinfectant by way of a contact closure.

In some embodiments, the disinfectant dispenser is separate from the wearable zone detector, the method further comprising steps of at said disinfectant dispenser, transmitting an indication of dispensing of disinfectant to said wearable zone detector, and at said wearable zone detector, receiving said indication of dispensing.

In some embodiments, the transmitting of said indication of dispensing of disinfectant is performed wirelessly.

In some embodiments, the wireless transmitting of said indication of dispensing of disinfectant uses radio frequency, infrared or visible spectrum radiation, such as by the use of light emitting diodes (LED's) or the like.

In some embodiments, the receiving of said indication of dispensing, is performed by the infrared sensor of said zone sensor.

In some embodiments, the indication of dispensing is an infrared signal distinguishable from said zone identifier signals.

A further aspect of the present invention provides a system for encouraging compliance of hand hygiene. The system comprises: a disinfectant dispenser; a dispensing detector configured to detect operation of said disinfectant dispenser; a controller in communication with said dispensing detector; a wearable zone sensor in communication with said controller; an alerting device in communication with said controller; and a zone identification transmitter configured to transmit a zone identification capable of detection by said zone sensor when said zone sensor is within a predefined proximity to said zone identification transmitter, wherein said system is configured to activate said alerting means responsive to said dispensing detector not sensing operation of said disinfectant dispenser within a first predefined time delay of said wearable zone sensor detecting a change of zone.

In some embodiments, the system is configured to disable said alerting device responsive to said dispensing detector sensing operation of said disinfectant dispenser.

In some embodiments, the disinfectant dispenser is integral with said wearable zone sensor.

In some embodiments, the disinfectant dispenser is separate from said wearable zone sensor.

In some embodiments, the disinfectant dispenser is mounted in a substantially fixed location and said dispensing detector is configured to transmit indication of operation of said disinfectant dispenser, wirelessly to said controller.

Some embodiments further comprise a data memory in communication with said controller, wherein said controller is configured to log into said data memory, a zone identifier for a current zone associated with said change of zone.

In some embodiments, the controller is configured to log into said data memory, a zone-change time associated with said change of zone, responsive to said change of zone.

In some embodiments, the controller is configured to log into said data memory, a disinfectant dispenser operation time, responsive to sensing operation of said disinfectant dispenser.

Some embodiments further comprise a plurality of zone identification transmitters, each configured to transmit a unique zone identification.

In some embodiments, the zone identification transmitter is configured to communicate with said wearable zone sensor via a wireless signal.

In some embodiments, the wireless signal is an infrared signal.

In some embodiments, each zone identification transmitter comprises an array of one or more infrared emitters.

In some embodiments, each infrared emitter is configured to emit radiation in a predefined zone.

In some embodiments, the predefined zone is determined by a shield on or around the IR transmitter having a predefined shape.

In some embodiments, the predefined shape is conical.

In some embodiments, the predefined shape is a fraction of a cone.

In some embodiments, the wireless signal is an ultrasonic signal.

In some embodiments, the wireless signal is a radio frequency signal.

Some embodiments further comprise a communication interface configured to interface with a central computer to permit transfer of said logged information from said data memory to said central computer, and wherein said central computer is configured to process said downloaded data to provide indications of hand hygiene compliance.

Some embodiments further comprise a docking station comprising a plurality of said communication interfaces configured to accommodate a plurality of wearable zone sensors.

In some embodiments, the system is configured to permit anonymous check out and check in of said wearable zone sensors, wherein each said wearable zone sensor comprises a unique identifier.

In some embodiments, the processed downloaded data is retrievable anonymously using said unique zone sensor identifier.

In some embodiments, the processed data for a predefined group of zone sensors is retrievable collectively.

In some embodiments, the system is configured to permit check out and check in of said wearable zone sensors using a user identifier and wherein said system logs said user identifier.

In some embodiments, the system logs said user identifier in said data memory.

In some embodiments, the first predefined time delay is a function of zone type as determined from said zone identification.

In some embodiments, the zone identification comprises a unique number and wherein said zone identification transmitter is configured to transmit said zone identification as a coded sequence of pulses.

In some embodiments, the coded sequence of pulses comprises an integrity check.

In some embodiments, the zone identification transmitter is configured to adapt the output level of said transmitted coded pulses responsive to an ambient radiation level.

In some embodiments, the alerting device is configured to provide an audible signal.

In some embodiments, the alerting device is configured to provide a vibrating signal.

In some embodiments, the alerting device is configured to provide a visual signal, or one or more signals including visual, vibratory; auditory and the like.

In some embodiments, responsive to connection of the communication interface, the controller initiates downloading of the logged information.

In some embodiments, responsive to hand wash dispenser action, the controller resets a first preset timer; resets a second preset timer; resets a third preset timer; and disables alert if active.

In one aspect of the invention, a wearable tag or device is worn by a caregiver or other user in a hospital or other care facility. The wearable tag can detect and log when the caregiver enters or passes through predefined zones and can log when the caregiver sanitizes his hands by detecting activation of a dispensing unit. The dispensing units can be integral to the wearable unit or alternatively can be fixed dispensing units in which case the dispensing unit can transmit indication of the activation of the dispensing unit. In one preferred embodiment, the zones are defined by arrays of infrared (IR) transmitters. The arrays comprise one or more IR emitters with associated collimators/lenses/shields to clearly define a zone. The IR emitters in each zone are controlled by a zone transmitter which modulates the output of the emitters to produce a unique zone identifier.

In some embodiments the step of starting a first timer is responsive to sensing dispensing of disinfectant.

In some embodiments, responsive to connection of a data interface, the controller initiates down load of data to a central computer.

In some embodiments, responsive to disinfectant dispensing action, the controller resets a first preset timer; reset a second present timer; and resets a third preset timer; and disables the alerting device if active.

Another aspect of the present invention provides a wearable smart zone sensor configured to be worn by a user. The smart zone sensor comprises: a zone detector configured to detect a wireless zone identifier signal; a controller in communication with said zone detector; a data memory in communication with said controller; a dispenser activation detector in communication with said controller; and an alerting device in communication with said controller for alerting the user, wherein the controller is configured to: decode a zone identifier from said zone identifier signal; determine when said smart zone sensor enters a zone responsive to said zone identifier signal and store said zone identifier and time of entering in said data memory; determine when said smart zone sensor leaves a zone responsive to said zone identifier signal and store said zone identifier and time of leaving in said data memory; determine when dispenser activation occurs responsive to said dispenser activation detector and store time of dispenser activation in said data memory; and alert said user when a hand cleansing operation is required.

Some embodiments further comprise an interface for transmitting to an external computer, the data stored in said data memory.

Some embodiments further comprise a housing configured as a user identification card.

Some embodiments further comprise a dispenser for hand cleansing product wherein said dispenser activation detector is configured to detect dispensing of said hand cleaning product.

In some embodiments, the dispenser is collocated in said housing with said smart zone sensor.

Some embodiments further comprise a housing for enclosing said smart zone sensor, wherein said housing is configured for attachment to a lanyard.

Some embodiments further comprise an arm pivotally connected to said housing, wherein said arm houses said zone detector and is configured to maintain said zone detector in spaced relationship from said user when said arm is in an operating position and wherein said arm can be pivoted to a storage position.

In some embodiments the zone detector comprises an infrared (IR) sensor.

In some embodiments the dispenser activation detector is configured to receive a wireless signal from a fixed dispenser unit.

In some embodiments the dispenser activation detector is configured to receive an IR signal from said fixed dispenser unit.

In some embodiments the dispenser activation detector is configured to receive a wireless signal from a portable dispenser unit.

In some embodiments the dispenser activation detector is configured to receive a radio frequency (RF) signal from said portable dispenser unit.

In some embodiments the dispenser activation detector is configured for wired communication with a portable dispenser unit, said portable dispenser unit configured for mounting on said lanyard.

Yet another aspect of the present invention provides a fixed dispenser unit for dispensing a hand cleansing product. The fixed dispenser unit comprises: a cleansing product container; a cleansing product dispenser for dispensing said cleansing product from said container; a wireless zone identifier signal transmitter for transmitting a signal indicative of a dispenser activation and zone identifier for receipt by a smart zone sensor; a controller for encoding said zone identifier signal.

In some embodiments, the fixed dispenser unit is configured for mounting on a wall.

In some embodiments, the fixed dispenser unit is configured for mounting on a pylon.

Some embodiments further comprise a proximity sensor for sensing proximity of a user's hands to said dispenser and wherein said controller is further configured to activate said cleansing product dispenser responsive to said proximity sensor sensing a user's hands.

In some embodiments, the fixed dispenser unit is configured for dispensing a viscous product.

In some embodiments, the cleansing product dispenser comprises a pump.

In some embodiments, the wireless zone identifier signal transmitter comprises an infrared emitter.

In another aspect, there is provided a wearable monitoring unit, which comprises:
  a. a data transfer portion operable for receiving sensory data reporting a hygiene event from a hygiene detector, and zone data from a zone beacon, the zone data including zone location data and/or zone type data;
  b. a memory portion including:
    i. a first memory segment to store the sensory data;
    ii. a second memory segment to store a group of hygiene status subroutines, each according to a corresponding infection risk level;
  c. a processor module configured to:
    1. receive at least one zone data message from the zone beacon;
    2. decode the zone data message to identify a zone location data portion and/or the zone type data portion;
    3. select a hygiene status subroutine according to a zone type data portion and the infection risk level, or a correlation therebetween;
    4. execute the selected hygiene status subroutine.

In some embodiments, the first subroutine includes an instruction to issue an alert signal. The monitoring unit comprises a user alert portion for issuing one or more hygiene alert signals for an active attendant, wearing the monitoring unit, to carry out a hygiene event. The user alert portion is responsive to the processor module to issue the alert signal.

In some embodiments, the user alert portion is operable to issue two or more different hygiene alert signals, the instruction including issuing a first of the hygiene alert signals.

Some embodiments further comprise a user alert portion for issuing one or more hygiene alert signals for an active attendant, wearing the monitoring unit, to carry out a hygiene event, selected ones of the subroutines including instructions to issue a hygiene alert message, the user alert portion responsive to the hygiene alert message for issuing one or more hygiene alert signals to the user.

In another aspect, there is provided a wearable monitoring unit comprising a data transfer portion operable for receiving sensory data reporting a hygiene event from a hygiene detector, and zone data from a zone beacon, the zone data including zone location data and/or zone type data. A user alert portion is provided for issuing one or more hygiene alert signals for an active attendant, wearing the monitoring unit, to carry out a hygiene event. A memory portion is also provided, including a first memory segment to store the sensory data, a second memory segment to store a group of hygiene status subroutines, each according to a corresponding infection risk level, a third memory segment to store zone location data for a plurality of predetermined zone locations and/or zone type data for a plurality of predetermined zone types; and a fourth memory segment to index correlations between each of the hygiene status subroutines and one or more of the predetermined zone locations and/or one or more of the predetermined zone types. Also provided is a processor module which is configured to receive at least one zone data message from the zone beacon, decode the zone data message to identify the zone location data portion and/or the zone type data portion; select a hygiene status subroutine according to an indexed correlation with the zone identify data portion and/or the first zone type data portion; and execute the selected hygiene status subroutine.

In another aspect, there is provided a wearable monitoring unit. The wearable mounting unit comprises a data transfer portion operable in a first phase for receiving sensory data reporting a hygiene event from a hygiene detector, and zone data from a zone beacon, the zone data including zone location data and/or zone type data. The data transfer portion is operable in a second phase for transferring user identity data and/or activity history data between the monitoring unit and an external station. A memory portion is provided which includes a first memory segment to store the sensory data, a second memory segment to store a group of hygiene status subroutines, each according to a corresponding infection risk level, a third memory segment to store zone location data for a plurality of predetermined zone locations and/or zone type data for a plurality of predetermined zone types, a fourth memory module to index correlations between each of the hygiene status subroutines and one or more of the predetermined zone locations and/or one or more of the predetermined zone types, and a fifth memory segment to store the activity history data. A processor module is also provided and is configured to receive at least one first zone data message from a first zone beacon, decode the first zone data message to identify a first zone location data portion and/or the first zone type data portion, select a first hygiene status subroutine according to an indexed correlation with the first zone location data portion and/or the first zone type data portion; and execute the first subroutine.

Some embodiments further comprise a user alert portion for issuing one or more hygiene alert signals for an active attendant, wearing the monitoring unit, to carry out a hygiene event. The first subroutine, in this case, includes an instruction to issue an alert signal. The user alert portion is responsive to the processor module to issue the alert signal.

In some embodiments, the user alert portion is operable to issue two or more different hygiene alert signals. In this case, the instruction includes issuing a first of the hygiene alert signals.

In some embodiments, the processor module is configured to receive at least one second zone data message from a second zone beacon, decode the second zone data message to identify a second zone location data portion and/or a second zone type data portion, select a second hygiene status subroutine according to an indexed correlation with the second zone location data portion and/or the second zone type data portion, and execute the second subroutine.

In some embodiments, the second subroutine includes an instruction to issue a second alert signal which is different from the first alert signal. The user alert portion, in this case, is responsive to the processor module to issue the second alert signal.

In some embodiments, the second subroutine has a lower infection risk level than the first subroutine. The lower risk level is one not requiring an alert signal and the user alert portion is not operable to issue a second signal as a result of the second subroutine.

In another aspect, there is provided a system for monitoring hand hygiene among a number of human attendants in a facility. The system includes a number of wearable monitoring devices, each to be worn by an active attendant. Each monitoring device includes a data transfer portion operable in a first phase for receiving sensory data reporting a hygiene event from a hygiene detector, and zone data from a zone beacon, the zone data including zone location data and/or zone type data. The data transfer portion is operable in a second phase for transferring user identity data and/or activity history data between the monitoring device and an external station. A user alert portion is provided and configured for issuing one or more hygiene alert signals for alerting the active attendant. A memory portion is also provided and configured to store the sensory data, store a group of hygiene status subroutines, each according to a corresponding infection risk level, store a listing of predetermined zone locations and/or a list of predetermined zone types, store a listing of associations between each hygiene status subroutine and at least one predetermined zone location and/or at least one predetermined zone type, and store the activity history data. Also provided is a monitoring processor module configured to receive at least one zone data message from a zone beacon, decode the zone data message to identify a zone location data portion and/or a zone type data portion, select an association according to the zone location data portion and/or the zone type data portion, select a hygiene status subroutine according to the association, and execute the first subroutine.

In some embodiments, selected ones of the subroutines includes instructions to issue a hygiene alert message. The user alert portion is responsive to the hygiene alert message for issuing one or more hygiene alert signals to the user.

In some embodiments, the number of wearable monitoring devices include a first group of wearable monitoring devices for a first group of human attendants. The memory portion in each of the first group of wearable monitoring devices is operable to store a first group of hygiene status subroutines and unique to the first group. A second group of wearable monitoring devices is also provided for a second group of human attendants. The memory portion in each of the second group of wearable monitoring devices is operable to store a second group of hygiene status subroutines and unique to the second group.

In another aspect, there is provided a wearable monitor unit for a hand hygiene monitoring system, wearable by an attendant in a facility. The wearable monitor unit comprises a data transfer portion operable for receiving sensory data of one or more descriptors of activity of the attendant wearing the monitoring unit. A monitor processor module is provided and configured to receive sensory data recording a number of repeated instances of a first current attendant activity, to generate a first series of current activity feature data sets for the first current attendant activity, generate a feature space data structure modeling the first series, receive sensory data recording a number of repeated instances of a second current activity, to generate a second series of current activity feature data sets for the second current attendant activity, generate a feature space data structure modeling the second series; and associate each data structure with a corresponding hygiene risk level to form a number of associations. A memory portion is provided and configured to store the feature space data structures for the first and second series and the associations.

In some embodiments, the memory portion is configured to store a list of hygiene status subroutines, each according to a corresponding infection risk level.

In some embodiments, the sensory data is processed or unprocessed sensory data.

In another aspect, there is provided a system for monitoring hand hygiene among a number of human attendants in a facility, comprising a number of wearable monitor units, each monitoring unit to be worn by one attendant. Each monitoring unit includes data transfer portion operable in a first phase for receiving sensory data reporting a hygiene event, sensory data of one or more descriptors of activity of the attendant wearing the monitoring unit and zone data. The zone data includes zone location data and/or zone type data. The data transfer portion is operable in a second phase for transferring user identity data and/or activity history data between the monitoring unit and an external station. Also provided is a memory portion which is configured to store a plurality of feature space data structures, each for a predicted attendant activity, store a list of hygiene status subroutines, each according to a corresponding infection risk level and the activity history data. A monitor processor module is provided and configured to receive the sensory data to generate at least one current activity feature data set for a current attendant activity, associate the current activity feature data set with the feature space data structures to generate a correlation between the feature data set and one of the feature space data structures, select an infection risk level according to the correlation, select a hygiene status subroutine from the list of hygiene status subroutines according to the infection risk level, and execute the selected hygiene status subroutine.

In some embodiments, each monitoring unit further comprises an alerting portion for issuing one or more hygiene alert signals for the attendant to carry out a hygiene event. In this case, the selected hygiene subroutine includes an instruction to the alerting portion for issuing one or more hygiene alert signals.

In some embodiments, the monitor processor module is configured to form a group of identities for a corresponding number of successive current attendant activities, store the identities, predict a next attendant activity based on the stored identities, select an infection risk level according to the next attendant activity; and carry out a corresponding hygiene status subroutine in advance of the next attendant activity based on the selected infection risk level.

In some embodiments, the monitor processor configured to issue a hygiene alert signal according to the hygiene status subroutine.

In some embodiments, the data transfer portion is operable to receive the sensory data reporting a hygiene event, in the form of a signal from a dispenser worn by the attendant or from a dispenser not worn by the attendant.

Some embodiments further comprise a dispenser which is operable for issuing a signal to the data transfer portion, with the signal carrying the sensory data reporting a hygiene event.

In some embodiments, the dispenser is worn by the attendant wearing the monitoring unit.

Some embodiments further comprise one or more sensors for issuing a signal to the data transfer portion. Each signal carries the sensory data of one or more descriptors of activity of the attendant wearing the monitoring unit.

In some embodiments, the sensors include an accelerometer, thermometer, microphone, elevation meter, pressure meter, motion sensor, global positioning device, gyroscope, blood pressure monitor, heart rate monitor, muscle activity monitor (electromyographic (EMG) sensors, Mechanomyographic (MMG) sensors), skin conductance sensor.

In some embodiments, one or more of the sensors include a sensor processor configured to generate one or more predetermined feature coordinates.

In some embodiments, the monitor processor is configure to generate the feature data set according to the one or more feature coordinates.

In some embodiments, the hygiene event includes a hand wash disinfectant activation.

In some embodiments, the hygiene event includes a hand wash sink activation, a soap dispenser activation, a towel activation, a glove dispenser activation and/or blower activation.

In some embodiments, one or more of the sensors are configured to measure one or more signals of the attendant activity, including linear acceleration, angular acceleration, temperature, air pressure, and/or sound as well as physiological signals such as heart rate, blood pressure, muscle activity, skin conductance of the attendant.

In some embodiments, the monitor processor employs one or more pattern recognition subroutines to generate the correlation.

In some embodiments, one or more of the sensors measures angular or linear acceleration, speed, and/or distance the feature coordinates including mean, standard deviation, energy and/or axis correlation.

In some embodiments, one or more of the feature coordinates include one or more time domain features coordinates, including root mean square (RMS), integrated RMS, mean absolute value (MAV), mean absolute value slope (MAVSLP), zero crossing (ZC), waveform length, variance, number of slope sign changes and/or amplitude histograms.

In some embodiments, one or more of the feature coordinates include one or more frequency domain features coordinates including spectral representations of the signal, the spectral representations including Fast Fourier Transform (FFT) coefficients, autoregressive (AR) coefficients, and/or cepstral coefficients.

In some embodiments, one of the feature coordinates include one or more time-frequency features including short-time Fourier transform (STFT) coefficients, wavelet coefficients and wavelet packet coefficients.

In some embodiments, the monitor processor is responsive to the sensor processors to receive a plurality of feature coordinates therefrom and to generate the feature data set.

In some embodiments, the monitor processor is further configured to employ a dimensionality reduction subroutine to reduce the number of feature coordinates in the plurality of received feature coordinates in the generated feature data set.

In some embodiments, for the step to associate, the monitor processor is configured to employ a supervised and/or an unsupervised classification subroutine, including Linear classifiers such as Linear Discriminant Analysis, Decision Tables, Decision Trees (C4.5), k-Nearest Neighbor, Support Vector Machines (SVM), Hidden Markov Models, Artificial Neural Networks, Fuzzy and neuro fuzzy classifier, and Clustering.

In some embodiments, for the step to associate, the monitor processor is configured to employ a majority vote subroutine to resolve conflicts between a current feature data set and a corresponding feature space data structure.

In yet another aspect, there is provided a system for monitoring hand hygiene among a number of human attendants in a facility, comprising a number of wearable monitor units. Each monitoring unit includes a data transfer portion operable in a first phase for receiving sensory data reporting a hygiene event, sensory data of one or more descriptors of activity of the attendant wearing the monitoring unit, as well as zone data, in which the zone data includes zone location data and/or zone type data. The data transfer portion is operable in a second phase for transferring user identity data and/or activity history data between the monitoring unit and an external station. An alerting portion is provided for issuing one or more hygiene alert signals for the attendant to carry out a hygiene event. A memory portion is provided and configured to store a plurality of vector space values for a predicted attendant activity; store a list of hygiene status subroutines, each according to a corresponding infection risk level; and the activity history data. A monitor processor module is provided and configured to receive the sensory data to assemble at least one current activity vector value for a current attendant activity, associate the current activity vector value with the vector space values to generate a correlation between the current activity vector value and one of the vector space values, select an infection risk level according to the correlation, select an alert subroutine from the list of hygiene status subroutines according to the infection risk level, and execute the selected hygiene subroutine.

In another aspect, there is provided a system for monitoring hygiene compliance, comprising a plurality of zone sensors for issuing zone data and a plurality of wearable monitoring devices. Each wearable monitoring device comprises a data transfer portion operable for receiving sensory data reporting a hygiene event from a hygiene detector, and zone data from a zone beacon, in which case the zone data includes zone location data and/or zone type data. A memory portion is also provided which includes first memory segment to store the sensory data a second memory segment to store a group of hygiene status subroutines, each according to a corresponding infection risk level. A processor module is provided which is configured to receive at least one zone data message from the zone beacon, decode the zone data message to identify a zone location data portion and/or the zone type data portion, select a hygiene status subroutine according to a zone type data portion and the infection risk level, or a correlation therebetween, and execute the selected hygiene status subroutine.

In some embodiments, the plurality of wearable monitoring devices includes a first group of wearable monitoring devices for a first group of human attendants. The memory portion in each of the first group of wearable monitoring devices is operable to store a first group of hygiene status subroutines and unique to the first group. A second group of wearable monitoring devices is also provided for a second group of human attendants. The memory portion in each of the second group of wearable monitoring devices is operable to store a second group of hygiene status subroutines and unique to the second group.

BRIEF DESCRIPTION OF THE DRAWINGS

Further features and advantages of the present invention will become apparent from the following detailed description, taken in combination with the appended drawings, in which:

FIG. 6A, 6B, 6C illustrate various locations for wearing an embodiment of a wearable smart handwash dispenser;

FIGS. 12A and 12B illustrate a perspective view and a break-away perspective view respectively, of a lanyard—wearable dispenser embodiment of the present invention;

It will be noted that, throughout the appended drawings, like features are identified by like reference numerals.

DETAILED DESCRIPTION OF THE PREFERRED EMBODIMENT

Figures 1A, 1B:
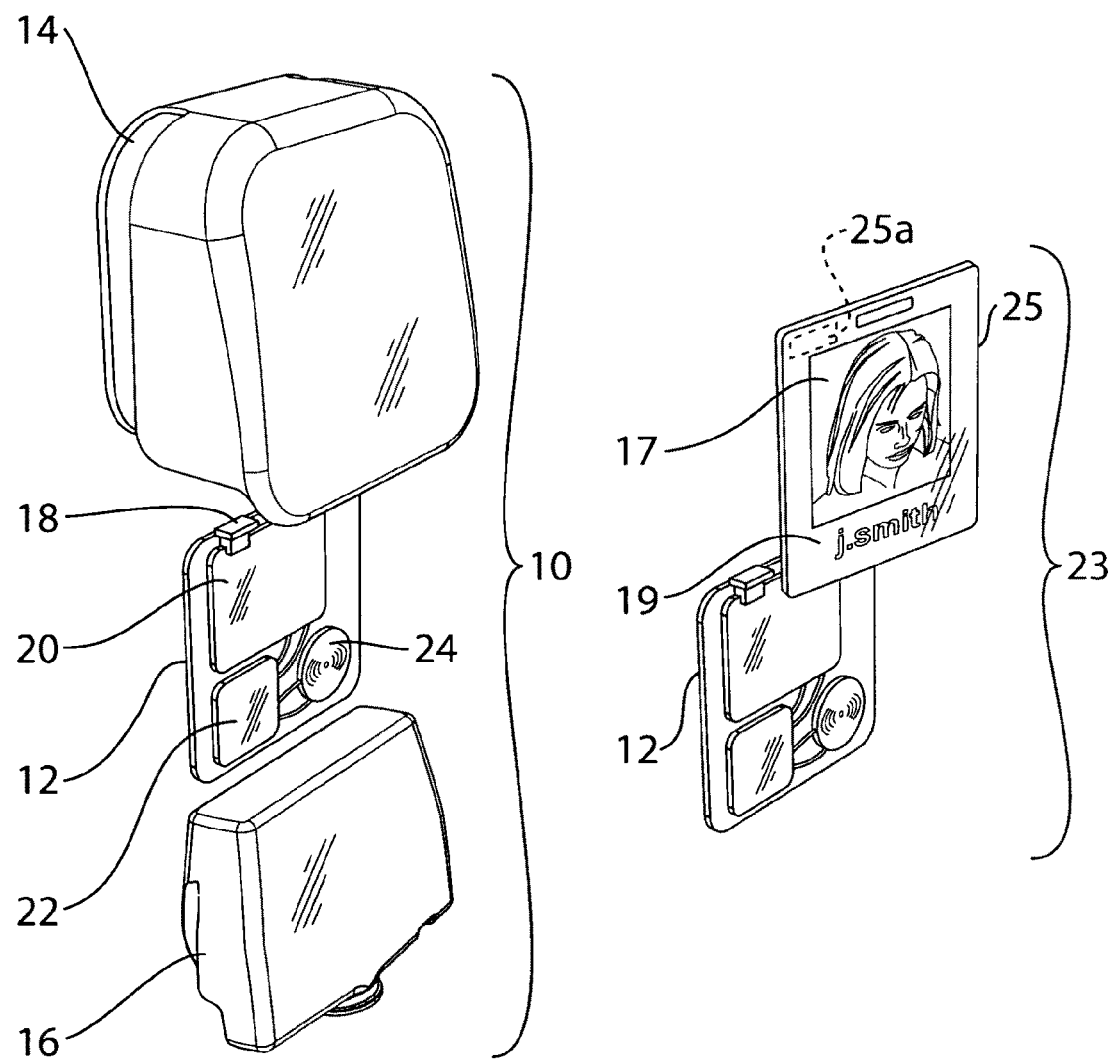
FIG. 1A is a breakaway perspective illustration showing an embodiment of a smart zone sensor incorporating a wearable handwash dispenser of the present invention.
FIG. 1B is a breakaway perspective illustration showing another embodiment of a wearable smart zone sensor of the present invention.

It should be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Furthermore, and as described in subsequent paragraphs, the specific mechanical configurations illustrated in the drawings are intended to exemplify embodiments of the invention. However, other alternative mechanical configurations are possible which are considered to be within the teachings of the instant disclosure. Furthermore, unless otherwise indicated, the term "or" is to be considered inclusive.

Various embodiments of the present invention will now be described with reference to the figures. FIG. 1A shows a breakaway perspective illustration of a wearable smart disinfectant dispenser assembly 10. The assembly comprises a smart zone sensor 12 which fits in external housing 14, along with dispenser cartridge 16. The dispenser cartridge 16 is a disposable cartridge for dispensing a hand sanitizing lotion or gel such as alcohol based sanitizing gels well known in the art. The gel is dispensed by squeezing a resilient side wall of the cartridge 16 against external housing 14. The cartridge 16 can be easily replaced as needed. In other embodiments, the cartridge 16 is refillable and reusable. The zone sensor 12 has a signal detector 18, a control circuit 20, a dispensing sensor 22, and an alerting device 24. The detector 18 will be discussed in its exemplified form as an infrared detector 18, though it may also be operable to receive signals of other forms, such as ultrasonic signals. The infrared detector 18 can be an intelligent infrared detector integrated circuit as is well known in the art. The control circuit uses a microprocessor with a real-time clock or other suitable controller. The control circuit 20 is connected to infrared detector 18 which is visible external to the external housing 14 so that the infrared detector 18 can receive infrared signals from among a plurality of zone transmitters 26 (see FIGS. 2, 7, 8) which can be set up in a hospital, or other caregiver environments or food handling environment where hand hygiene might be important to counteract cross contamination. The control circuit 20 is connected to dispensing sensor 22, which is shown here as a pressure sensitive switch which is positioned so as to be able to sense the dispensing action of the cartridge when it is operated by the user. The alerting device 24 can be an audible buzzer or sound generating device or a visual indicator such as a lamp or light emitting diode (LED) or a vibrator to provide an alerting signal to the user without unduly distracting patients or attracting attention, or a combination thereof. The control circuit 20 has a data memory 21 (see FIG. 2) for collecting or logging data.

The assembly 10 is operable in a communication network which, in this example, is computer implemented and may be provided in a number of forms, by way of one or more software programs configured to run on one or more general purpose computers, such as a personal computer, or on a single custom built computer, such as programmed logic controller (PLC) which is dedicated to the function of the system alone. A system controlling such a communication network may, alternatively, be executed on a more substantial computer mainframe. The general purpose computer may work within a network involving several general purpose computers, for example those sold under the trade names APPLE or IBM, or clones thereof, which are programmed with operating systems known by the trade names WINDOWS, LINUX or other well known or lesser known equivalents of these. The system may involve pre-programmed software using a number of possible languages or a custom designed version of a programming software. The computer network may be include a wired local area network, or a wide area network such as the Internet, or a combination of the two, with or without added security, authentication protocols, or under "peer-to-peer" or "client-server" or other networking architectures. The network may also be a wireless network or a combination of wired and wireless networks. The wireless network may operate under frequencies such as those dubbed 'radio frequency' or "RF" using protocols such as the 802.11, TCP/IP, BLUE TOOTH and the like, or other well known Internet, wireless, satellite or cell packet protocols. While the assembly 10 collects location data from zone transmitters 26, the assembly may have the ability to determine its location within the facility by use of other locating methods, such as by global positioning system (GPS) protocols or variants or analogs thereof.

Figure 3:
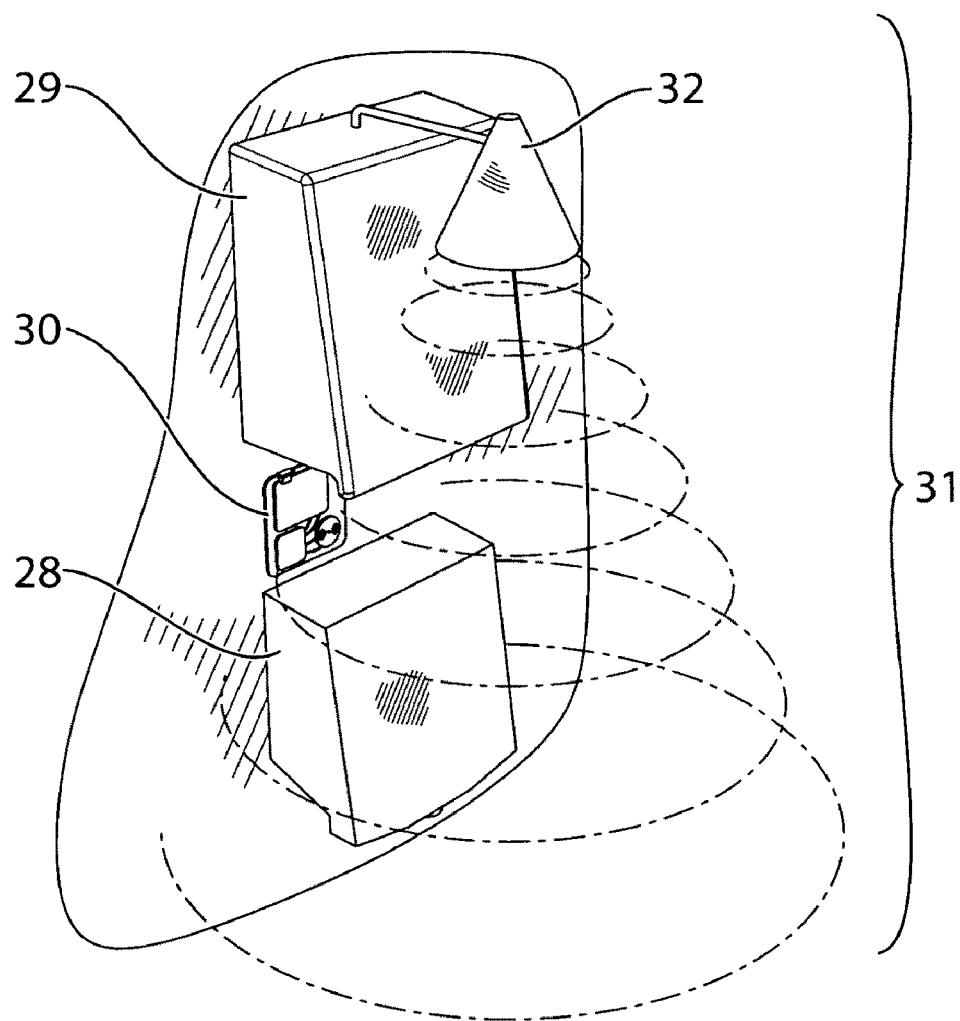
FIG. 3 is a breakaway perspective illustration showing embodiment of a fixed handwash dispenser of the present invention.

In another embodiment, the smart zone sensor 12 can be used independently of the wearable dispenser assembly 10. FIG. 1B illustrates a breakaway perspective view showing a wearable smart zone sensor assembly 23 wherein a wearable housing 25 is configured to accept insertion of smart zone sensor 12 and further configured to accept a clip or lanyard or other suitable attachment means to allow a caregiver or other user to wear the assembly 23. In this embodiment, the wearable smart zone sensor can operate in cooperation with a fixed or wall-mounted disinfectant dispenser 31 as shown in FIG. 3. The wearable smart zone sensor assembly 23 is configured to accept a wireless signal indicating a hand sanitizing operation from an external disinfectant dispenser such as the fixed disinfectant dispenser 31. The wireless signal can be, for example, one or more of a radio frequency signal, an ultrasonic signal, a visible spectrum radiation signal or, as in this particular case, an infrared signal using the infrared detector 18.

The wearable smart zone sensor assembly 23 can be configured as an anonymous device, with a device identifier discreetly incorporated such that a user can readily determine the identity of the unit for later data tracking, but the device identifier is not easily visible to other people when it is worn by the user. Alternatively, the wearable housing 25 can be combined with a user identification badge, displaying the user's name 19 and/or photo 17 or other indicia as appropriate to the working environment. The wearable housing 25 can also incorporate magnetic stripes, bar codes or RFID tags, as is well known in the field of user identification badges.

In general, the smart wearable disinfectant dispenser assembly 10, can detect zones that a user enters, such as can be defined around individual patient beds, hospital rooms or patient treatment areas, and can record or log the time of entering and leaving such zones as well as log the zone identifier. Thus, the assembly 10 is operable to detect a change of zone, that is when the user moves from one zone to another. The time of hand sanitizing as determined by activation of the disinfectant dispenser can also be logged.

The alerting device 24 can provide prompting to the user if he/she forgets to sanitize his/her hands when appropriate. If the user sanitizes his/her hands at appropriate times, then the alerting signal is not required and the user can avoid the annoyance of the alerting signal. This feedback can provide a training or conditioning function which can help increase hand hygiene compliance among users. Another feedback mechanism can be reviewing a daily log of hand sanitizing activity correlated with a log of a user's movement between zones. The wearable device of the present invention can be associated with a user identifier or alternatively, can be used anonymously. The user can benefit from the prompting actions of the device and can also review the activity log anonymously by merely accessing logged data associated with an identifier of the device used by the user.

Figure 2A:
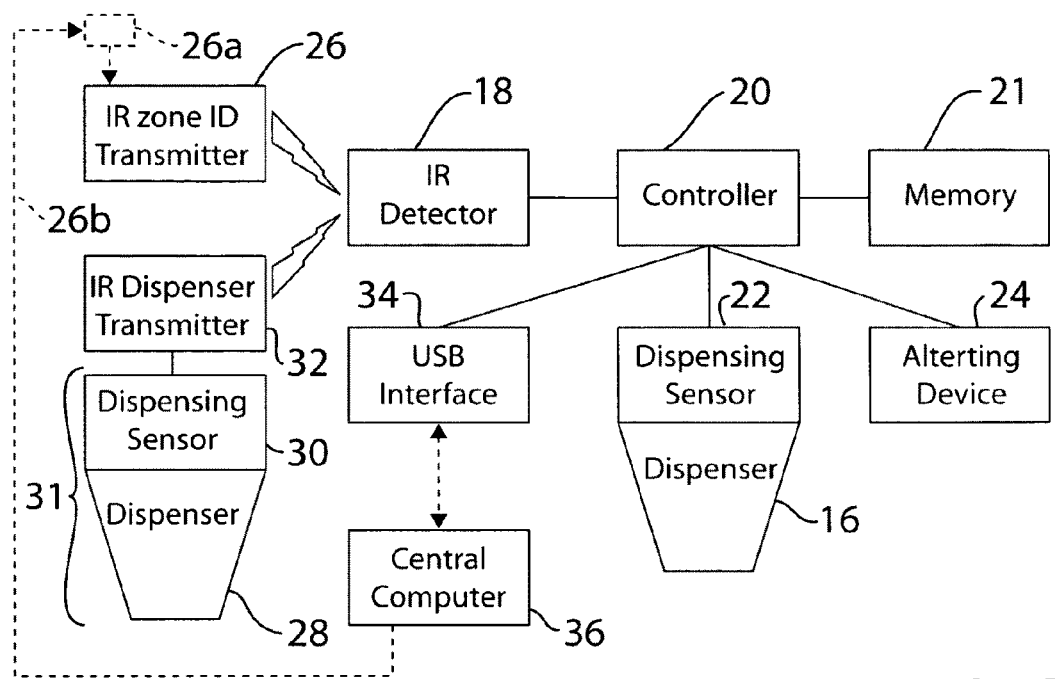
FIG. 2A is a block diagram illustrating a wearable smart handwash dispenser in a system of the present invention.

FIG. 2A is a block diagram illustrating the smart wearable disinfectant dispenser assembly 10 of FIG. 1, in a system of the present invention. Controller 20 has data memory 21 for logging data such as time of dispenser activations, and of entering and leaving zones. The data memory 21 is an EEPROM for non-volatile storage of data although other type of data memory known in the art could be used as an alternative. The data memory 21 can store an identifier code unique to each individual unit, a record or log of the identity of each zone visited and the time of entering and leaving each zone, and a log of the time of dispensing actions or hand hygiene activity history. This data is stored for later downloading to a central computer for later analysis. Temporary data such as hand disinfection status "flags" of the caregiver (clean or dirty) will be stored in the controller 20 so the unit will know whether it has been recently used to disinfect the wearer's hands (this time interval can be set in the software), or whether the wearer's hands have been disinfected since the previous zone was visited. These status flags may be used as a condition for a hygiene status indication light or signal that may be provided on or in association with the wearable device, such as by way of the LED or similar signal indicator shown schematically at 25a in FIG. 1B. Infrared zone identifier transmitters 26 define zones and are configured to emit pulse coded infrared signals to convey zone identifier information to the wearable unit. The coded signals incorporate check sums or other data integrity codes as is known in the art, to provide reliable detection reduce the possibility of false signals. Controller 20 is programmed to demodulate and decode the zone identity signals.

Fixed disinfectant dispenser assembly 31 can be used in conjunction with the smart wearable disinfectant dispenser 10. The fixed disinfectant dispenser assembly 31 can be permanently wall mounted or attached to a patient bed or alternatively, be mounted on a stand or pedestal so as to be available for the user of the smart wearable disinfectant dispenser 10 and to other persons, such as patients or visitors in a hospital. The user of the smart wearable disinfectant dispenser 10 can use the fixed disinfectant dispenser assembly 31 for convenience or if the dispenser cartridge 16 is empty. The user can still benefit from the prompting and data logging features of the smart wearable disinfectant dispenser 10. When the user dispenses disinfecting gel from the fixed dispenser 28 of fixed dispenser assembly 31, this action is sensed by dispensing sensor 30 and a coded signal is sent by infrared dispenser transmitter 32 to the infrared sensor 18 of the wearable device. The coded signal is distinguishable from zone identifier signals. The signal is transmitted for a short period of time, for example, several seconds, to allow the user to ensure the wearable unit captures the signal. Various feedback can be conveyed to the user. The fixed dispenser can have a visual indicator such as an LED to indicate when the infrared dispenser transmitter 32 is transmitting. The controller 20 then decodes the infrared signal and treats this information similarly to receiving an indication from dispensing sensor 22. The user can thus receive credit for disinfecting his/her hands. While the dispenser transmitter 32 is discussed as an infrared transmitter, other transmitters may also be used in some applications, such as ultrasonic or RF transmitters. If desired, the dispensing sensor 22 and controller 20 may be configured to detect when a dispenser is empty.

If desired, the controller may also be operable to decode, in addition to the zone identifier, one or more zone type identifiers in the zone identifier signal. In this case, the alerting device may be operable to issue one or more distinct types of alerts to the user according to the zone type identifier. The one or more zone type identifiers may, for instance, include an identifier that the zone is an isolation region in light of a predetermined communicable disease or condition, such as SEVERE ACUTE RESPIRATORY SYNDROME (SARS) or METHICILLIN-RESISTANT *STAPHYLOCOCCUS AUREUS* (MRSA). For instance, the zone transmitters 26 may be provided with a switch function which controls one or more bits as needed in the zone identifier signal to allow staff to indicate to the system that this particular zone is for an isolated patient, requiring special prompting. The system may then provide a more urgent signal, such as a louder or recognizably different signal when leaving this zone and possibly when approaching a subsequent zone to reduce the probability of transmission by encouraging greater attention to the importance of hand hygiene in this circumstance.

To this end, the plurality of zone identification transmitters may include a first group of one or more zone identification transmitters which are configured to transmit a unique zone type identification. Each of the zone identifiers in the first group may thus include a switch function to adjust the zone type identification. The switch function may include a switch unit located at the zone identification transmitter, as shown schematically at 26a in FIG. 2A, or be remotely adjusted and/or activated by the central computer 36, as shown by the communication path schematically in dashed lines at 26b which may be a wired or wireless communication path.

The controller 20 is provided with communication interface 34. It is shown here as a USB interface but persons skilled in the art will recognize that other interfaces could be used as well. The communication interface 34 can connect to a connector incorporated in a docking station configured to accept one or more smart wearable disinfectant dispenser assemblies 10. The docking station can store the wearable units when not in use, recharge batteries within the wearable units and download the logged data from the data memory 21.

Figure 2B:
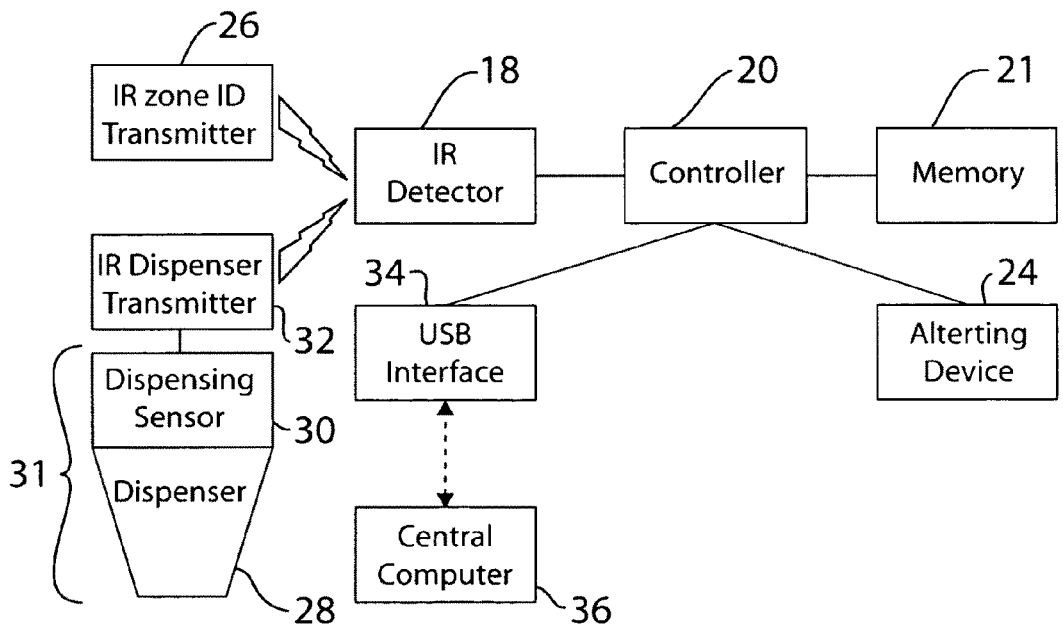
FIG. 2B is a block diagram illustrating a wearable smart zone sensor in a system of the present invention.

FIG. 2B illustrates a similar system to FIG. 2A but the wearable portion has a smart zone sensor without the wearable dispenser portion such as housing 14 and cartridge 16, as shown in FIG. 1B. The dispensing detector or sensor 22 is not required in this scenario and thus can be shielded by housing 25 or alternatively could be disabled by the firmware of controller 20 or alternatively smart zone sensor intended exclusively for use in housing 25 can be manufactured without the sensor 22. The smart zone sensor could be manufactured as a permanent component of housing 25. The wearable smart zone sensor 12 can be incorporated as part of a user's ID badge or could be a plain unit with no easily visible identifier information so that it could be used in an anonymous fashion.

FIG. 3 is a breakaway perspective view of the fixed disinfectant dispenser assembly 31 having a fixed housing 29 suitable for mounting on a wall, pole, pedestal, hospital bed or other suitable location. The fixed housing 29 contains disinfectant dispenser 28, a dispensing sensor assembly 30 and infrared transmitter 32. The dispensing sensor assembly 30 comprises a sensor for sensing a dispensing action of disinfectant dispenser 28, and control circuitry to generate a wireless signal to be transmitted by infrared transmitter 32. The infrared transmitter 32 comprises an infrared emitter and an infrared beam collimator or shield to limit the radiation pattern of the infrared emitter to a region or zone proximate to the disinfectant dispenser assembly 31. In this manner, a user disinfecting his/her hands using the disinfectant dispenser assembly 31 can present his/her wearable smart zone sensor 23 or wearable smart disinfectant dispenser 10 to the zone such that the zone sensor 12 is able to receive the wireless signal indicating that he/she has dispensed disinfectant. Other examples of the device 31 may not require the collimator.

Figure 4:
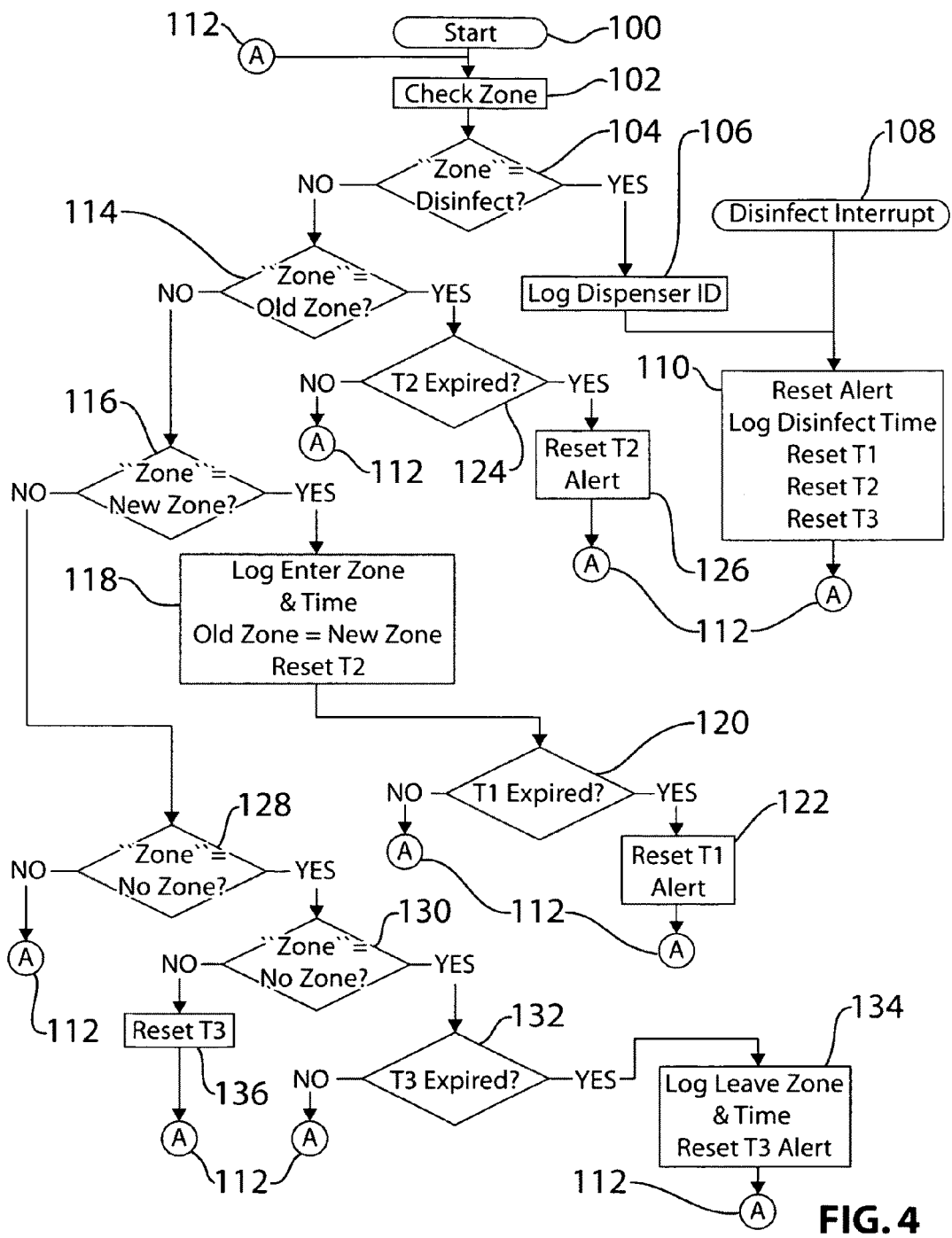
FIG. 4 is flowchart illustrating an embodiment of the present invention.

The operation of an embodiment of the present invention will now be described with reference to FIG. 4. In operation, the wearable smart zone sensor 12 monitors and logs hand disinfecting activity, and entering and leaving zones. The method starts at 100. The controller 20 polls the infrared (IR) detector 18 at step 102. A zone identifier signal is detected by infrared detector 18 and demodulated. An example of a suitable zone identifier signal is a pulsed code infrared signal on a 38 kilohertz carrier. A 5 millisecond preamble pulse precedes an 8-bit binary pulse stream representing a zone identifier. This is followed by a second representation of the zone identifier to act as a check-sum and confirm the accuracy of the demodulated zone identifier. One example of a second representation is a pulse stream representing the zone identifier offset by a predefined number. Other check-sum techniques can be used, as is well known in the art, such as inverting the first pulse stream representation. An 8-bit identifier can distinguish up to 256 different zones. More bits can be used for defining zone identifiers as required.

Once a zone identifier has been determined, the controller 20 performs a series of tests starting at 104 where the zone identifier is compared to a "zone identifier" code which is associated with one or more fixed disinfectant dispensers. In one embodiment, one bit of the zone identifier binary representation, represents a disinfectant dispenser, thus if this bit is detected, the decision at step 104 is determined to be "yes" in which case, at step 106, the controller 20 logs the "zone identifier" identifying the dispenser. The process continues to step 110 where the disinfecting action is logged with the associated time of day and date. If the alerting device 24 is activated, it is reset. First timer T1, second timer T2 and third timer T3 are also reset to begin counting down. Note that this functionality can be used with either a wearable smart disinfectant dispenser assembly 10 or a wearable smart zone sensor assembly 23. If desired, a timer function may also be provided, to start when the gel is dispensed and beep after a preset time (e.g. 15 sec) to mark the end of a washing procedure, so that user knows how long they need to wash/rub for a particular sanitizing process.

First timer T1 represents an acceptable period of time for a user to have disinfected his/her hands in advance of entering a zone, thus a nurse or healthcare worker can sanitize his/her hands while approaching a patient's room. This mechanism can then avoid triggering the alerting device 24 if the healthcare worker is conscientious and efficient. The capability to avoid triggering the alerting device can encourage healthcare workers and other users, to practice good hand hygiene and can possibly help in conditioning such behavior. An example of such a time period is 10 to 40 seconds. This time can be preset and could be configurable by an administrator using an external computer such as computer 36 in FIGS. 2A and 2B.

Second timer T2 represents an acceptable amount of time for a healthcare worker to be inside a zone without sanitizing their hands. Even when restricted to a zone of a single patient, it is possible to cross contaminate the healthcare worker's hands from coming in contact with various bodily fluids, handling open wounds, handling bedpans, etc. The T2 timer can be set to 10 minutes for example.

Third timer T3 represents a time delay before determining that a user has left a zone. A worker could briefly step outside a zone while walking around a patient's bed for example. The wearable zone sensor could be briefly obscured while bending over a patient or by movement of the user. T3 thus "forgives" such intermittent interruptions of a zone signal. The process then returns to the start of the flowchart as indicated by "A" 112.

Step 110 can also be reached by an interrupt signal 108 received from a directly connected dispensing sensor 22 of a wearable smart disinfectant dispenser assembly 10.

If at step 104, the zone identifier is determined not to be a disinfectant dispenser "zone identifier" code, then the process continues to step 114 where the zone identifier is compared to an "old zone" identifier stored in memory 21. If the current zone is the same as the old zone, then the user is still in the same zone and timer T2 is tested at step 124. If T2 has expired then at step 126, timer T2 is reset and the alerting device 24 is activated and the process returns to the start through 112. If the current zone is not the same as the previous zone (old zone) then at step 116, the zone identifier is tested to see if it is a new zone. If yes, at step 118 the current (new) zone is logged in memory 21 along with the corresponding time-of-day and date; the new (current) zone is stored as the old zone; and timer T2 is reset. If the current zone is not a new zone, then at step 128, the zone identifier is tested to determine if not in any zone. If the user is in a recognizable zone, the process continues at the start via 112. If the user is not in a zone, then the process continues at step 130 where the old zone is tested to see if it also was "no zone" in which case timer T3 is tested at step 132 to see if the user has been outside of a zone sufficiently long to make a determination that in fact the user is outside of a zone and not just obscuring the sensor temporarily. If it is determined that the user has left a zone, then at step 134, the time and date of leaving the zone is logged in memory 21; timer T3 is reset; and the alerting device 24 is activated. To avoid activating the alerting device, the user should disinfect his/her hands within the time delay of T3. The process then returns to the start via 112. With timer T2 reset in step 118, the device queries at step 120 if timer T1 has expired. If no, the device advances to step 112. If yes, timer T1 is reset in step 122 and the device proceeds to step 112.

If at step 130, the old zone was not "no zone" then "no zone" is a new condition and the system can not yet determine if the user is actually outside of a zone or is merely obscuring the sensor 18 temporarily in which case at step 136, timer T3 is activated to track the interval during which it is no definitive determination can be made.

Another embodiment of the present invention will now be described with reference to FIG. 5. In operation, an embodiment of the wearable smart zone sensor 12 implements the process of FIG. 5, which starts at step 200. At step 202, the controller 20 polls the IR detector 18 to determine if a zone has been detected and if not loops back to step 202 to repeat the step until a zone is detected, in which case the process advances to step 204 where the controller 20 stores the zone identifier (ID) in memory 21. The process continues to step 206 where the controller 20 checks if first timer T1 has expired and if it has, alerting device 24 is activated at step 208. If timer T1 has not yet expired, the process continues to step 210 where the controller 20 tests if the current detected zone is the same zone as the previous zone, that is, the user is still in the same zone. If it is, the second timer T2 is tested at step 212. If timer T2 has not expired, the process returns to step 210. If timer T2 has expired, at step 214, the alerting device is activated and the process returns to step 210. If at step 210, the controller determines that the user is not in the same zone, the process continues to step 216 where the current zone is tested to see if it is a new zone and if not, at step 218 the third timer T3 is tested to see if it has expired. If timer T3 has not expired, the process returns to step 210. If timer T3 has expired the alerting device 24 is activated at step 220 before the process returns to the start of the process at step 202. If at step 216, it is determined that the current zone is a new zone, the system determines at step 222, if the disinfectant dispenser has been activated since the previous zone and if it has, the process returns to step 206. The system can monitor an integral wearable dispenser 16 or a fixed dispenser 28 as previously described. If at step 222, the disinfectant dispenser has not been activated since the previous zone, then at step 224, the user is alerted by alerting device 24, and the process returns to step 210.

FIGS. 6A, 6B, 6C illustrate how the smart wearable disinfectant dispenser assembly 10 (10a, 10b, 10c) can be worn by a user. The wearable smart zone sensor assembly 23 can be worn in a similar manner. The smart wearable disinfectant dispenser 10a is configured to clip onto a chest pocket on the user's clothing. The smart wearable disinfectant dispenser assembly 10b mounts on the sleeve of the user's clothing by a spring clip, a magnetic pad with a cooperating ferrous metal plate on the inside of the sleeve, with a pin the fabric of the sleeve, via a harness 38 worn over the sleeve or any other suitable means. The smart wearable disinfectant dispenser assembly 10c is mounted on a harness 40 worn on the user's shoulder. In general, it is advantageous to carry the wearable dispenser 10 higher on the user's body so as to be easily accessible for dispensing the disinfecting gel, so as to not interfere with the user's other daily tasks such as to administer care to patients and to best position the infrared sensor 18 to receive infrared signals from overhead zone identifier transmitters.

Figure 7:
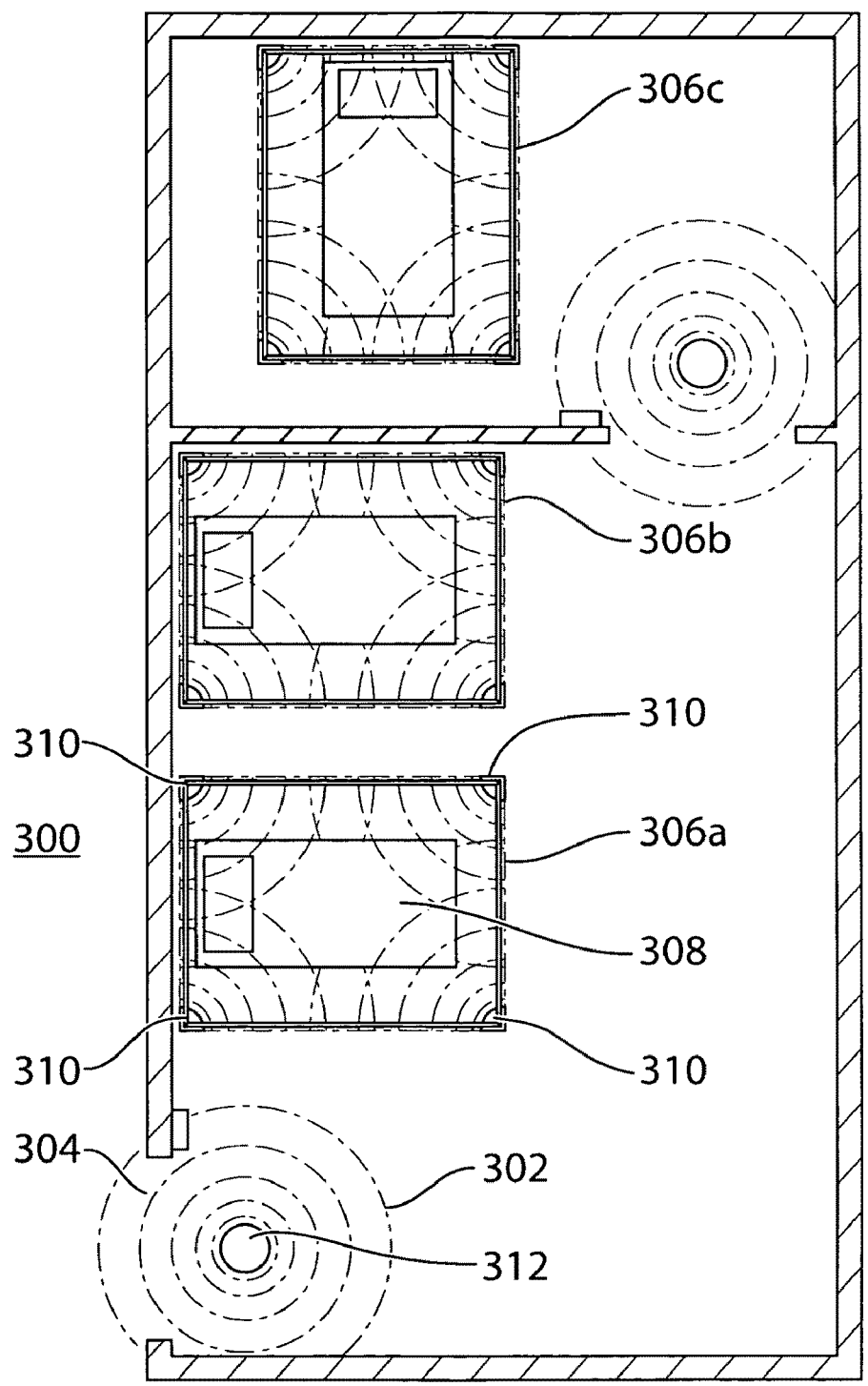
FIG. 7 is a plan view showing an exemplary layout of an embodiment the system of the present invention in a hospital setting.

The layout of zones will now be described with reference to FIG. 7 which illustrates a plan view of an exemplary layout of zones in a hospital setting 300. Zone 302 covers a doorway 304 to a hospital ward or department. Zone 302 is defined by a zone beacon 312 which comprises an infrared emitter driven by a transmitter circuit to modulate the infrared radiation to transmit a signal representing a zone identifier. The emitter of zone beacon 312 can have a shield of conical shape to define a conical zone. Other shapes of shields can be used to define different shaped zones as required. Zone 302 can be coded as a transitional zone and the firmware in the wearable zone sensor can be configured to require a disinfecting action only once while moving through the transitional zone 302. A zone 306a can be defined around a patient bed 308 using a zone beacon array of emitters 310, which are described in more detail with reference to FIG. 8. The patient bed zone 306a has clearly defined vertical boundaries which permits adjacent patient bed zone 306b to be located relatively close by without causing interference or overlap of zones. A zone is also shown at 306c around a nearby patient bed.

Figure 8:
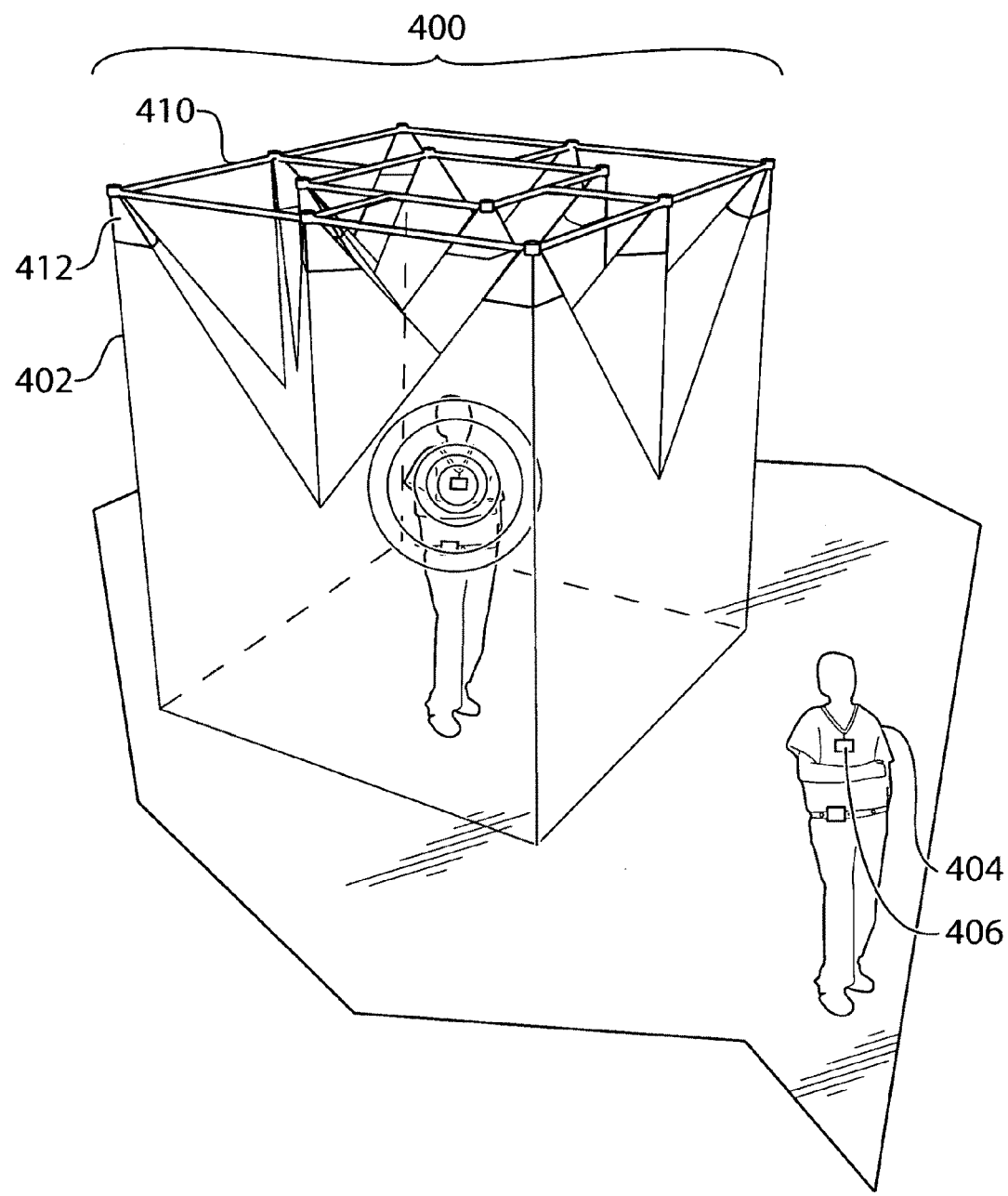
FIG. 8 is a perspective illustration of a zone defined by an embodiment of a zone array of the present invention.

With reference to FIG. 8, a zone 402 is defined by an embodiment of a zone beacon array 400 of the present invention. The zone beacon array (zone array) 400 includes an array of infrared emitters, each having a shield/cone/"collimator" 412 to clearly define the radiation pattern of each infrared emitter. The emitters and associated shields 412 are supported by a frame 410. This arrangement facilitates defining a zone having clearly defined boundaries with vertical walls. It is thus possible to have different zones quite close to one another without overlapping and possibly causing interference. The frame 410 can accommodate wiring to interconnect emitters from the same zone. A common transmitter circuit (not shown) provides the modulated zone identifier signal to drive each of the emitters as discussed previously. The frame 410 can be lightweight and easily suspended from a ceiling and may be integrated into a suspended ceiling as desired. The transmitter can be relatively low powered and be powered from an electrical power outlet with a power supply. A small battery can be supplied to provide uninterruptible power if required.

Figure 9:
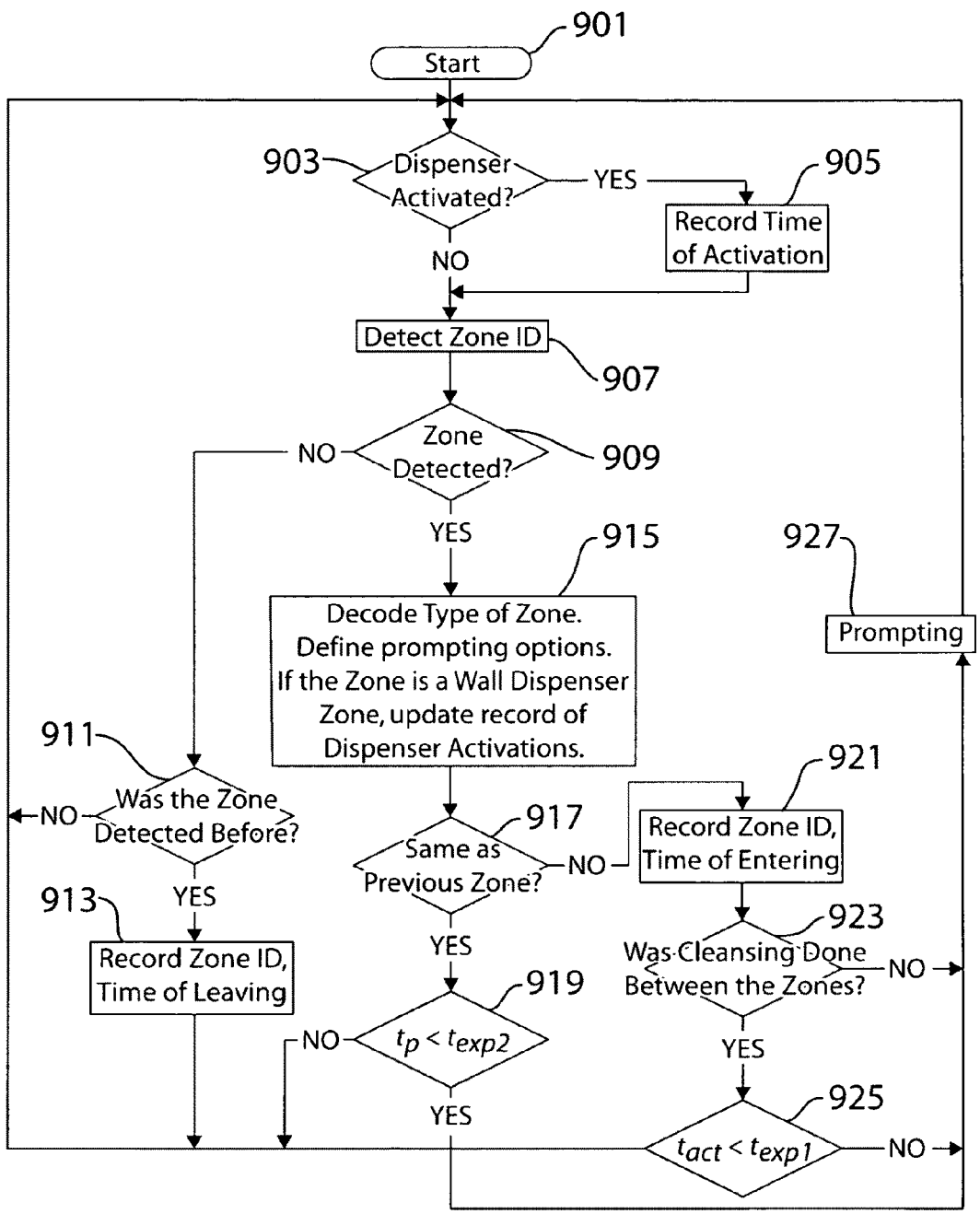
FIG. 9 is flowchart illustrating another embodiment of the present invention.

FIG. 9 is a simplified flowchart illustrating another embodiment of the present invention. The flowchart describes the logic of the wearable smart zone sensor/dispenser operation within the distributed hand hygiene compliance system. In this example, a number of software timers is used to adjust disinfection expiry intervals for different clinical environments, where:

$t_p$ is the time of working with patient (time spent inside the zone);

$t_{exp2}$ is the expiry time inside the zone;

$t_{exp1}$ is the expiry time outside the zone; and $t_{act}$ is the time of dispenser activation.

The device is in sleep mode most of the time and wakes up (or may otherwise be activated) periodically to check the presence of the zone emitters at step 903 with the time of activation recorded at 905. Duration of the power saving intervals is controlled by a watchdog timer and defined by the maximum acceptable reaction time when the user/caregiver enters the zone. The portable unit can also be woken up by an interrupt signal resulting from dispenser activation in the case of a directly connected dispenser. If the zone is detected at step 907 as determined at step 909, the device decodes, at step 915, the type of zone, by being responsive to different signals being emitted from different zones, not only to identify each of them uniquely, but also to classify them as between a full zone, a micro zone or a wall dispenser zone. The device checks, at step 917, to see if the detected zone is the same as the previous zone. The device checks at step 925 that the last disinfection occurred not earlier than the disinfection expiry time texp1 outside of the zone. Note that texp1 is programmable and may vary for different applications. If disinfection was not performed or the time is already expired (step 919) the device prompts the caregiver at step 927 to activate dispenser. When the device leaves the zone its disinfection status flag remains set to clean for a certain programmable period of time, so the caregiver is allowed to leave the zone temporarily and come back without being prompted for disinfection. In this situation if device detects the zone which is different from the previous one at step 917 and dispenser was not activated between the zones (step 923 via step 921 to record the zone ID and time of entering the zone) the disinfection status flag changes immediately issuing the prompting signal (step 927). If the zone is not detected at step 909, then the device queries, at step 911, if the zone was detected before. If yes, then the device records zone ID and the time of leaving at step 913 and reverts back to step 903. If, at step 911, the zone is not detected, then the device reverts back to step 903.

Figure 10:
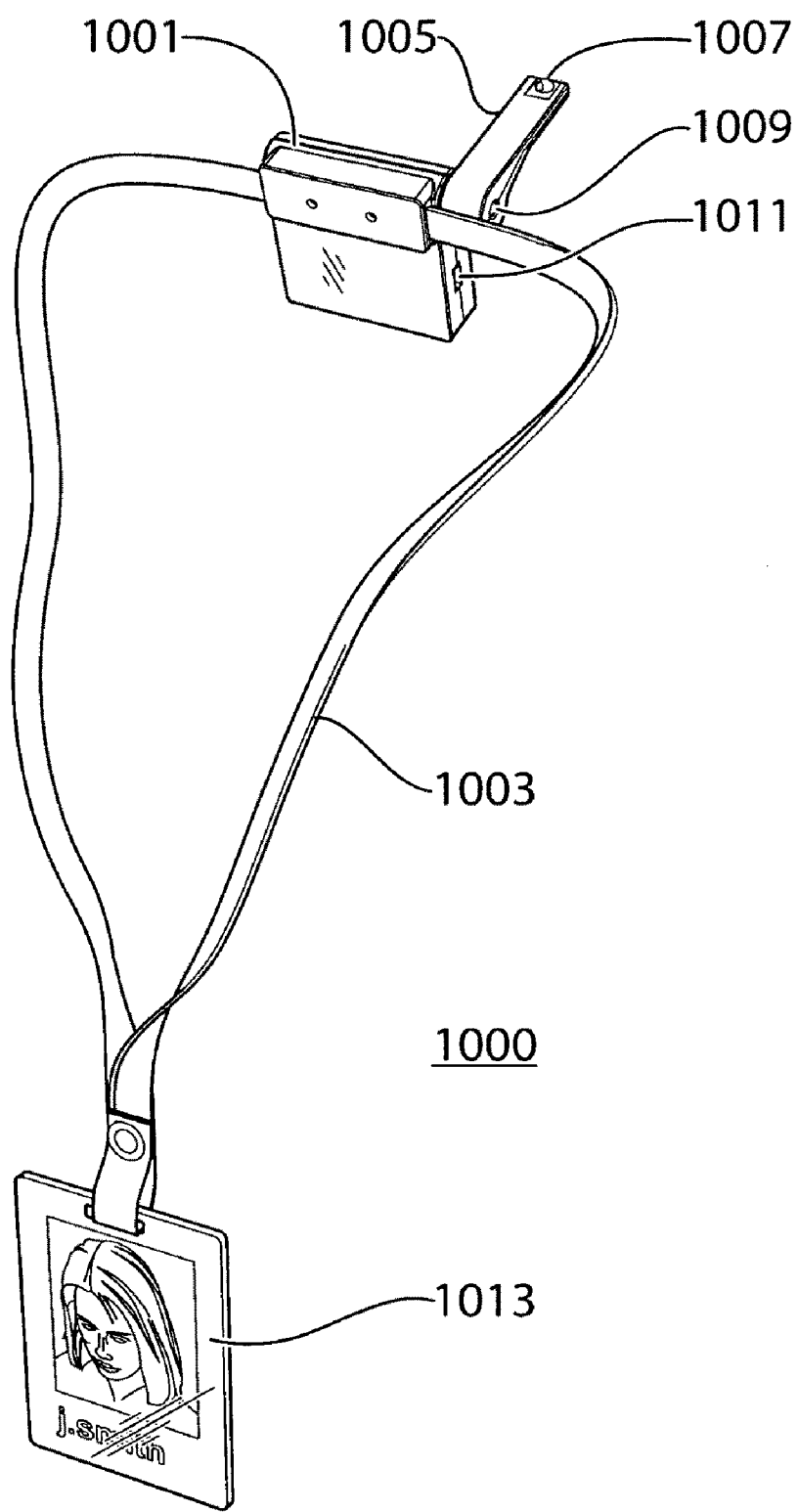
FIG. 10 is a perspective illustration of a lanyard—ID card embodiment of the present invention.

Another embodiment of the present invention is illustrated in FIG. 10 where 1000 is a wearable smart zone sensor. The controller 1107 (not shown) is contained within housing 1001 which is attached to a lanyard 1003, of the type typically used to carry a user identification (ID) card 1013. When this device is worn by a user the controller housing 1001 will be situated behind or near the user's head or lower down the body of the user. Arm 1005 is pivotally attached to housing 1001 and in an operating position it extends outwardly away from the user such that infrared detector or detecting means 1007, or in other words an electronic eye, is clear of the user's head and hair and is in a position to accept infrared signals from zone identifier signal transmitters. In this embodiment an alerting device 1009 such as a beeper is located adjacent to the pivot of arm 1005. A USB connector 1011 is available to connect that device to a reporting means such as an external computer to download stored data. This embodiment can be used by users such as caregivers, patients, visitors in a healthcare facility to prompt the user to sanitize his or her hands when moving from zone to zone. The user can use fixed handwash dispensers of the present intention, mounted on walls near patient zones to sanitize his/her hands. These fixed handwash dispensers can transmit infrared signals indicating that handwashing and was performed, which can be received by the wearable unit and logged.

Figure 11B:
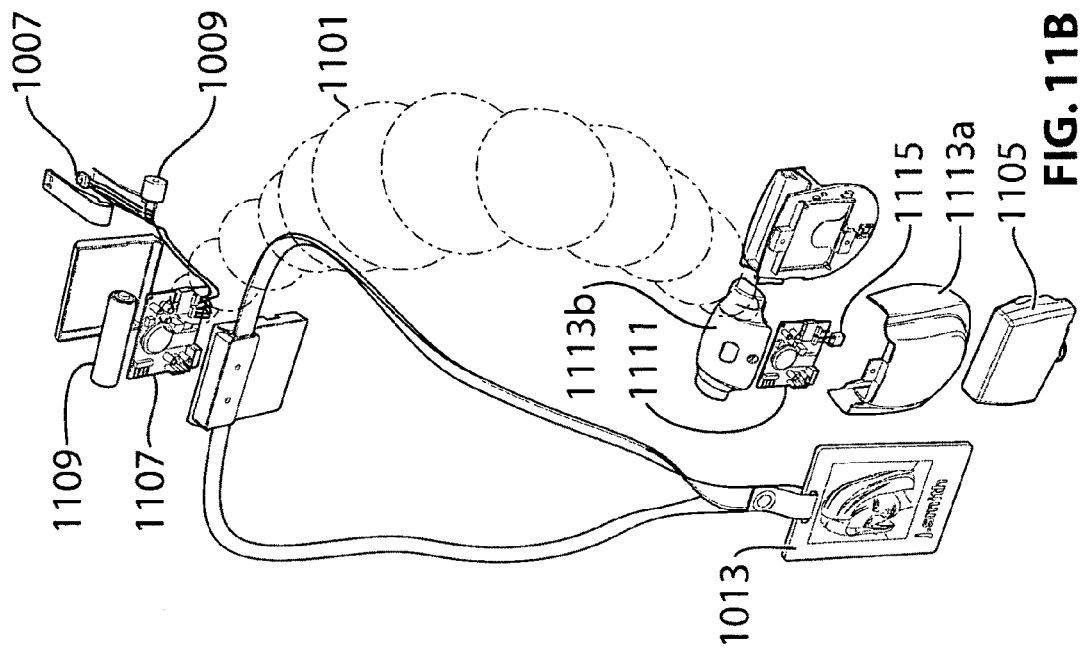
FIGS. 11A and 11B illustrate a perspective view and a break-away perspective view respectively, of a lanyard—ID card with a wearable dispenser with RF communication embodiment of the present invention.
Figure 11A:
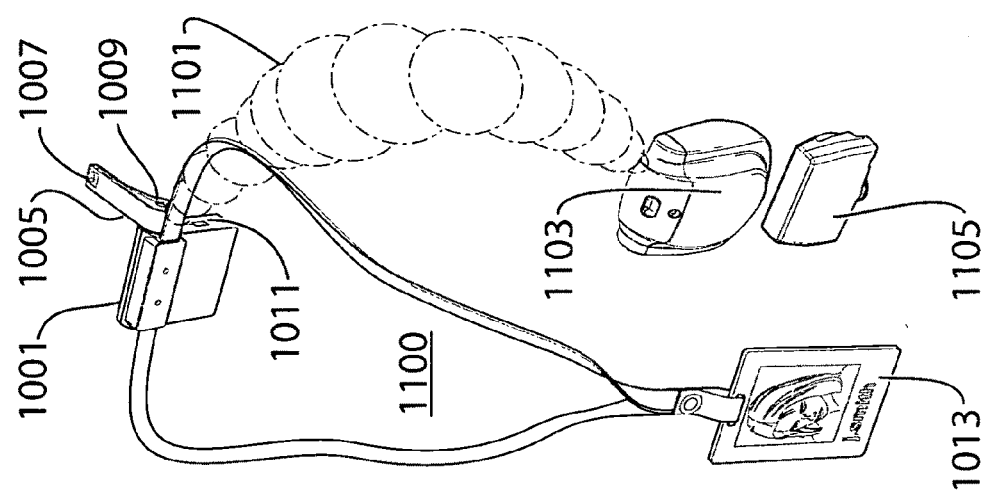

FIGS. 11A and 11B illustrate a perspective view and a break-away perspective view respectively, of another embodiment of a wearable smart zone sensor within housing 1001 and working in cooperation with a corresponding wearable dispenser unit 1103 including dispenser cartridge 1105 and having an RF or other communication link 1101 with the wearable smart zone sensor 1000. This embodiment works similarly to the embodiment of FIG. 10 with the added functionality of having the wearable hand sanitizer dispenser 1103 conveniently available. The wearable hand sanitizer dispenser 1103 can sense a dispenser activation via switch 1115 and transmit this information by way of an RF transmitter located on printed circuit board 1111 held within housing portions 1113*a*, 1113*b*. RF signal 1101 is received by logic board 1107 having an RF receiver. Thus handwash activity can be performed conveniently by the user and the activity can be logged.

FIGS. 12A and 12B illustrate a perspective view and a break-away perspective view respectively, of another embodiment of a wearable smart zone center similar to that of FIGS. 10 and 11, but in this case the wearable dispenser 1203 is attached to the lanyard 1003. This embodiment has the advantages of not requiring a clip in order to wear the wearable dispenser and of avoiding the costs and complexity of an RF transmitter circuit and receiver, using instead a wire connection 1201 running through lanyard 1003 and terminating at end region 1205 with a dispensing sensor 1207.

As an example of construction details, the wearable unit in this system can be constructed using a PIC18LF2550 microcontroller, a 24LC256 EEPROM for data storage, a DS1338 real time clock, communicating with microcontroller via I2C interface, and a PNA4602 infrared detector. The short-range RF link between the wireless wearable gel dispenser and the wearable zone sensor can use an rfRXD0420 or MICRF211 based 433.92 MHz receiver.

The wearable electronic units and gel dispensers work in pairs with each dispenser being equipped with a MAX1472 based transmitter to inform corresponding electronic unit about dispenser activations. In this configuration the main functions of wearable electronic unit are to demodulate and decode zone identity signals, record the real time of entering/leaving the zones and dispenser activations, provide prompting if required, store hand hygiene activity history as well as the detected codes of the zones. The hand disinfection status "flags" of the caregiver (clean or dirty) are stored in the wearable unit so it knows whether it has been recently used to disinfect the wearer's hands (this time interval can be set in the software), or whether the wearer's hands have been disinfected since the previous patient zone was visited. Advantageously, this distributed system does not require a real-time central co-coordinator. The data recorded by the wearable smart zone sensors units can be later downloaded to a PC via a USB interface for monitoring and further analysis.

Furthermore, an indication such as a light or other signal unit may be provided integrally the wearable dispenser 1203*a* as shown in FIG. 12A, for example on the housing 1203, or elsewhere on housing 1113 in FIG. 12B, or separate therefrom, or with the lanyard 1003, or the badge shown at 1013, as an indication of the status flag. This would permit, for instance, a patient in a patient zone to determine if the attending user has executed the required disinfection step before visiting the patient's zone in particular. If the status signal is "red" for instance, it may give the patient a cue to remind the user to disinfect before proceeding further. Alternatively, the patient may see a green signal indicating that the user has indeed disinfected prior to the visit.

Figure 13A:
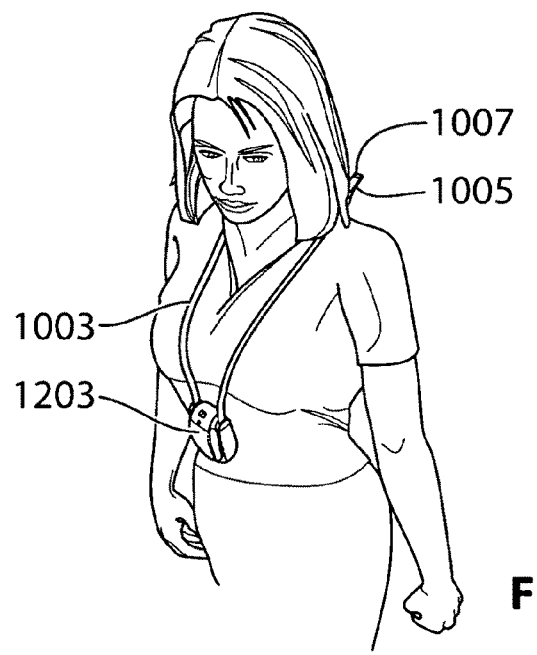
FIG. 13A, 13B, 13C illustrate various locations for wearing an embodiment of a wearable smart handwash dispenser.
Figure 13B:
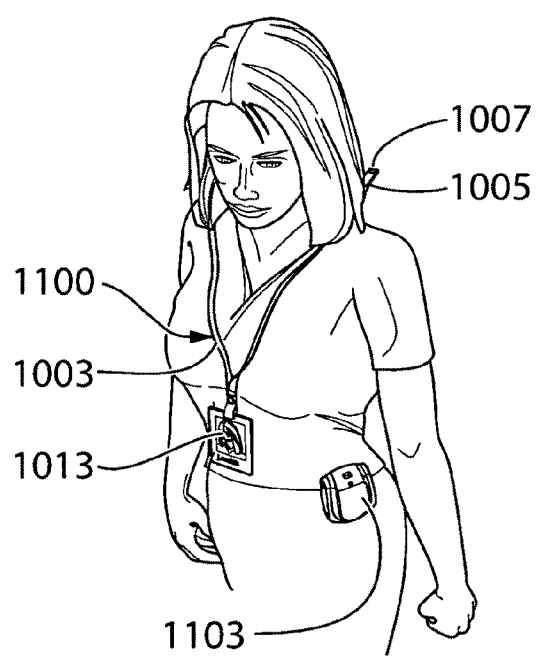
Figure 13C:
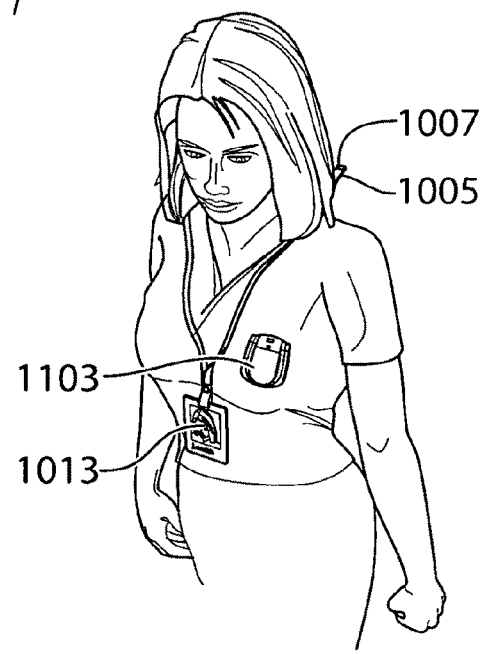

FIG. 13A, 13B, 13C illustrate various locations for wearing the embodiments of FIGS. 10, 11, 12. Note that infrared sensor 1007 on arm 1005 is exposed beyond the user's hair so as to have improved line-of-sight to at least one infrared transmitter when the user is inside a zone.

Figure 14:
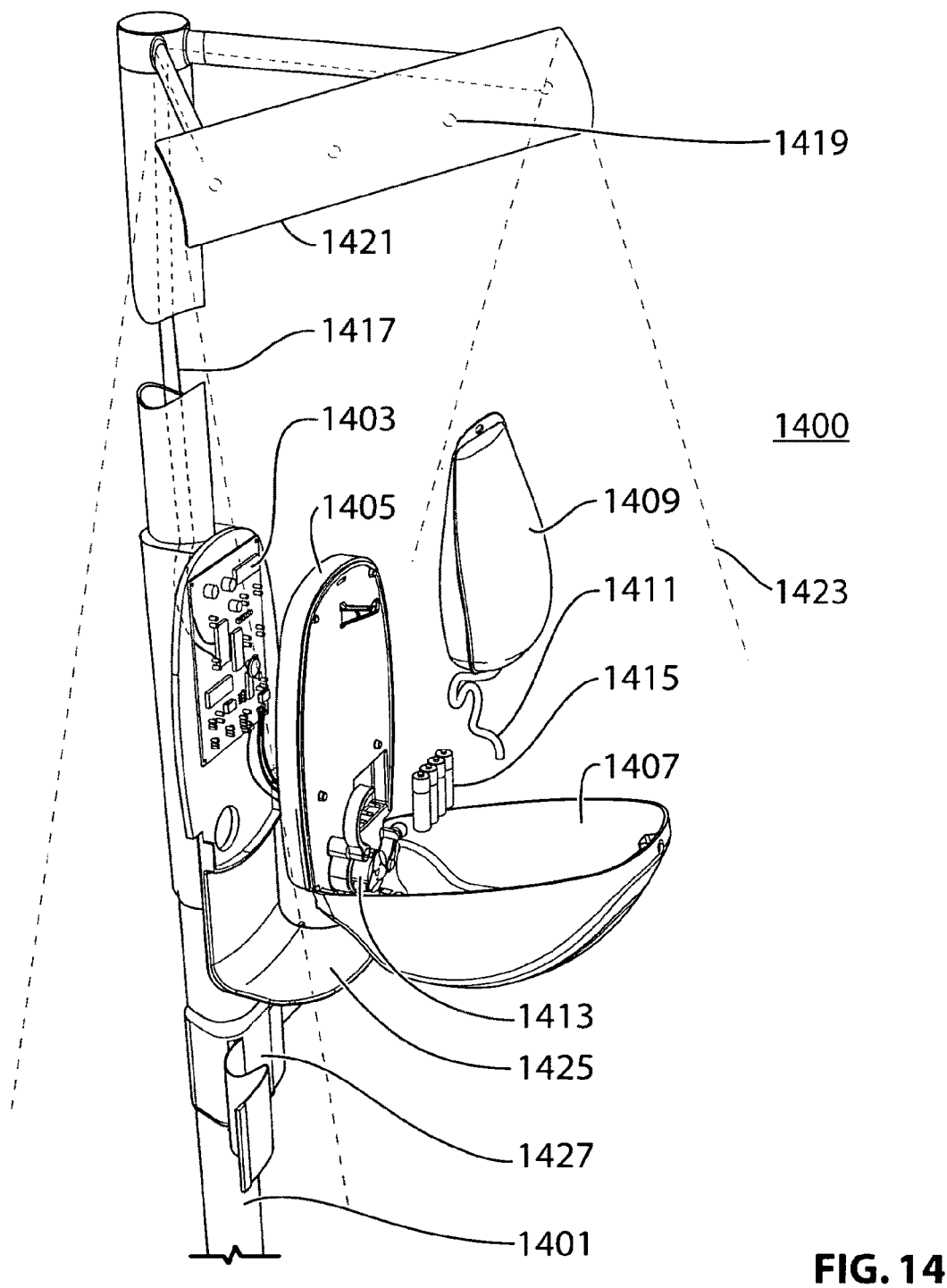
FIG. 14 illustrates a break-away perspective view of a fixed dispenser embodiment of the present invention.

FIG. 14 illustrates a break-away perspective view of an exemplary embodiment of a fixed pylon-mounted dispenser 1400 of the present invention. The fixed dispenser is mounted on pylon or pole 1401. Printed circuit board 1403 comprises controller functions for encoding infrared zone identifier signals, for controlling and interfacing with proximity sensor (not shown), and for controlling a pump such as a peristaltic dispenser pump assembly 1413. The fixed dispenser 1400 uses replaceable refill bag 1409 for providing the disinfecting gel held within housing portions 1405, 1407. The housing portions 1405, 1407 are, in turn, mounted on the pole 1401 with a drip catch tray 1425 located below the outlet of tubing 1411. Tubing 1411 dispenses the disinfecting gel from bag 1409 by squeezing action of rollers of peristaltic pump assembly 1413. The fixed dispenser 1400 uses electric power provided by four AA batteries 1415, or an alternative power supply may be used as desired. In operation when a user places his/her hands under the fixed dispenser 1400 the proximity sensor detects the placement of the hands and the printed circuit board (PCB) control circuit activates the dispensing pump assembly 1413 to dispense sanitizing gel. The dispensing pump assembly 1413 can be programmed to dispense different amounts of gel, for example 1 ml of gel every second for up to four seconds. When a dispensing activation takes place, the PCB control circuit then generates a zone ID signal which travels through wires 1417 to IR emitter array as shown by dashed lines at 1419 behind reflector 1421. This zone ID signal is only transmitted for a short time and is coded to inform the user's wearable smart zone sensor that a hand sanitizing operation has been performed. The logic of the controller of the wearable smart zone sensor will sense the zone ID signal and when it decodes the zone ID as representing the dispensing action, it will set the status flag to "clean" and log the action in the memory. Thus the fixed dispenser creates a "micro zone" where the zone ID signal is transmitted only briefly, following a dispensing action. The zone boundaries 1423 are determined by the shape of reflector 1421.

Figure 15B:
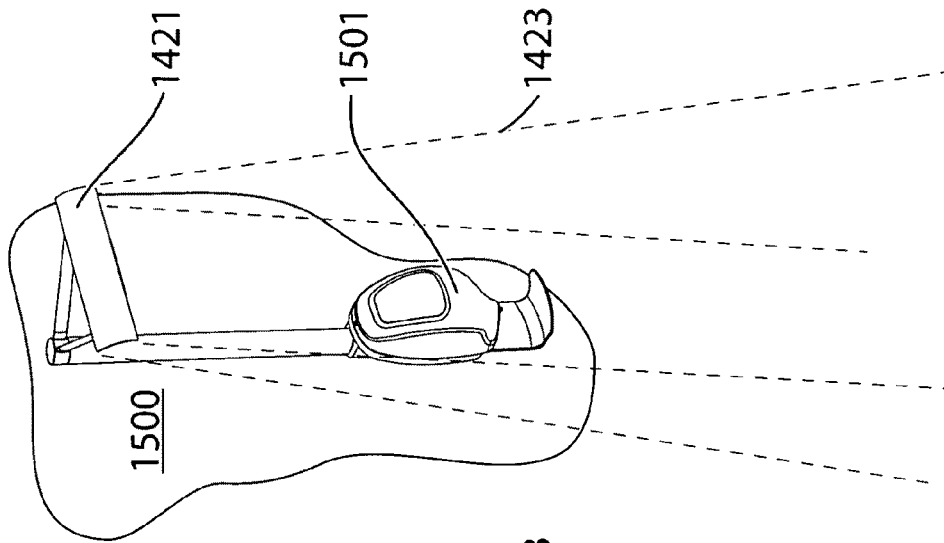
FIG. 15B illustrates a perspective view of a wall-mounted fixed dispenser of the present invention.
Figure 15A:
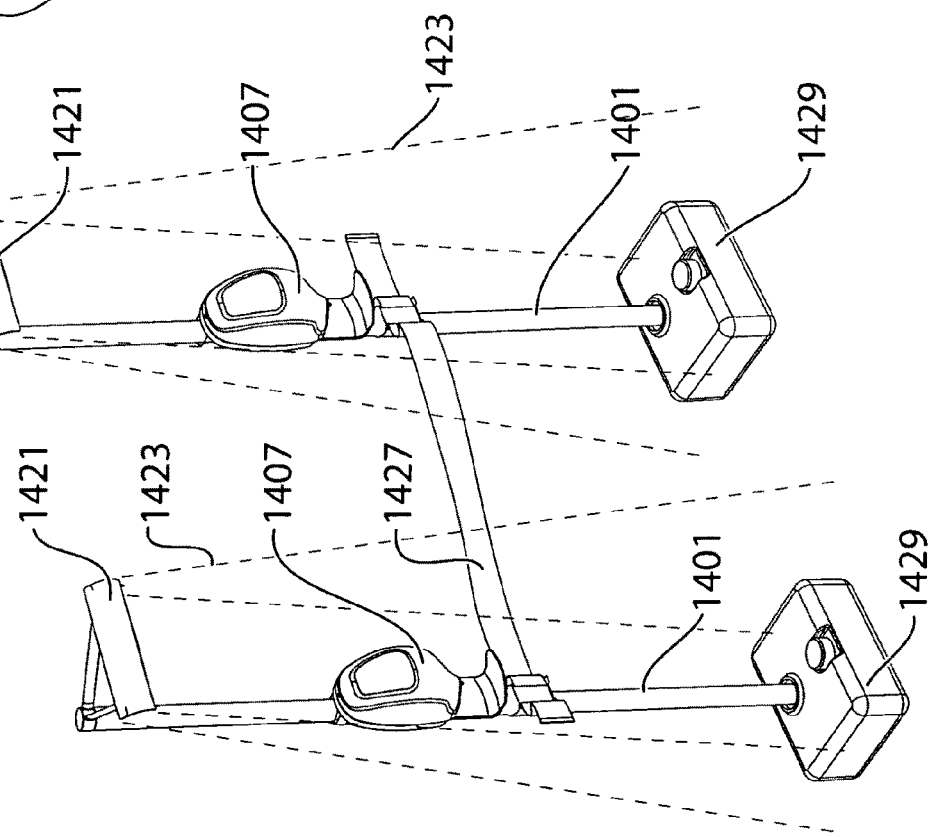
FIG. 15A illustrates a perspective view of a pylon-mounted fixed dispenser of the present invention.

FIG. 15A illustrates a perspective view of a pylon-mounted fixed dispenser of the present invention. The pylons 1401 are set in bases 1429 to support the pylons. Retractable physical barrier ribbon 1427 can span between pylons or between a pylon and a wall to control pedestrian traffic, and can be used to direct persons to a conveniently located fixed a dispenser to encourage hand hygiene. This can be reinforced by appropriate signs. This arrangement can be useful for controlling hand hygiene compliance in wide hallways, for example, or to define and set up temporary zones.

FIG. 15B illustrates a perspective view of a wall-mounted fixed dispenser 1501 which is similar to the pylon-mounted fixed a dispenser except that it is configured to be mounted on a wall 1500.

Figure 16:
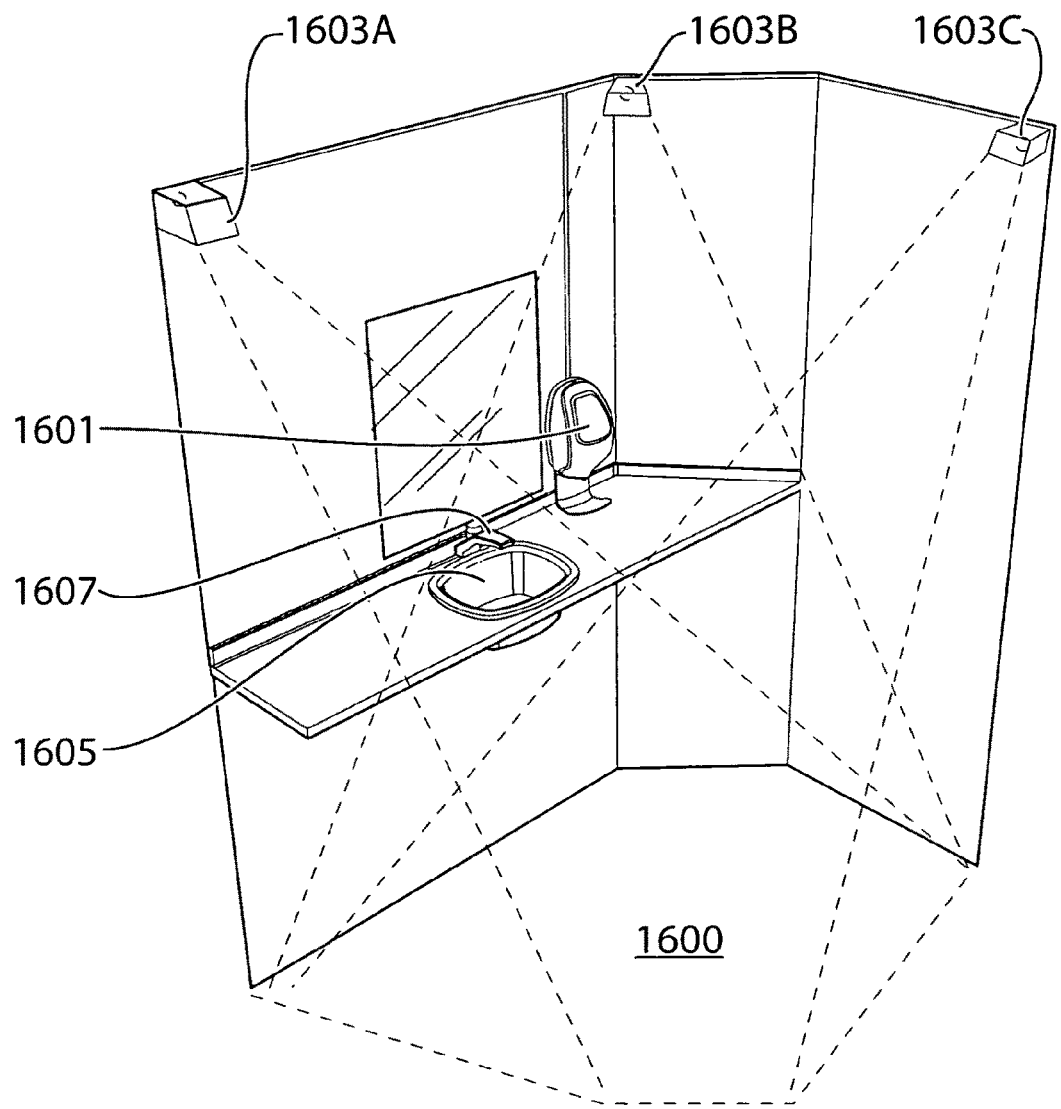
FIG. 16 illustrates a perspective view of a bathroom zone embodiment of the present invention.

FIG. 16 illustrates a perspective view of a bathroom zone embodiment 1600 of the present invention. In this embodiment, fixed dispenser 1601 can be used to dispense liquid soap which can be used in conjunction with water from faucet 1607 and sink 1605. The fixed dispenser 1601 is physically similar to wall-mounted fixed dispenser 1501. Infrared emitters 1603A, 1603B, 1603C transmit a zone identifier signal which is encoded to provide identification of the zone type. Thus when a user wearing a wearable smart zones sensor enters the bathroom zone the smart zone sensor logs the zone identifier for the bathroom zone. Fixed dispenser 1601 is configured to transmit a modified zone identifier signal for a short duration upon dispenser activation. This modified zone identifier signal is encoded to inform the smart zone sensor that a dispenser activation has occurred to allow the smart zone sensor to set the status flag to "clean" and to log the activation in memory. When the user leaves the bathroom zone without a dispenser activation of either the fixed soap dispenser 1601 or a wearable disinfectant dispenser, the smart zone sensor will alert the user with a single long duration prompt. This is a contrasted by the persistent prompt that the user receives from the smart zone sensor when the user enters a patient zone without proper hand cleansing activity. In other embodiments the fixed bathroom zone dispenser 1601 can be applied with disinfecting gel instead of liquid soap. Other embodiments would provide dispensers for liquid soap and for disinfecting gel.

Figure 17:
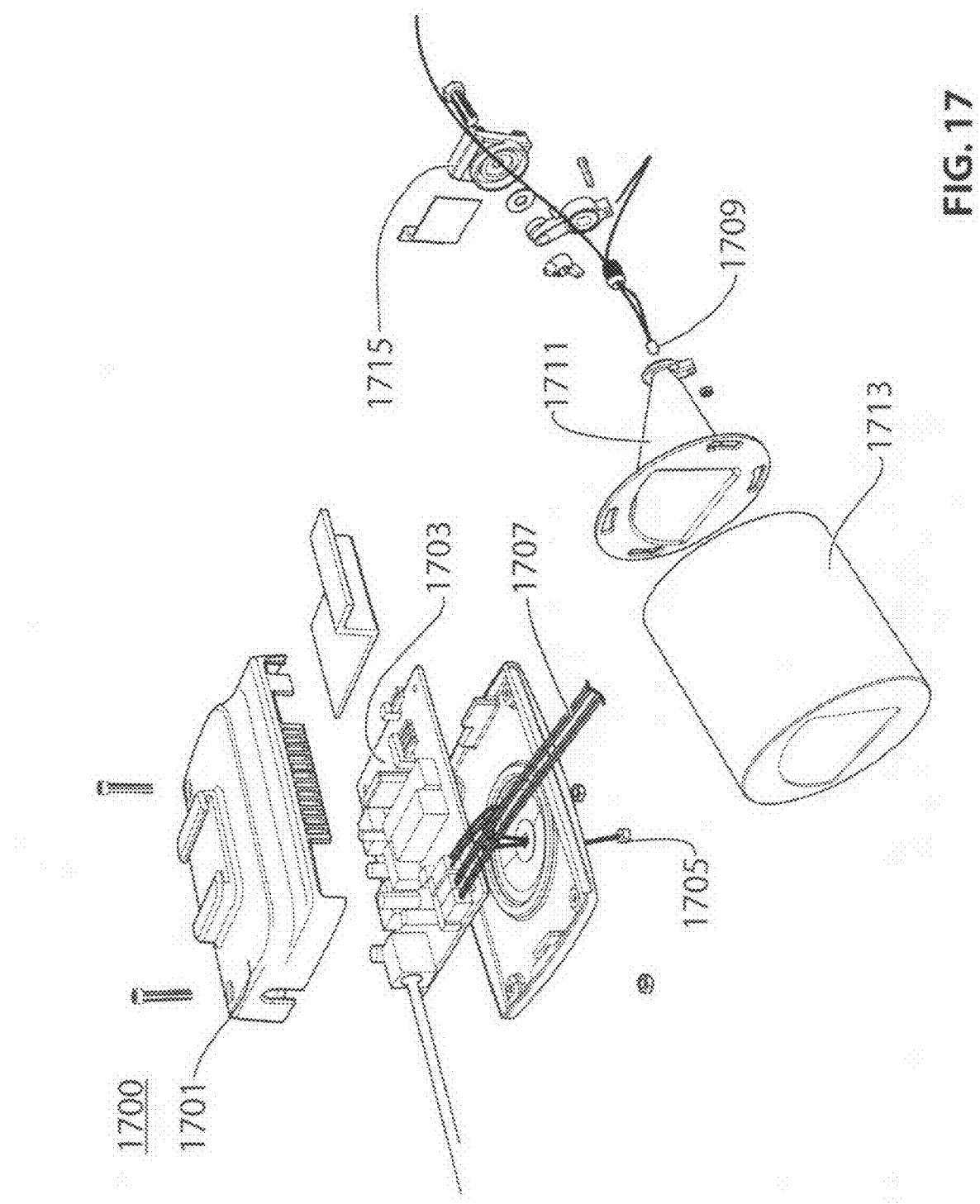
FIG. 17 illustrates a break-away perspective view of an embodiment of a zone controller of the present invention.

FIG. 17 illustrates a break-away perspective view of an embodiment of a zone controller 1700 of the present invention. The zone controllers 1700 comprise a zone controller housing top 1701 and a printed circuit board controller 1703. The controller is configured to transmit a zone identifier signal to infrared LED emitters 1709 via wires 1707. Each infrared emitter is mounted in a collimator cone 1711 which has a dust cover 1713. In one embodiment the collimators are configured to mount on T-bars of suspended ceilings by means of T-bar clip 1715. Other mounting arrangements for the light-weight collimator cones will be readily apparent to persons skilled in the art. In one embodiment the infrared emitters 1709 are connected in series in groups of six emitters, driven by the current source on printed circuit board controller 1703. Ambient light sensor 1705 is used by controller 1703 to adjust the drive current to the infrared emitters 1709 in order to provide crisp boundaries of the infrared zone, according to varying levels of ambient lighting in the zone.

An entrance zone can be provided using zone controller 1700, configured to transmit a zone identifier signal comprising a zone type identifier. An entrance zone can have different hand hygiene compliance requirements compared to a bathroom zone or a patient zone. The wearable smart zone sensors can be programmed to recognize different zone types by decoding the zone type identifier within the zone identifier signal. Different actions can be taken and different timing parameters can be used by the wearable smart zones sensors responsive to the zone type. For example when the wearable smart zones sensor detects an entrance zone, it can be programmed to produce a single long prompt if cleansing was not performed within the expiring time before entering the zone. When the user leaves the entrance zone and no other zone is detected within a predefined or programmable time. A long prompt is issued. The wearable smart zone sensor can be programmed not to prompt the user as long as the user remains within the entrance zone. The wearable smart zone sensor can also be programmed not to prompt the user when passing through the entrance zone while traveling between patients if proper hygiene procedures were performed between the patient zones.

Figure 18A:
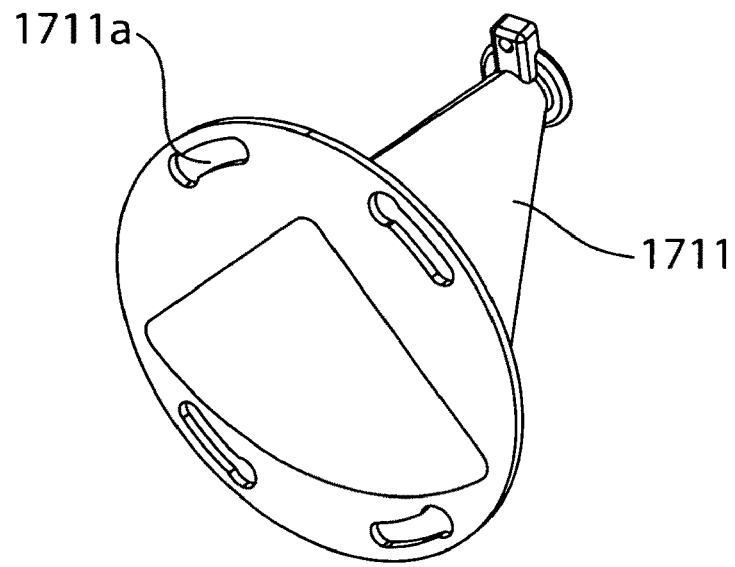
FIG. 18A illustrates a perspective view of an embodiment of a collimator of the present invention.
Figure 18B:
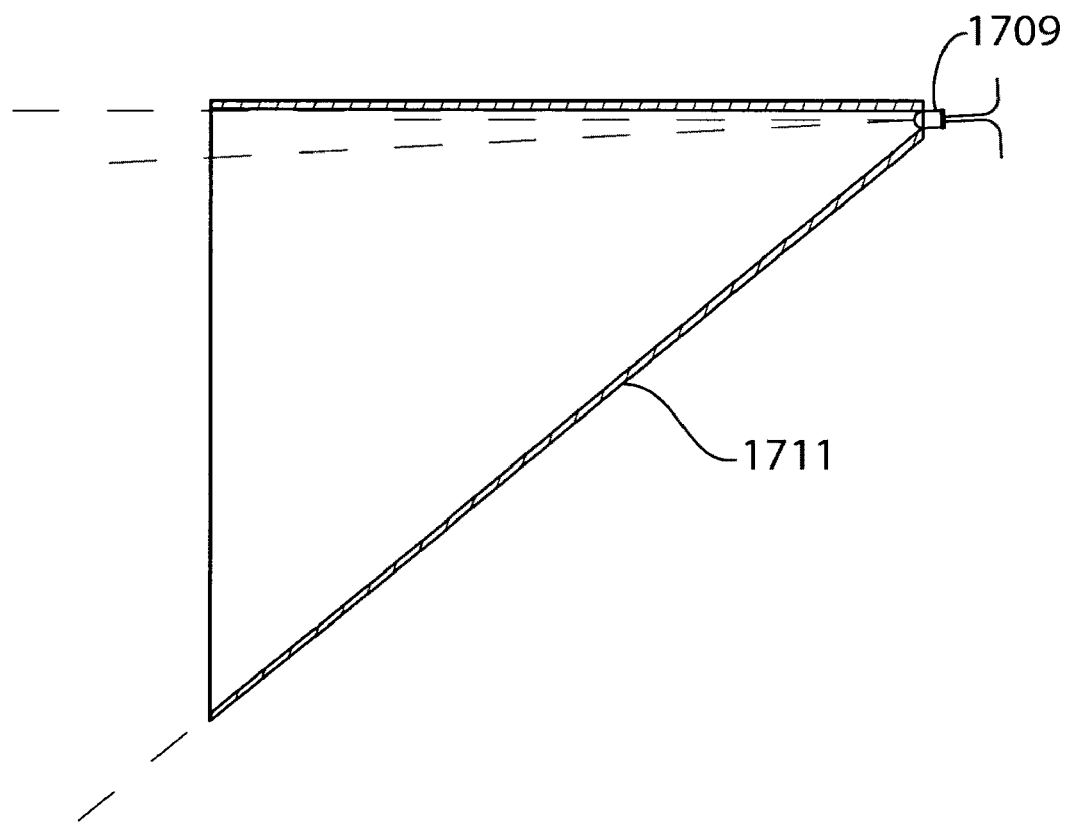
FIG. 18B illustrates a cross-sectional view of the collimator of FIG. 18A.

An embodiment of a collimator 1711 of the present invention is illustrated in FIG. 18A along with a corresponding cross-sectional view in FIG. 18B. The collimator walls restrict the field of emission of the infrared LED as well as providing controlled scattering of the infrared emissions in order to provide even infrared light distribution across the field of emission. The collimator 1711 is provided with keyhole slots 1711a to engage complementary pins, not shown, in the dust cover 1713.

Figure 19:
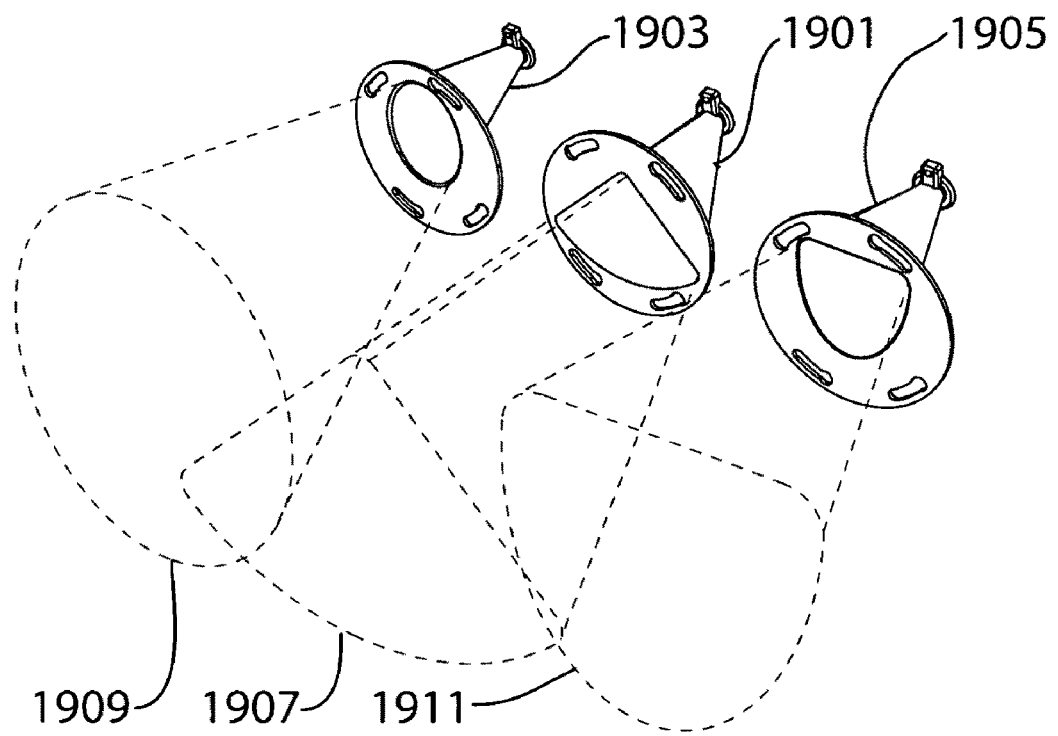
FIG. 19 illustrates exemplary embodiments of various shapes of collimators and the resulting IR emission patterns.
Figure 20:
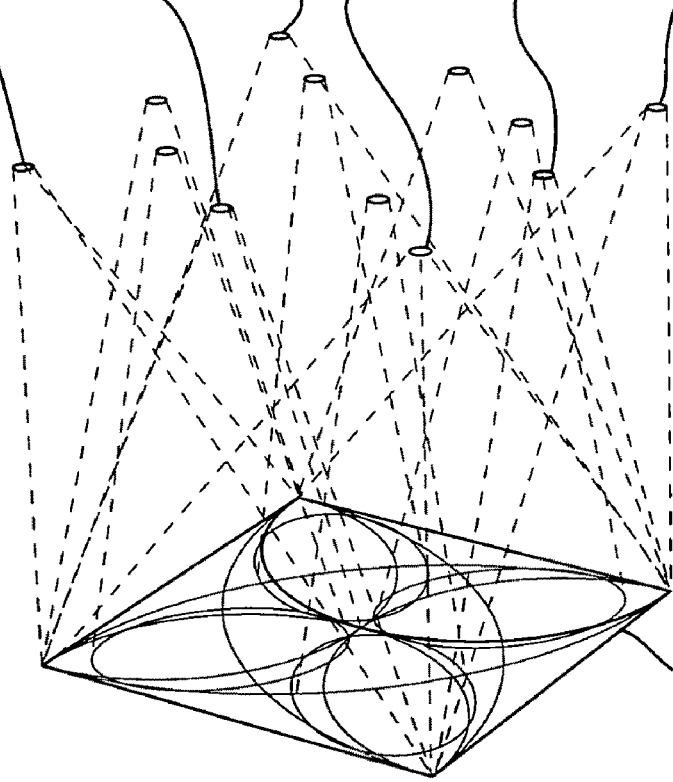
FIG. 20 illustrates an exemplary array of collimators and the resulting cubic zone they define.

FIG. 19 illustrates exemplary embodiments of various shapes of collimators and the resulting IR emission patterns. Thus, collimator 1903 provides a generally circular emission pattern 1909, collimator 1901 provides a generally fan-shaped emission pattern 1907, and collimator 1905 provides a generally semicircular emission pattern 1911. These collimator cones can be combined into an array mounted on a ceiling, to define a cube-shaped zone 1913 for example with well-defined boundaries as shown in FIG. 20. Other shapes of zones having well-defined boundaries can be defined by using different arrays of collimator cones. Well defined boundaries are advantageous when adjacent zones are in close proximity such as for example and adjacent patient beds in a hospital ward.

Figure 21:
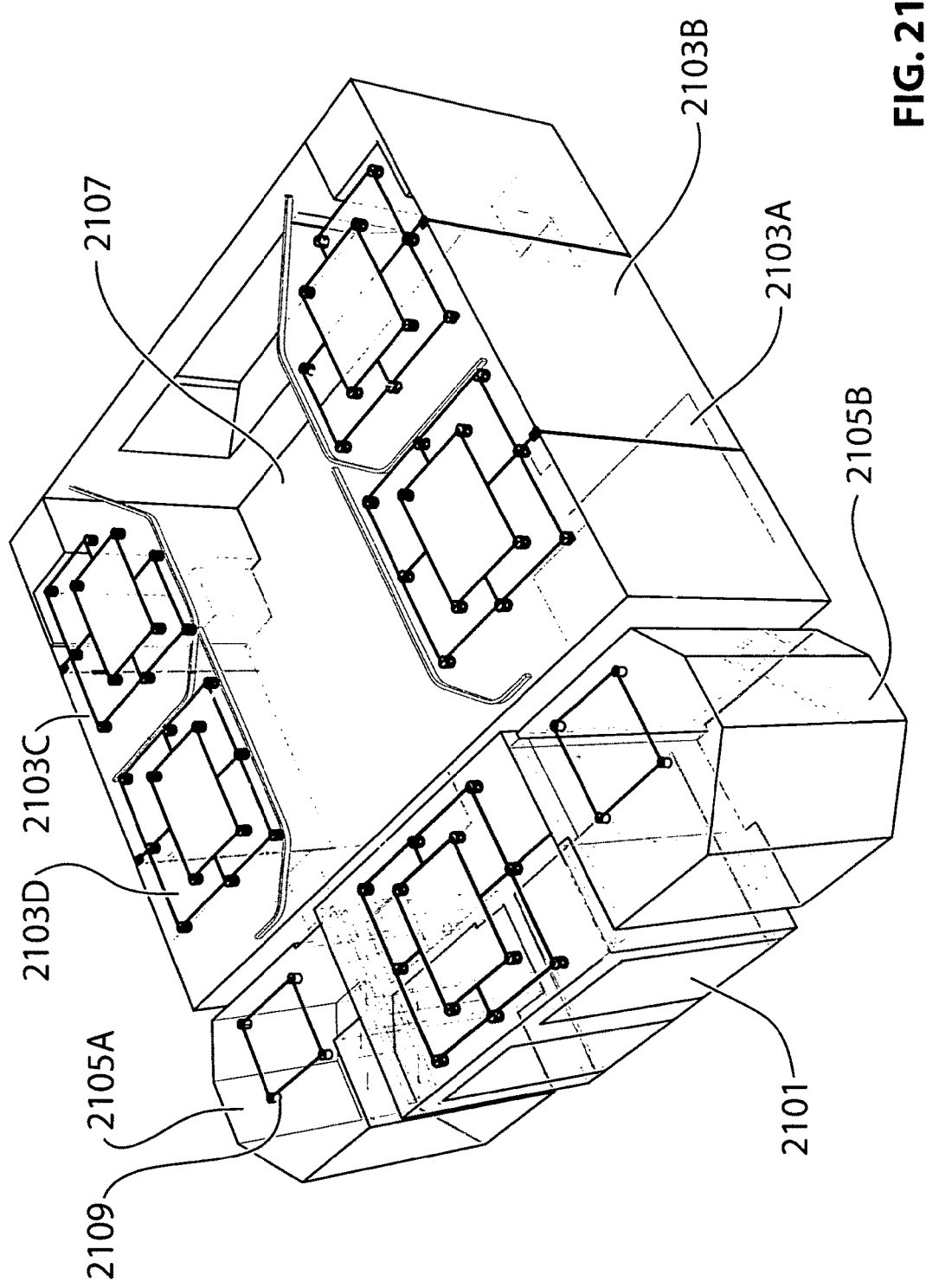
FIG. 21 is a perspective view of an area of an exemplary health care facility illustrating various zone types.

FIG. 21 is a perspective view of an area of an exemplary health care facility illustrating various zone types. In this example and entrance zone 2101 is defined at the entrance of a hospital ward. Patient zones 2103 are defined around patient beds. Bathroom zones 2105 can also be provided.

In some embodiments, zones include an array of 12 I.R. emitters housed in specially designed white plastic Collimators. The geometry of the Collimators is driven by the desired zone boundary, the distance from the floor and their respective location in the array. In a square 12 emitter array, three shapes were determined to be sufficient to provide a cubic zone of detection with a granularity of 5-10 cm. Most zone shapes can be defined by using the three shapes but accommodating a complex custom zone boundary might require custom collimators. While the IR emitters provide effective zone boundaries or delineations, there may be other configurations that enable similar zone boundaries. For example, modules may be available which are one or two dimensional, that is are capable of emitting a signal around or over an area or along a line and which are capable of drawing patterns or lines using visible red semiconductor lasers, such as those which are used in virtual keyboards and laser levels.

Figure 22:
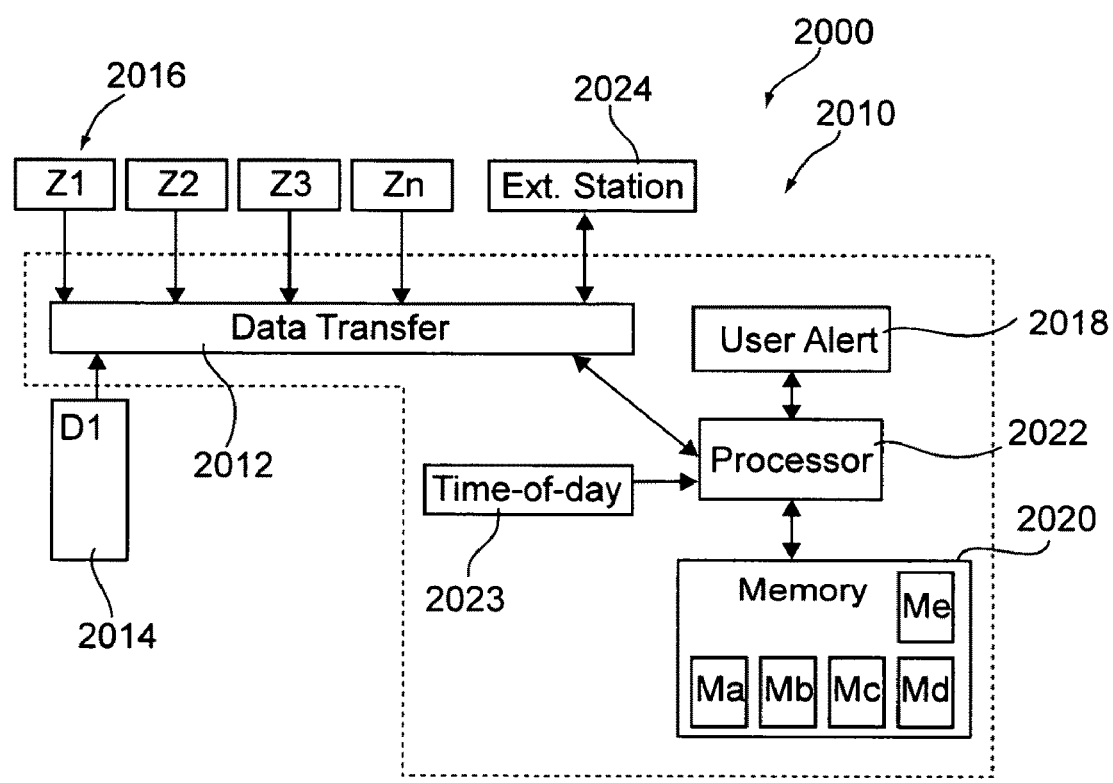
FIGS. 22, 22a and 23 to 28 are schematic views of other exemplified hygiene monitoring systems and components thereof.

Another example is shown in FIG. 22 which schematically illustrates a system 2000 employing a number of smart zone sensors, in this case referred to as a number of wearable monitoring units, one of which is shown at 2010. The monitoring unit 2010 includes a data transfer portion 2012, which may be provided by one or more discrete data transfer units, such as transmitters, receivers, transceivers, or data transfer ports such as RS232, USB, Bluetooth, 802.11 and the like. The data transfer portion 2012 is operable for receiving sensory data reporting a hygiene event, in this case from a hygiene detector 2014, and zone data from one or more zone beacons shown at 2016, the zone data including zone location data and/or zone type data.

Figure 23:
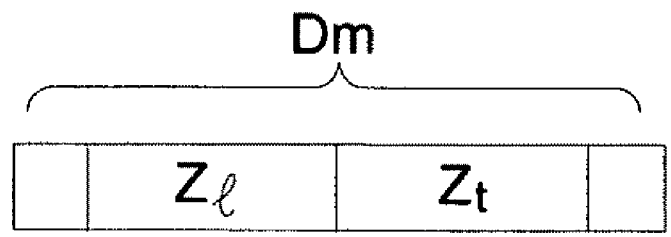

A user alert portion is provided at 2018 for issuing one or more hygiene alert signals for instructing an active attendant, wearing the monitoring unit, to carry out a hygiene event. A memory portion is provided at 2020 to store data for use during operation of the monitoring unit. As shown in FIGS. 22, 23, the memory portion includes a first memory segment Ma to store the sensory data and a second memory segment Mb to store a group of hygiene status subroutines HS1, HS2, HSn, each according to a corresponding infection risk level L1, L2, Ln. The hygiene status subroutines provide predetermined alert signals to the attendant wearing the unit depending on the risk level. Thus, the memory portion 2020 may be a single memory chip or the like or may include more than one memory chip or other memory element, such as a hard drive, or the like.

A monitor processor is also provided at 2022 which is configured to receive at least one zone data message from one of the zone beacons 2016, to decode the zone data message to identify a zone location data portion Zl and/or the zone type data portion Zt, to select one of a number of available hygiene status subroutines HS1 to HSn, according to a zone type data portion Zt and an infection risk level L1 to Ln, or a correlation therebetween, and then execute the selected hygiene status subroutine. Thus, the monitor processor may select one of the number of hygiene status subroutines based on a specific geographical location, such as a monitored zone around a hospital bed, as would be indicated by the zone location data portion alone, or alternatively on a general geographical location, such as in a hallway, as would be indicated by a zone type data portion, for instance in the absence of a zone location type indicating a specific location in the hallway. There may be instances where the monitoring unit may select one of a number of available hygiene status subroutines HS1 to HSn, according to correlation between the zone type data portion Zt and the selected hygiene status subroutine, without an infection risk level. For instance, the zone type data portion may be an infection risk level.

In this example, the first subroutine HS1 includes an instruction to issue an alert signal and the user alert portion 2018 is responsive to the monitor processor issue the alert signal.

Selected hygiene alert subroutines HS1 to HSn include instructions to issue a hygiene alert message and the user alert portion is responsive to the hygiene alert message from the monitor portion for issuing one or more hygiene alert signals to the user. In this case, the user alert portion 2018 may issue two or more different hygiene alert signals, on instruction from the monitor processor.

As shown in FIG. 23, this means that the monitor processor may be configured, in the case of a first zone data message Dm, to decode the message to identify a first zone location data portion Zl and/or a first zone type data portion Zt and then select a first hygiene status subroutine (such as subroutine HS1) according to an indexed correlation with the first zone location data portion and/or the first zone type data portion. Next, the monitor processor may be configured, in the case of a second zone data message which is different from the first zone data message, to decode the message to identify a second zone location data portion and/or a second zone type data portion and then select, and execute, a second hygiene status subroutine HS2 according to an indexed correlation with the second zone location data portion and/or the second zone type data portion.

In this case, the first and second subroutines HS1 and HS2 may apply to different infection risks. For instance, the second subroutine HS2 may have a lower infection risk level than the first subroutine HS1 and the lower risk level may not require an alert signal. In this case, the user alert portion will not issue a second signal as a result of the second subroutine. On other hand, the second subroutine may have a higher infection risk level than the first subroutine and the higher risk level may include an escalated second alert signal when compared with the first alert signal.

If desired, the memory portion 2020 may also include a third memory segment Mc to store zone location data Zl for a plurality of predetermined zone locations and/or zone type data for a plurality of predetermined zone types; and a fourth memory segment Md to index correlations between each of the hygiene status subroutines and one or more of the predetermined zone locations Zl and/or one or more of the predetermined zone types Zt. It may be useful, in this case, to associate each location in the facility with a risk level.

If desired, the data transfer portion may also be operable for transferring user identity data and/or activity history data between the monitoring unit and an external station 2024. In this case the memory portion 2020 may be partitioned or otherwise arranged to include a fifth memory segment Me to store the activity history data.

If desired, the processor 2022 may also include, or interact with, a time-of-day module 2023 to associate a user activity with a particular time of day in which the activity is carried out. For instance, a bath activity for a patient at noon in a busy ward on a weekday may require involve greater risk to the patient and others in the facility, when compared with a bath activity that occurs in a quieter ward setting, for example after visiting hours on a Sunday evening. In this case, the monitor processor may receive a time-of-day signal from the time-of-day monitor and make an adjustment to the risk level normally associated with the activity question, thus changing the hygiene status protocol employed.

Figure 5:
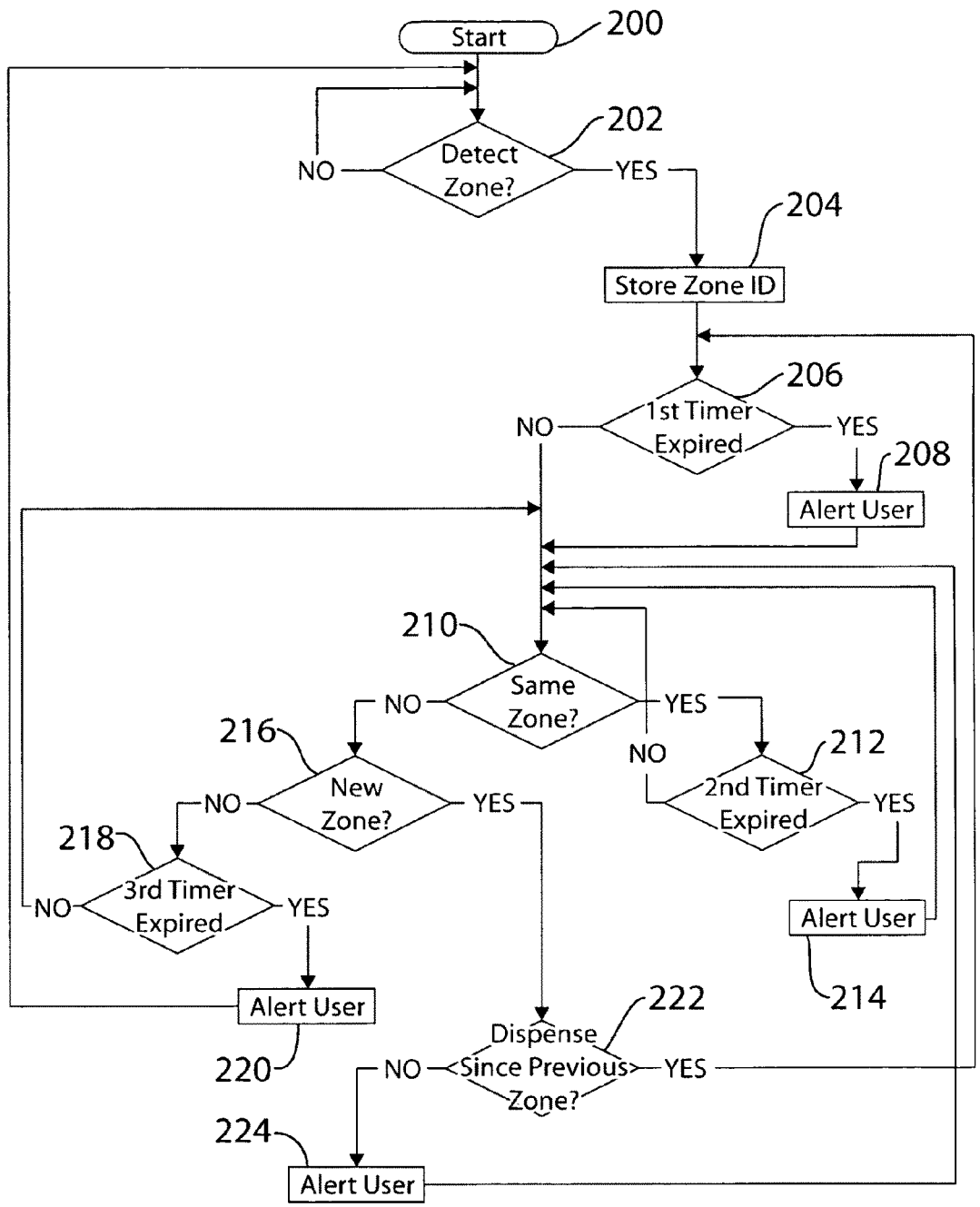
FIG. 5 is flowchart illustrating another embodiment of the present invention.

FIG. 5 illustrates one example of a group of hygiene status subroutines, involving three timers. Other hygiene status subroutines may also be configured with one, two, three or more timers as desired, depending on the circumstances. Several examples of hygiene status subroutines falling under the group shown in FIG. 5 follow:

EXAMPLE

Selection of Infection Risk Level-Dependent Subroutine Upon Entrance to a Monitored Zone with a Patient Infected with MRSA Category: Emphasized Prompting Upon Leaving an Area
Protocol: Providing care for individuals with MRSA places special emphasis on ensuring that caregivers comply with thorough measures for preventing the spread of the disease. This includes disposing of garments worn while in contact and/or proximity to the MRSA infected individual and hand disinfection upon exiting the patient's area.
Details:
1. Caregiver walks into a monitored zone
2. Wearable unit receives data message from zone beacon 3. Wearable unit decodes data message to identify zone location and zone type
4. Wearable unit identifies zone location and/or zone type as having a high infection risk level due to the presence of MRSA
5. Wearable unit (processor module) selects a status subroutine with an enhanced ability to detect when the caregiver exits a zone (eliminating or reducing the time window currently provided before the wearable unit acknowledges a zone exit).

In this case, the third timer would be set to a time that is appropriate for these circumstances of the patient. Where the third timer may be set at ten minutes in one lower risk level example, it may alternative be set at two minutes under these circumstances.

EXAMPLE

Selection of Infection Risk Level-Dependent Subroutine Upon Entrance to a Monitored Zone with a Patient with a Compromised Immune System Category: Emphasized Prompting While in an Area Protocol: Providing care for immunocompromised individuals places special emphasis on ensuring that caregivers comply with thorough measures for preventing the contamination of the patient's area with pathogens from other zones. This includes hand disinfection upon entering the patient's area.

Details:
1. Caregiver walks into a monitored zone
2. Wearable unit receives data message from zone beacon
3. Wearable unit decodes data message to identify zone location and zone type
4. Wearable unit identifies zone location and/or zone type as having a high infection risk level due to the presence of a person with a compromised immune system
5. Wearable unit (processor module) selects a status subroutine with and enhanced ability to prompt the caregiver while inside the zone (reducing the time window currently provided before the wearable unit emits a prompt while inside a zone).

In this case, the first timer would be set to a time that is appropriate for these circumstances of the patient. Where the first timer may be set at two minutes in one lower risk level example, it may alternative be set at 10 to 40 seconds under these circumstances.

EXAMPLE

Selection of Infection Risk Level-Dependent and Task-Dependent Subroutine Upon Entrance to a Monitored Zone with a Patient with a Compromised Immune System Category: Emphasized Prompting While in an Area Protocol: Providing care for immunocompromised individuals places special emphasis on ensuring that caregivers comply with thorough measures for preventing the contamination of the patient's area with pathogens from other zones. This includes hand disinfection upon entering the patient's area and through hand cleansing after assisting in toileting activities.

Details:
1. Caregiver walks into a monitored zone
2. Wearable unit receives data message from zone beacon
3. Wearable unit decodes data message to identify zone location and zone type
4. Wearable unit identifies zone location and/or zone type as having a high infection risk level due to the presence of a person with a compromised immune system
5. Wearable unit (processor module) selects a status subroutine with and enhanced ability to prompt the caregiver while inside the zone (reducing the time window currently provided before the wearable unit emits a prompt while inside a zone) and with the ability to prompt after changing an incontinence pad.

In this case, the second timer would be set to a time that is appropriate for these circumstances of the patient. Where the second timer may be set at two minutes in one lower risk level example, it may alternative be set at 10 to 40 seconds under these circumstances.

Figure 22A:
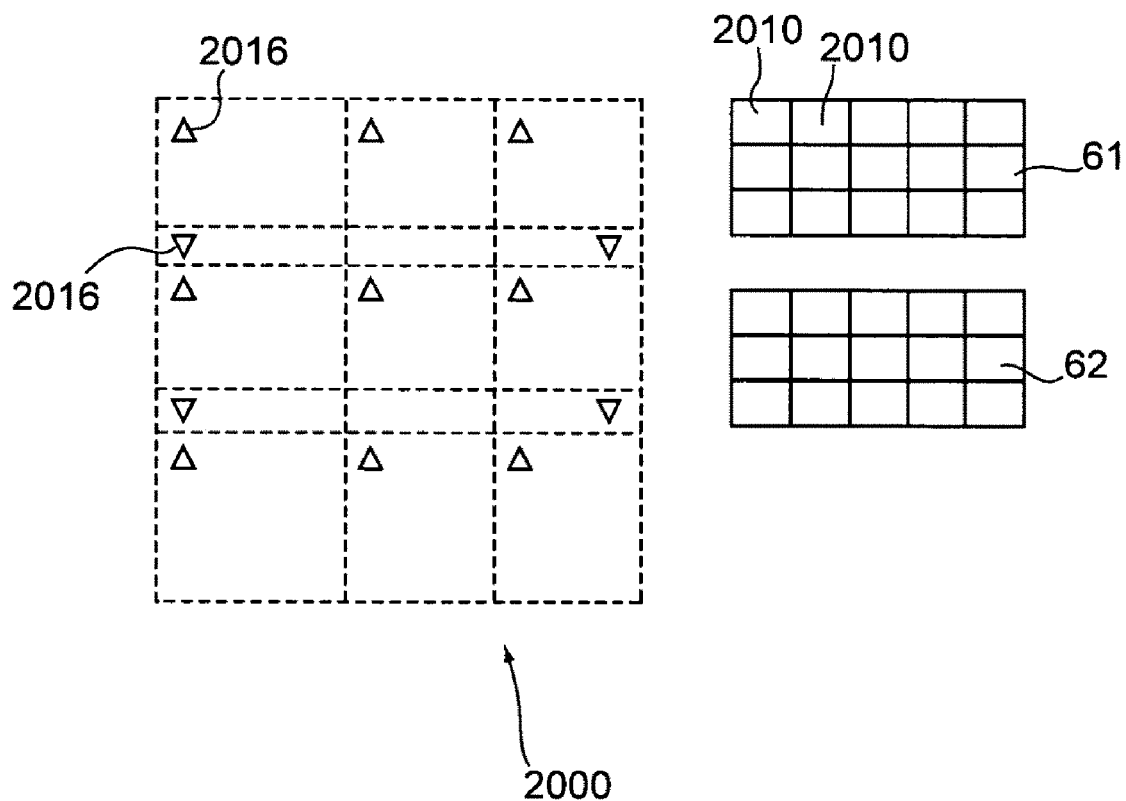

FIG. 22a illustrates the wearable monitoring units in two groups, a first group of wearable monitoring devices G1 for a first group of human attendants, and the memory portion in each of the first group of wearable monitoring devices being operable to store a first group of hygiene status subroutines and unique to the first group, and a second group of wearable monitoring devices G2 for a second group of human attendants, the memory portion in each of the second group of wearable monitoring devices being operable to store a second group of hygiene status subroutines and unique to the second group.

Figure 24:
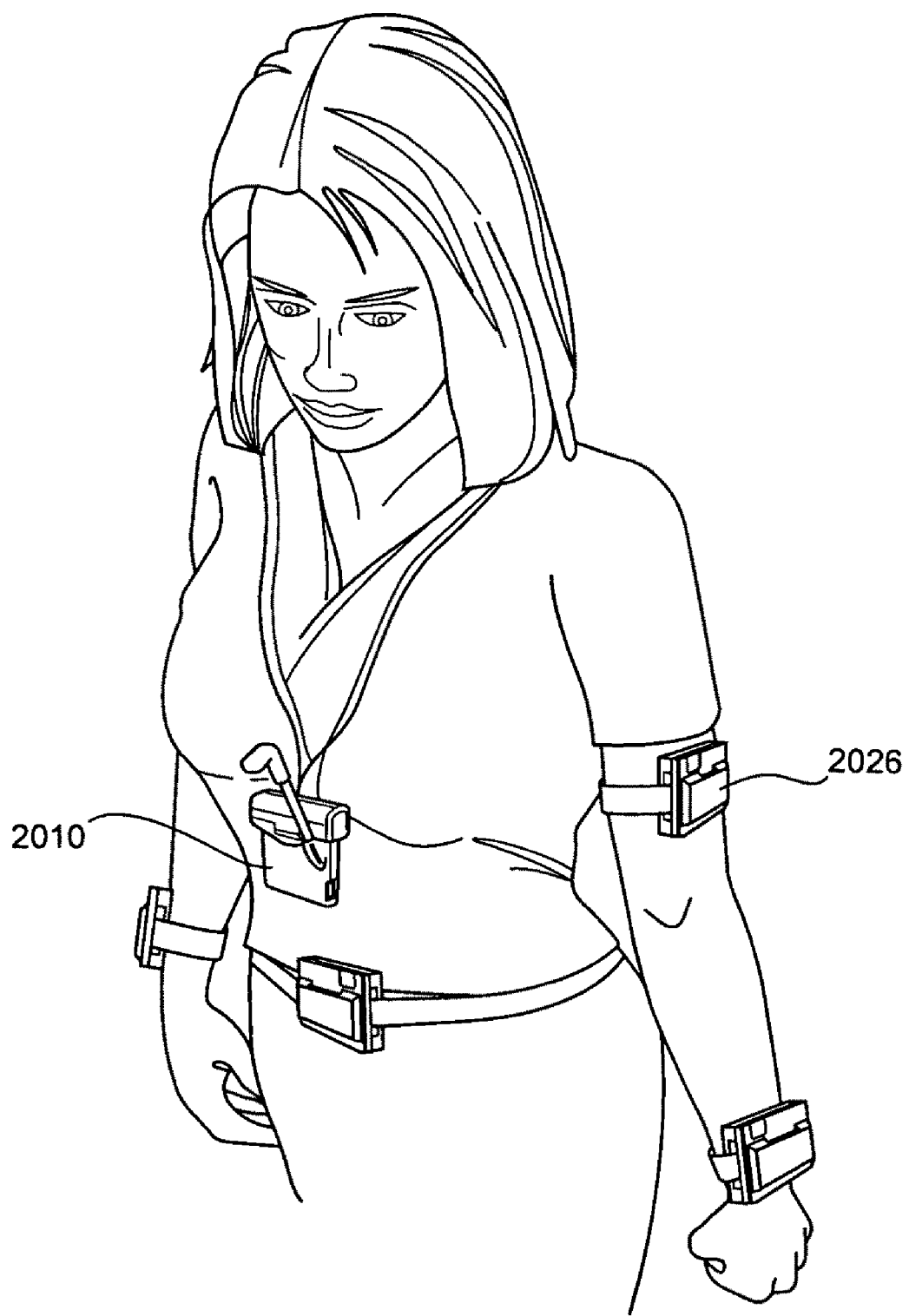
Figure 25:
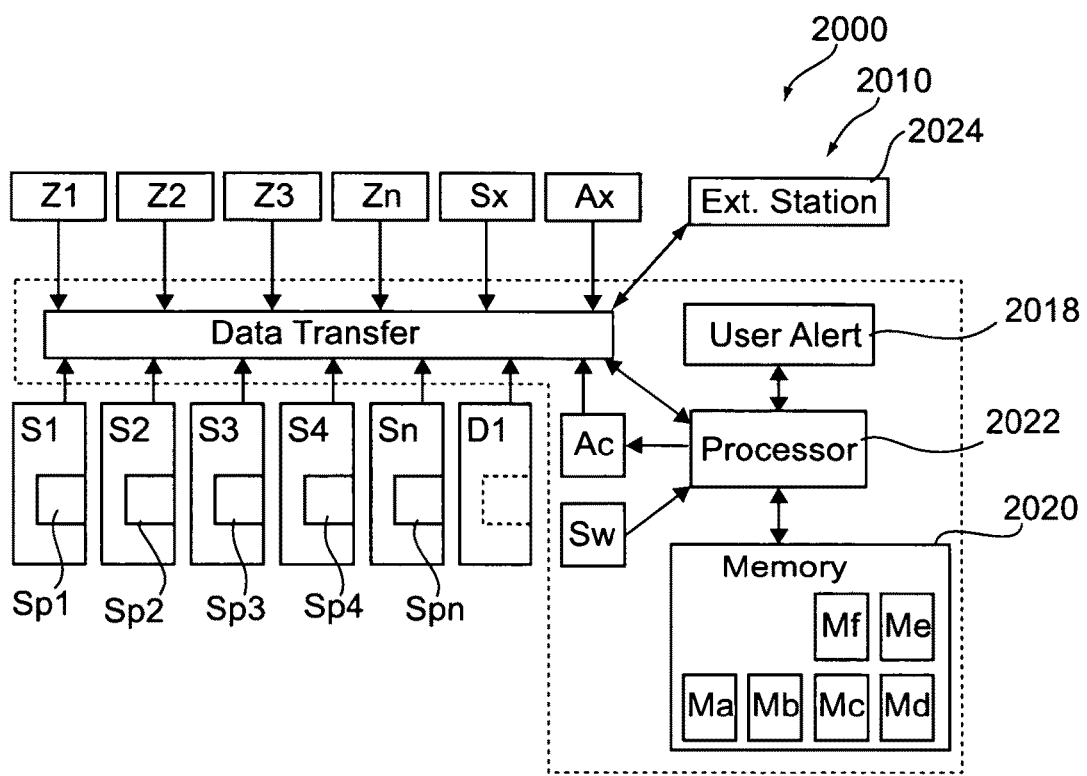

Another example of the system 2000 is shown in FIGS. 24, 25. In this case, the wearable monitor unit 2010 is capable of making relatively more intelligent decisions on when and if to issue an alert signal. This additional intelligence is provided by way of the monitor processor 2022 which is configured to predict, analyze and/or forecast an activity by the attendant wearing the monitoring unit.

In this case, the data transfer portion 2012 is operable for receiving sensory data from a number of sensors shown at 2026 issuing signals of one or more descriptors or features of an activity of the attendant wearing the monitoring unit. The sensors in FIG. 24 are merely examples and may be provided in smaller housings as desired. Also provided are a number of feature space data structures stored in the memory portion 2020 which are formed to model a "template" activity of the attendant, based on past examples of the activity. Each feature space data structure may thus model a single activity, or a group of activities involving certain common activity features. The feature space data structures may be based on a generic sampling of test subjects by carrying out the activities in question, to establish a generic set of feature space data structures for a class of users of the monitoring or on a specific set of feature space data structures for a specific user of a specific monitoring unit and assembled through a training mode, as discussed above. Also provided is an activity module Ac which serves as a current activity identifier to allow for an authorized entity, be it a user of the monitoring unit, a technician assisting the user, or a supervisory representative or function overseeing a particular function, to determine or verify that the monitoring processor has in fact correctly identified an activity. This activity module may include an audio signal, such as a beep, or a synthesized or pre-recorded voice message, or a visual signal, such an LED, LCD or other illuminating element, or the like, or a bank of LED's, each identifying a predetermined activity, or an electronic signal to be relayed to an external station either for redirecting an audio or visual or for analyzing the signal for further action. In the latter case, the activity module Ac may thus communicate with the data transfer portion.

Figure 26:
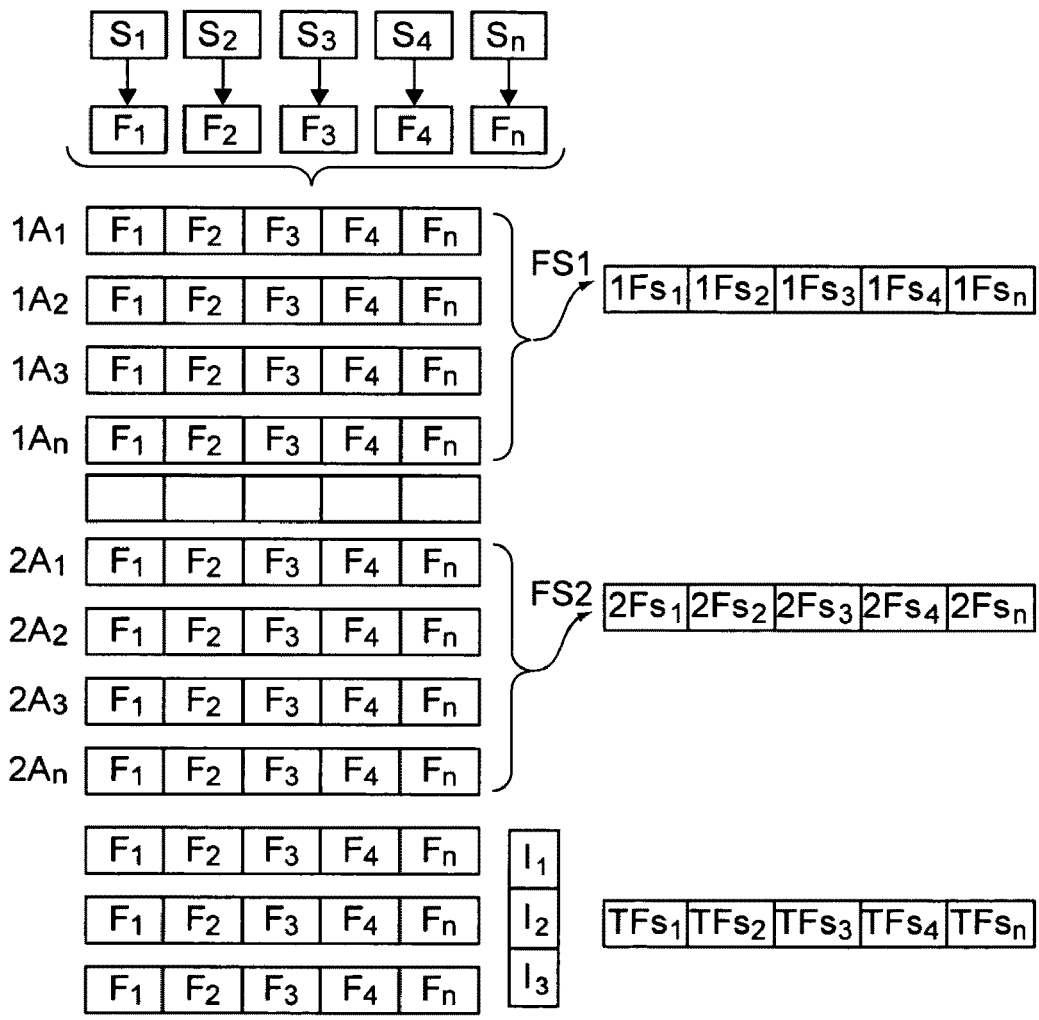

Thus, for one example of the teaching mode as shown in FIG. 26, the monitor processor is configured to receive sensory data in the form of feature coordinates F1, F2, F3, F4, Fn, from one or more sensors S1, S2, S3, S4, Sn, recording a number of repeated instances of a first current attendant activity, such as "administering a needle", generate a first series of current activity feature data sets 1A1, 1A2, 1A3, 1An, for the first current attendant activity; and then generate a feature space data structure FS1 modeling the first series.

Then, for a second activity, such as "going to the bathroom", the monitor processor may receive sensory data recording a number of repeated instances of the second current activity, generate a second series of current activity feature data sets 2A1, 2A2, 2A3, 2An, for the second current attendant activity and generate a feature space data structure FS2 modeling the second series.

The monitor processor then is configured to associate, or be instructed to associate, each data structure with a corresponding hygiene risk level to form a number of associations. The monitor processor is thus configured to repeat these steps for as many activities as needed.

The memory portion 2020 is thus provided with a sixth segment as shown at Mf in FIG. 25 to store the feature space data structures for the first and second series and the associations, as well as other series and associations as desired.

In this example, the sensory data being received by the monitor processor may be processed or raw sensory data. In other words, the raw data may be received by the data transfer portion 2012 as a feature coordinate and as a direct output from a sensor element, such as a temperature gauge, in an integer format in this case. On the other hand, the processed sensor data may be received by the data transfer from another processor which in turn receives raw, or unprocessed, data from a sensor and performs one or more calculations or subroutines on the data to generate one or more feature coordinates.

The monitor processor 2022 is, in this example, configured to receive the sensory data to generate at least one current activity feature data set for a current attendant activity, associate the current activity feature data set with the feature space data structures to generate a correlation between the feature data set and one of the feature space data structures; select an infection risk level according to the correlation; elect a hygiene status subroutine from the list of hygiene status subroutines according to the infection risk level; and execute the selected hygiene status subroutine.

In yet another variation, as shown in FIG. 26, the monitor processor is configured to form a group of identities I1, I2, I3, for a corresponding number of successive current attendant activities and then store the identities. The monitor processor is then operable to predict a next attendant activity based on the stored identities. The monitor processor is then operable to select an infection risk level according to the next attendant activity; and thereafter carry out a corresponding hygiene status subroutine in advance of the next attendant activity based on the selected infection risk level.

In this case, the sensors S1, S2, S3, S4, Sn are configured for issuing a signal to the data transfer portion, with the signal carrying the sensory data of one or more descriptors of activity of the attendant wearing the monitoring unit.

The sensors may include an accelerometer, thermometer, microphone, elevation meter, pressure meter, motion sensor, global positioning device and/or a gyroscope. Some of the sensors may themselves include a sensor processor shown at Sp1, Sp2, Sp3, Sp4, Spn, as shown in FIG. 25, which are themselves configured to generate one or more predetermined feature coordinates F1, F2, F3, F4, Fn and the monitor processor is configured to generate the feature data set according to the one or more feature coordinates.

The hygiene event may include a hand wash disinfectant activation, a hand wash sink activation, a soap dispenser activation, a towel activation, a glove dispenser activation and/or blower activation, among others. These are collectively identified by the external sensor Ax.

One or more of the sensors may measure one or more signals of, or relating to, the attendant activity, including temperature and/or sound. One or more of the sensors may measure angular or linear acceleration, speed, position and/or distance the feature coordinates including, but not limited to, mean, standard deviation, energy and/or axis correlation.

The sensor processor, for those sensors employing one, may be configured to carry out a range of programs or subroutines according to a range of algorithms for the correlation step, based on hardware, firmware or software, including one or more pattern recognition subroutines.

One or more of the feature coordinates may include one or more time domain features coordinates, including, but not limited to, root mean square (RMS), integrated RMS, mean absolute value (MAV), mean absolute value slope (MAVSLP), zero crossing (ZC), waveform length, variance, number of slope sign changes and/or amplitude histograms.

One or more of the feature coordinates may also include one or more frequency domain features coordinates including, but no limited to, spectral representations of the signal, the spectral representations including Fast Fourier Transform (FFT) coefficients, autoregressive (AR) coefficients, and/or cepstral coefficients.

The feature coordinates may also include one or more time-frequency features including, but not limited to, short-time Fourier transform (STFT) coefficients, wavelet coefficients and wavelet packet coefficients.

The monitor processor may also be configured to carry out a range of programs or subroutines according to a range of algorithms for the correlation step, based on hardware, firmware or software, including one or more pattern recognition subroutines. In this case, the monitor processor is responsive to the sensor processors to receive a plurality of feature coordinates therefrom and to generate the feature data set.

The monitor processor may be further configured to employ a dimensionality reduction subroutine to reduce the number of feature coordinates in the plurality of received feature coordinates in the generated feature data set.

The monitor processor may also be configured to employ a supervised and/or an unsupervised classification subroutine including for example:
Linear classifiers such as Linear Discriminant Analysis,
Decision Tables,
Decision Trees (C4.5),
k-Nearest Neighbor,
Support Vector Machines (SVM),
Hidden Markov Models,
Artificial Neural Networks,
Fuzzy and neuro fuzzy classifier, and
Clustering.

In some cases, an association between the feature data set and the feature space data structures may be sufficiently unrecognizable, that a correlation is not possible, is unclear, or has a relatively low confidence interval. In this case, the monitor processor may be configured to employ one or more a "majority vote"-type subroutine or other subroutine to resolve conflicts between a current feature data set and a corresponding feature space data structure. For instance, it may be that most but not all of the feature coordinates have a match with corresponding sectors in the feature space data structure, in which case those correlating feature coordinates "out vote" the feature coordinates without a correlation.

The feature coordinates collected by the monitor processor can also be considered coefficients for a vector, where the feature data set may also be considered a feature vector and the feature space data structure may also be considered to be a feature vector space.

Thus, the monitor processor is capable of storing feature space data structures, which in one example can be in the form of store a vector space values for a predicted attendant activity. The monitor processor may thus also be configured to receive the sensory data to assemble at least one current activity vector value for a current attendant activity and then to associate the current activity vector value with the vector space values to generate a correlation. In one instance, the correlation may be a mathematical match, within a predetermined confidence interval.

Figure 27:
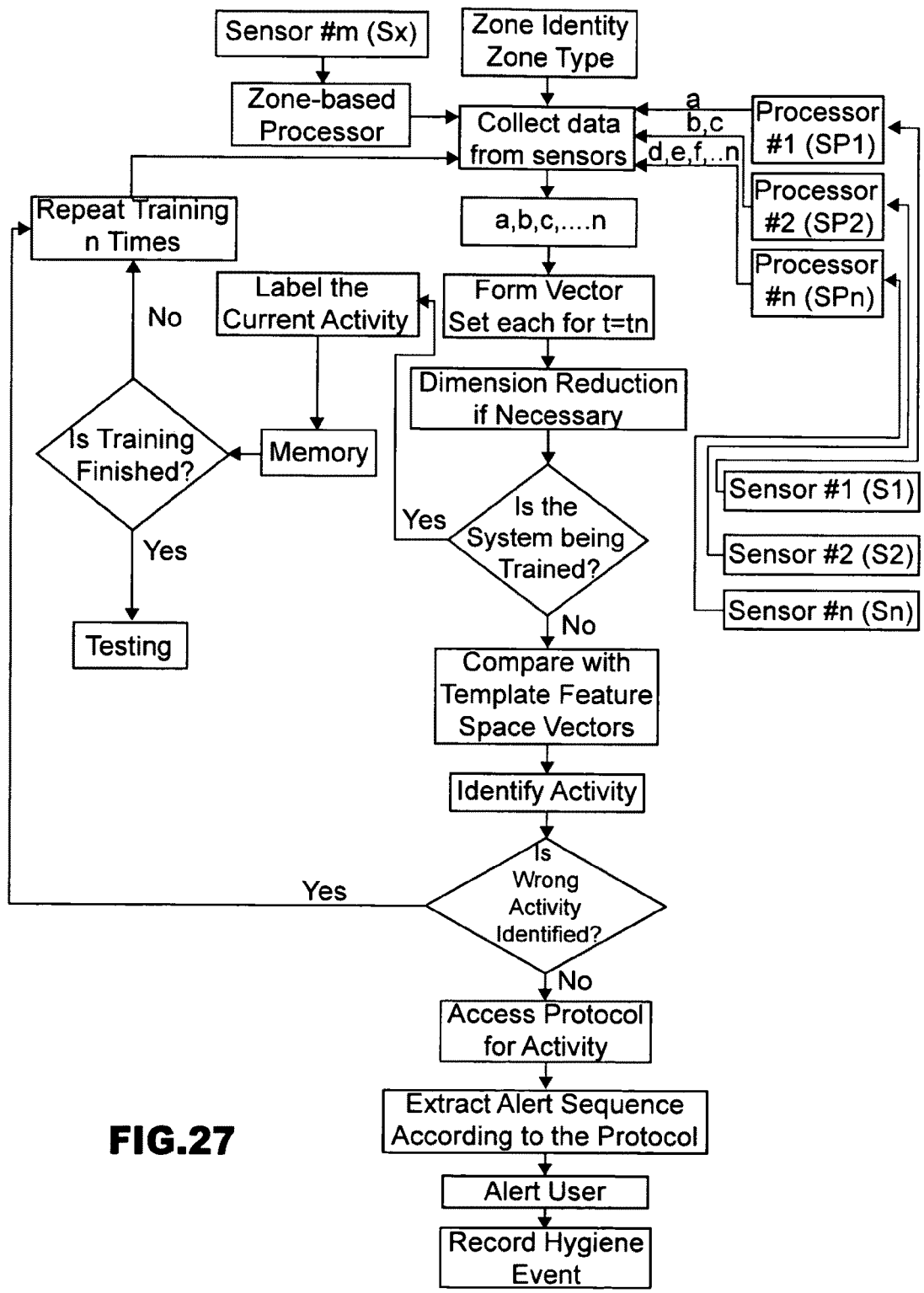

Referring to FIG. 27, the operation of the system 2000 is as follows. First, the processor receives a zone data signal and decodes the zone identity and zone type signal portions. The monitor processor also collects feature coordinate data from the various sensors via their corresponding sensor processors to form the activity feature data set. Depending on the number of feature coordinates, the system may then employ a dimension reduction procedure as described above. If desired, the sensors may also send raw data to the monitor processor so that the monitor processor may calculate and extract the features therefrom. In this case, the sensors sending raw data may themselves not be required to have a processor.

The monitor processor then asks if the system is being trained. This state may be established by a manual or electronic switch function onboard the monitoring unit, such as the switch module shown at Sw, as deployed by an attendant, by an assisting technician, by supervisory personnel, or by an automated server function through a wireless or wired communication link to the monitoring unit. If the status of the switch function indicates yes, the feature data set for the current activity is labeled, such as by 1A2 above and the feature set is recorded in memory. With the feature data set labeled and stored, the monitor processor then asks if the training is finished. This would be indicated by a counter recording the number of instances of the formation of the data set for the current activity. The counter would be advanced by the storing of the data set in memory or by some other event either in advance of, for following, the storing of the data set in memory. The current counter value would then be compared with a test count value and, provided that the current counter value is less than the test count value, the monitor processor would then advance to the collection step. If the current counter value equals the test count value, meaning that training is finished, the monitor processor then advances to a testing subroutine, which may include a number of trial activities or a set up for a number of preset activities to see how the monitoring is functioning. If the system is not being trained, the monitor processor compares the feature data set with the feature space data structures stored in memory to look for a correlation, resulting in identifying an activity.

The monitor processor then queries if the activity is the wrong activity. This is done by the monitor processor issuing, or instructing the issuance of, a query signal, via the identity module to an authorized entity, as described above. The authorized entity then confirms if the activity is the wrong activity. If yes, a training routine is repeated, causing the system to advance to the collection step #. If no, the monitor processor then accesses the hygiene status subroutine that corresponds to the infection risk level for the identified activity and executes the hygiene status subroutine which, depending on the subroutine, leads to a user alert. The monitor processor then waits for a signal recording a hygiene event.

The two examples of the system benefit from the ability of the hand wash monitor units to make intelligent decisions in order to reduce the number of "hand washings" that would otherwise have to occur without the intelligence.

For instance, if a nurse were to wash her hands each time she enters and leaves a patient area, she may be hand washing a great many times a day. Clearly, success in hand washing (or other hygiene) compliance and cost controls may be enhanced when the monitoring unit is able to make informed decisions about just when the hand washing has to occur.

To achieve this, in one example, the hand wash monitoring unit may taught so that it can make judgments about when to identify a hygiene event and, if so, by which alert, and, if so, for which hygiene mode or procedure (such as putting on, or taking off, protective gloves).

To this end, in one example, the hand wash monitoring unit includes the ability to record a number of local "attributes" and thus to obtain a signature for the attributes, and then to evaluate the signature, or group of signatures, over a predetermined time interval, to identify a predetermined regular activity.

A regular activity might be attending a toilet with a patient, with the monitoring unit sensing a change in the orientation of the torso of the user (i.e. that the user is bent over) and sensing the sound (i.e. of a flushing toilet). Another predetermined regular activity might be attending to a patient in bed (bent over, no echoes), or walking, running, eating, or doing filing. And in each event, the sensor would be in a position to assess if hand washing is needed thereafter and, if so, determine when the hand washing (or other hygiene procedure) should occur. The monitoring unit may then alert the user accordingly.

The system may thus track not only the entrance into a sensed zone but the departure from one zone and the arrival at another zone, by tracking two beacons in succession, thereby indicating direction.

A collection or suite of signature plots may then be assembled for each predetermined activity, each signature plot for each attribute of the activity, or for the activity itself. These may then be loaded on the hand wash monitoring unit as "template" signatures. The hand wash monitoring unit may then:

i) collect data for each attribute from each sensor over a predetermined sensing period;
ii) form a "current" signature for each attribute (or a composite "current" signature); and then
iii) compare the "current" signature with the stored signatures, such as by a statistical best fit analysis to match the signatures with any one of the stored signature sets to approximate or predict the current activity.

Once the hand wash monitoring unit has identified the activity, it may then consider what hygiene activity needs to be undertaken.

Of course, the activities carried out by people in the hygiene-monitored environment will vary with their job description. A custodian will have a different set of activities to a nurse, and in turn a doctor. Each hand wash monitoring unit may then be loaded, if desired, with a different suite of signatures according to their role in the facility.

The zone beacons may then provide a number of geographical markers and patient identifiers or other locational identifiers that may be relevant to selecting a hygiene protocol. The hand wash monitoring unit may then do the processing, all at the local level, reducing bandwidth in the internal network of the facility in question that would otherwise be necessary, if the processing were being done at a central server.

The local processing capability of the hand wash monitoring unit gives it the capability to ask more questions about its own environment and make more informed decisions on when (and indeed if) a user needs to wash hands, rather than relying entirely on nearby zone beacons to issue signals providing the hand wash monitoring unit a useful, though relatively limited, view of what's going on. Rather, the hand wash monitoring unit looks to the zone beacons for location and type information to describe the specific zone environment and to its own local mobile resources by way of sensors worn by the user and to other external sensors, as necessary, as shown at Sx in FIG. 25, to assess a current activity and conditions and then assess a hygiene protocol for the activity under those conditions. These other external sensors may include such things as a local video camera or microphone in a zone.

With the benefit of local processing at the hand wash monitoring unit, the processing requirements for the zone beacons are substantially reduced. They may operate on their own, once programmed, and not be part of a central network. The zone beacons may also be provided with local switching to allow the zone beacons to identify the "type" of zone. The switching may be provided at a switch location in the monitored zone, or be remotely actuated by a remote wireless switch located or accessible in the monitored zone.

The hand wash monitoring unit may then be updated or uploaded at the external station 2024 during or following a data dump stage if new protocols need to be added.

The sensors 2026 may include hybrid sensors to detect nursing activities. Accelerometers may be used to detect linear acceleration of the movement, a gyroscope to detect angular acceleration of the movement, or a microphone to detect environmental sound related to performing activities. Other sensors may also be employed to obtain more information from the environment such as temperature, air pressure, as well as physiological sensors to monitor such features as heart rate, blood pressure.

Each sensor is capable of recording raw data from the environment and sends either the processed or raw data to the wearable monitoring unit. However, in order to decrease the processing load on monitoring unit and decrease power consumption, it may be desirable to include a processing unit in each hybrid sensor and send the results therefrom to the monitoring unit.

Each hybrid sensor may communicate with the monitoring unit either by way of a wired communication path (such as a USB-HID class) or by a wireless communication path (such as the Bluetooth Class-2) It should be noted that Bluetooth Class-2 is a relatively low power wireless protocol and may be particularly desirable in healthcare settings.

Data Processing

Figure 28:
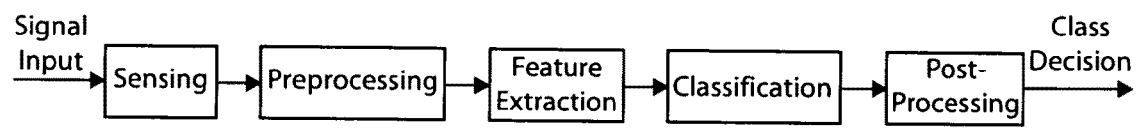

Pattern recognition may be used to identify different nursing activities. Pattern recognition is a branch of machine learning whose goal is to classify patterns into a number of categories or classes. The components of a typical pattern recognition protocol in one example are shown in the FIG. 28.

Sensing:

Each hybrid sensor may be configured to detect a different modality of nursing activity such as linear and angular acceleration, temperature and sound.

Preprocessing:

The signal quality may be enhanced for example by using filters to remove noise and/or other unwanted signals from the original signal.

Feature Extraction:

The wearable monitoring unit may thus be configured to extract discriminatory features from the signal. The extracted features thus may be used to define the feature space within which the different classifiers can be evaluated.

In terms of acceleration signal, the following is a nonexhaustive list of features that may be employed:

Mean: is the DC component of the acceleration data. This feature is mostly used to detect the body posture. Electronic tilt sensors work based on this feature.

Standard Deviation: is used for discriminating the range of possible acceleration values, which differs among different activities.

Energy: Can be used to estimate the intensity of the activity.

Correlation among axis: Features that measure correlation or acceleration between axes can improve recognition of activities involving movements of multiple body parts.

It should be noted that different signals may typically have different characteristics. For example, the characteristics of an acceleration signal may be different from those of a sound signal. Therefore, the techniques employed for extracting discriminatory features from an acceleration signal may not be effective for signal data from other sensors. The following examples of features may be explored and extracted from different signals recorded from different sensors to improve the accuracy of the system. The accuracy of the system maybe investigated by trial and error.

Time domain features. These are extracted from the temporal representation of the signal. Examples include root mean square (RMS), integrated RMS, mean absolute value (MAV), mean absolute value slope (MAVSLP), zero crossing (ZC), waveform length, variance, number of slope sign changes and amplitude histograms Frequency domain features. These features are derived from a spectral representation of the signal, including such examples as the Fast Fourier Transform (FFT) coefficients, autoregressive (AR) coefficients, and cepstral coefficients Time-frequency features. The short-time Fourier transform (STFT) coefficients, wavelet coefficients and wavelet packet coefficients are examples of features computed from a joint time and frequency signal representation.

Feature Projection:

If necessary, dimensionality reduction techniques may utilized, such as Principal Component Analysis (PCA), to be able to present the features more efficiently to the classifier.

Classification:

The task of a classifier is to assign a category to a newly observed feature. Classifications of new objects (in this example each attendant activity, such as a prescribed nursing activity) are based on a set of previously observed patterns whose true class is already known. This set is known as the training set. A classifier uses the training set to divide the extracted features into different classes.

A wide range of supervised and/or unsupervised algorithms, from simple Bayseian classifers to complex and powerful neural networks, may be used for classification, such as:

Linear classifiers such as Linear Discriminant Analysis,
Decision Tables,
Decision Trees (C4.5),
k-Nearest Neighbor,
Support Vector Machines (SVM),
Hidden Markov Models,
Artificial Neural Networks,
Fuzzy and neuro fuzzy classifier; and
Clustering.

Post-Processing

A post-processor may be employed to use the output of the classifier to decide the output function of the terminal device. The post-processor may improve system performance For example, a technique called majority vote can be used to increase the classification accuracy. In this technique, the output of each classifier is considered and the final decision is made when most classifiers agreed on a certain decision.

For example, if the accelerometers, and gyroscope classifiers (2 out of 3 classifiers) decided that the current nursing activity is 'taking blood pressure' but the sound classifier (1 out of 3 classifier) is showing the current nursing activity as "inserting an IV", the majority vote among these 3 classifiers, would claim the current nursing activity as "taking blood pressure".

The ability to predict the next nursing activity: The hand wash monitoring unit may log the history of the performed nursing activities and their corresponding hygiene events. Numerous mathematical and statistical algorithms are available to help the monitoring unit learn from the sequence/pattern of the past nursing activities and let it predict the next coming nursing activities with acceptable accuracy. Examples of such algorithms include, but are not limited to, Markov Models, Hidden Markov Models, Fuzzy systems, Neuro Fuzzy systems, and Artificial Neural Networks. For instance, if the monitoring unit recognizes that a current activity involves picking up a bed pan, the system may be able to identify that the next activity will involve installing the bed pan for use. In another example, the system may recognize a current activity as being pre-aseptic procedure, such as accessing a syringe out of a storage compartment or such as transporting a medication cart to monitored zone, thus indicative of an aseptic activity soon to follow and requiring hand washing before hand.

The entire subject matter of each of the References cited below is incorporated herein by reference:

[1] S. B. Thies, P. Tresadern, L. Kenney, D. Howard, J. Y. Goulermas, C. Smith and J. Rigby, "Comparison of linear accelerations from three measurement systems during "reach & grasp"," *Medical Engineering and Physics*, vol. 29, pp. 967-972, November, 2007. 2007.

[2] D. Roetenberg, C. T. M. Baten and P. H. Veltink, "Estimating Body Segment Orientation by Applying Inertial and Magnetic Sensing Near Ferromagnetic Materials," *IEEE Trans. Neural Syst. Rehabil. Eng.*, vol. 15, pp. 469-471, September 2007. 2007.

[3] S. M. Kidder, F. S. Abuzzahab Jr., G. F. Harris and J. E. Johnson, "A system for the analysis of foot and ankle kinematics during gait," *Rehabilitation Engineering, IEEE Transactions on*, vol. 4, pp. 25-32, March 1996. 1996.

[4] S. Henmi, K. Yonenobu, T. Masatomi and K. Oda, "A biomechanical study of activities of daily living using neck and upper limbs with an optical three-dimensional motion analysis system," *Mod Rheumatol*, vol. 16, pp. 289-293, October 2006. 2006.

[5] S. S. Rao, E. L. Bontrager, J. K. Gronley, C. J. Newsam and J. Perry, "Three-dimensional kinematics of wheelchair propulsion," *Rehabilitation Engineering, IEEE Transactions on*, vol. 4, pp. 152-160, September 1996. 1996.

[6] L. Bao and S. Intille, *Activity Recognition from User-Annotated Acceleration Data.*, vol. 3001, BERLIN: SPRINGER-VERLAG BERLIN, 2004, pp. 1-17.

[7] N. Ravi, N. Dandekar, P. Mysore and M. L. Littman, "Activity recognition from accelerometer data," in 2005,

[8] J. Lester, T. Choudhury and G. Borriello, "A Practical Approach to Recognizing Physical Activities," *Pervasive Computing*, vol. 3968, pp. 1-16, 2006.

[9] A. Nguyen, D. Moore and I. McCowan, "Unsupervised Clustering of Free-Living Human Activities using Ambulatory Accelerometry," *Conf. Proc. IEEE Eng. Med. Biol. Soc.*, vol. 1, pp. 4895-4898, 2007.

[10] D. M. Karantonis, M. R. Narayanan, M. Mathie, N. H. Lovell and B. G. Celler, "Implementation of a real-time human movement classifier using a triaxial accelerometer for ambulatory monitoring," *IEEE Transactions on Information Technology in Biomedicine*, vol. 10, pp. 156-167, 01. 2006.

[11] S. Pirttikangas, K. Fujinami and T. Nakajima, *Feature Selection and Activity Recognition from Wearable Sensors.*, vol. 4239, BERLIN: SPRINGER-VERLAG BERLIN, 2006, pp. 516-527.

[12] P. Lukowicz, J. Ward, H. Junker, M. Stager, G. Troster, A. Atrash and T. Starner, *Recognizing Workshop Activity using Body Worn Microphones and Accelerometers.* 2004,

[13] D. Minnen, T. Starner, J. A. Ward, P. Lukowicz and G. Troster, "Recognizing and discovering human actions from on-body sensor data," in (2005). 2005 *IEEE International Conference on Multimedia and Expo*(Pp. 4 Pp.). Piscataway, N.J.: IEEE. CD-ROMpp.; 2005 *IEEE International Conference on Multimedia and Expo*, 6-8 Jul. 2005, Amsterdam, Netherlands. pp. 4.

[14] R. Ohmura, F. Naya, H. Noma and K. Kogure, "B-pack: A bluetooth-based wearable sensing device for nursing activity recognition," in *Wireless Pervasive Computing, 2006 1st International Symposium on*, 2006, pp. 6.

[15] F. Naya, R. Ohmura, F. Takayanagi, H. Noma and K. Kogure, "Workers' routine activity recognition using body movements and location information," in *Wearable Computers, 2006 10th IEEE International Symposium on*, 2006, pp. 105-108.

While the present invention has been described for what are presently considered the preferred embodiments, the invention is not so limited. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

The embodiment(s) of the invention described above is (are) intended to be exemplary only. The scope of the invention is therefore intended to be limited solely by the scope of the appended claims.

We claim:

1. A wearable hygiene monitoring unit for communicating with a plurality of zone beacons each transmitting respective zone identifying data, the unit comprising:

a receiver;

an alerting unit;

a memory having stored therein a group of hygiene status subroutines; and a processor operable to receive within a given zone said zone identifying data respective thereto via said receiver;

select a particular hygiene status subroutine from said stored hygiene status subroutines according thereto;

execute the selected hygiene status subroutine and, upon user non-compliance with said selected hygiene status subroutine;

activate said alerting unit.

2. The wearable hygiene monitoring unit of claim 1, each said hygiene status subroutines corresponding to one of a number of infection risk levels, said zone identifying data identifying an infection risk level associated with said zone thereby enabling selection of an appropriate one of said hygiene status subroutines as a function thereof.

3. The wearable hygiene monitoring unit of claim 1, each said hygiene status subroutines corresponding to one or a number of zone types, said zone identifying data identifying a zone type of said zone thereby enabling selection of an appropriate one of said hygiene status subroutines as a function thereon.

4. The wearable hygiene monitoring unit of claim 1, further configured to receive, via the receiver, hygiene event data from a hygiene event detector, and process same in determining user compliance with said selected hygiene status subroutine.

5. The wearable hygiene monitoring unit of claim 1, wherein said selected hygiene status subroutine comprises at least one timer selected from a group of timers according to said zone identifying data, said at least one timer identifying a time within which the user is to complete a hygiene event for compliance with said selected hygiene status subroutine.

6. The wearable hygiene monitoring unit of claim 1, wherein said selected hygiene status subroutine comprises at least one alert selected from a group of alerts according to said zone identifying data.

7. The wearable hygiene monitoring unit of claim 1, said zone identifying data comprising zone location data and/or zone type data, said memory having stored therein a plurality of predetermined zone locations and/or zone types and an indexed correlation between said predetermined zone locations and/or zone types and each of said hygiene status subroutines, said processor further operable to select said particular hygiene status subroutine as a function of said received zone location and/or zone type and said indexed correlation.

8. The wearable hygiene monitoring unit as defined in claim 1, the processor further operable to:
receive within a new zone said zone identifying data respective thereto via said receiver,
select a new hygiene status subroutine from said stored hygiene status subroutines according thereto; and
execute the selected new hygiene status subroutine.

9. The wearable hygiene monitoring unit as defined in claim 8, wherein the new subroutine includes an instruction to issue a distinct alert via said alerting unit upon user non-compliance with said new subroutine.

10. The wearable hygiene monitoring unit as defined in claim 9, wherein the new subroutine comprises either a lower infection risk level subroutine for which said distinct alert comprises a lowered alert or no alert, a same infection risk level subroutine for which said distinct alert comprises a same alert, and a higher infection risk level subroutine for which said distinct alert comprises a heightened alert.

11. A system for monitoring hand hygiene among a number of human attendants in a facility, comprising:
a plurality of zone beacons mounted within respective zones of the facility and each transmitting zone identifying data respective thereto,
a number of wearable hygiene monitoring devices, each to be worn by an active attendant and comprising:
a receiver;
an alerting unit;
a memory having stored therein a group of hygiene status subroutines; and
a processor operable to
receive within a given zone said zone identifying data respective thereto via said receiver,
select a particular hygiene status subroutine from said stored hygiene status subroutines according thereto;
execute the selected hygiene status subroutine and, upon user non-compliance with said selected hygiene status subroutine;
activate said alerting unit.

12. The system as defined in claim 11, the number of wearable monitoring devices including:
a. a first group of wearable monitoring devices for a first group of human attendants, the memory portion in each of the first group of wearable monitoring devices being operable to store a first group of hygiene status subroutines unique to the first group, and
b. a second group of wearable monitoring devices for a second group of human attendants, the memory portion in each of the second group of wearable monitoring devices being operable to store a second group of hygiene status subroutines unique to the second group.

13. A hygiene monitoring unit wearable by an attendant in a facility for communicating with one or more wearable sensors each communicating sensory data, the unit comprising:
a receiver;
an alerting unit;
a memory having stored therein a group of predetermined attendant activity feature data sets and a group of hygiene status subroutines associated therewith; and
a processor operable to:
receive sensory data via said receiver from said one or more wearable sensors;
compare said sensory data with said stored attendant activity feature data sets to identify a current attendant activity therefrom and associated hygiene status subroutine associated therewith;
execute said identified associated hygiene status subroutine; and
upon user non-compliance with said executed subroutine, activating said alerting unit.

14. The wearable hygiene monitoring unit of claim 13, each said hygiene status subroutines corresponding to one of a number of infection risk levels, each of said group of said predetermined attendant activity feature data sets associated one of said infection risk levels, whereby said hygiene status subroutines are associated with said predetermined attendant activity feature data sets via corresponding infection risk levels.

15. The wearable hygiene monitoring unit of claim 13, further configured to receive, via the receiver, hygiene event data from a hygiene event detector, and process same in determining user compliance with said identified hygiene status subroutine.

16. The wearable hygiene monitoring unit of claim 13, wherein said identified hygiene status subroutine comprises at least one timer selected from a group of timers, said at least one timer identifying a time within which the user is to complete a hygiene event for compliance with said selected hygiene status subroutine, the unit further configured to receive, via the receiver, hygiene event data from a hygiene event detector, and process same in automatically determining user compliance with said identified hygiene status subroutine.

17. A system for monitoring hand hygiene among a number of human attendants in a facility, comprising:
a number of wearable sensor sets to be worn by respective attendants while in the facility and each set comprising one or more wearable sensors operable to communicate sensory data responsive to attendant activity; a number of hygiene monitoring units to be worn by said respective attendants, each of said units comprising:

a receiver;

an alerting unit;

a memory having stored therein a group of predetermined attendant activity feature data sets and a group of hygiene status subroutines associated therewith; and a processor operable to:
- receive sensory data via said receiver from said one or more wearable sensors;
- compare said sensory data with said stored attendant activity feature data sets to identify a current attendant activity therefrom and associated hygiene status subroutine associated therewith;
- execute said identified associated hygiene status subroutine; and
- upon user non-compliance with said executed subroutine, activating said alerting unit.

18. The system as defined in claim 17, each unit being further configured to:
- form a group of identities for a corresponding number of successive current attendant activities;
- store the identities;
- predict a next attendant activity based on the stored identities;
- select a next hygiene status subroutine according to the next attendant activity; and
- execute the next hygiene status subroutine in advance of the next attendant activity.

19. The system as defined in claim 17, said processor further operable to receive via said receiver hygiene event data from a wearable dispenser worn by the attendant or from a fixed dispenser, and process same in determining user compliance with said executed hygiene status subroutine.

20. The system as defined in claim 17, the sensors including one or more of an accelerometer, a thermometer, a microphone, an elevation meter, a pressure meter, a motion sensor, a global positioning device, a gyroscope, a blood pressure monitor, a heart rate monitor, a muscle activity monitor (electromyographic (EMG) sensors, Mechanomyographic (MMG) sensors), a skin conductance sensor.

21. The system as defined in claim 19, the hygiene event data representative of one or more of a hand wash disinfectant activation, a hand wash sink activation, a soap dispenser activation, a towel activation, a glove dispenser activation and blower activation.

22. The system as defined in claim 19, one or more of the one or more sensors being configured to measure one or more signals of the attendant activity, including linear acceleration, angular acceleration, temperature, air pressure, and/or sound, or one or more physiological signals including heart rate, blood pressure, muscle activity, and/or skin conductance of the attendant.

23. The system as defined in claim 19, the processor employing one or more pattern recognition subroutines to identify said current attendant activity.

24. A method of promoting hand hygiene compliance by a user in a facility via a wearable zone detector to be worn by the user, the wearable zone detector including an on-board control unit, a memory, a receiver and an alert unit, the method comprising:
- a) receiving via the receiver a zone identifier signal from a zone within the facility, said zone identifier signal providing a zone identifier and a zone type of the zone to the on-board control unit;
- b) comparing the provided zone identifier with a stored zone identifier stored in the memory to determine a change of zone;
- c) responsive to determining a change of zone, starting at least one timer; and
- d) responsive to expiration of the at least one timer, activating an alert;

the method further comprising, upon determining a zone change, automatically selecting via the on-board control unit one or more of said alert and said at least one timer according to said zone type identifier.

* * * * *